United States Patent
Barinka et al.

(10) Patent No.: US 11,773,182 B2
(45) Date of Patent: Oct. 3, 2023

(54) DEVELOPMENT OF NEW MONOCLONAL ANTIBODIES RECOGNIZING HUMAN PROSTATE-SPECIFIC MEMBRANE ANTIGEN (PSMA)

(71) Applicants: The Johns Hopkins University, Baltimore, MD (US); Institute of Biotechnology CAS, V.V.I., Vestec (CZ)

(72) Inventors: Cyril Barinka, Vestec (CZ); Martin G. Pomper, Baltimore, MD (US); Zora Novakova, Vestec (CZ); Catherine A. Foss, Baltimore, MD (US)

(73) Assignees: The Johns Hopkins University, Baltimore, MD (US); Institute of Biotechnology CAS, V.V.I., Vestec (CZ)

( * ) Notice: Subject to any disclaimer, the term of this patent is extended or adjusted under 35 U.S.C. 154(b) by 527 days.

(21) Appl. No.: 16/475,805

(22) PCT Filed: Jan. 5, 2018

(86) PCT No.: PCT/US2018/012530
§ 371 (c)(1),
(2) Date: Jul. 3, 2019

(87) PCT Pub. No.: WO2018/129284
PCT Pub. Date: Jul. 12, 2018

(65) Prior Publication Data
US 2019/0330367 A1     Oct. 31, 2019

Related U.S. Application Data

(60) Provisional application No. 62/442,482, filed on Jan. 5, 2017.

(51) Int. Cl.

| | | |
|---|---|---|
| A61K 39/00 | (2006.01) | |
| C07K 16/30 | (2006.01) | |
| A61K 47/68 | (2017.01) | |
| A61K 49/00 | (2006.01) | |
| A61K 51/10 | (2006.01) | |
| G01N 33/574 | (2006.01) | |
| A61K 39/395 | (2006.01) | |

(52) U.S. Cl.
CPC .......... *C07K 16/3069* (2013.01); *A61K 47/68* (2017.08); *A61K 49/0032* (2013.01); *A61K 49/0058* (2013.01); *A61K 51/1072* (2013.01); *G01N 33/57434* (2013.01); *A61K 39/39558* (2013.01); *A61K 2039/505* (2013.01); *C07K 2317/24* (2013.01); *C07K 2317/34* (2013.01); *C07K 2317/51* (2013.01); *C07K 2317/92* (2013.01)

(58) Field of Classification Search
CPC ............. A61K 2039/505; A61K 39/39558
See application file for complete search history.

(56) References Cited

U.S. PATENT DOCUMENTS

| | | | |
|---|---|---|---|
| 5,741,957 | A | 4/1998 | Deboer et al. |
| 5,750,172 | A | 5/1998 | Meade et al. |
| 5,756,687 | A | 5/1998 | Denman et al. |
| 5,827,690 | A | 10/1998 | Meade et al. |
| 2014/0234215 | A1 | 8/2014 | Ho et al. |
| 2015/0273078 | A1 | 10/2015 | Van Berkel et al. |

FOREIGN PATENT DOCUMENTS

| | | |
|---|---|---|
| EP | 0239400 | 9/1987 |
| WO | WO 88/09344 | 12/1988 |
| WO | WO 89/09622 | 10/1989 |
| WO | WO 90/07861 | 7/1990 |
| WO | WO 91/10741 | 7/1991 |
| WO | WO 94/02602 | 2/1994 |
| WO | WO 95/04064 | 2/1995 |
| WO | WO 96/33735 | 10/1996 |
| WO | WO 96/34096 | 10/1996 |
| WO | WO 00/09560 | 2/2000 |
| WO | WO 02/098897 | 12/2002 |

OTHER PUBLICATIONS

Henry et al. (Cancer Res. Nov. 1, 2004; 64: 7995-8001).*
McDevitt et al. (Cancer Res. Nov. 1, 2000; 60: 6095-6100).*
Yamaguchi et al. (Biochem. Biophys. Res. Commun. Nov. 1, 2014; 454 (4): 600-603).*
Pettersen et al. (J. Immunol. Jun. 15, 1999; 162 (12): 7031-7040).*
Bernard et al. (Human Immunol. 1986; 17: 388-405).*
Winkler et al. (J. Immunol. Oct. 15, 2000; 165 (8): 4505-4514).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*

(Continued)

*Primary Examiner* — Stephen L Rawlings
(74) *Attorney, Agent, or Firm* — CASIMIR JONES S.C.; Thomas A. Isenbarger

(57) ABSTRACT

The presently disclosed subject matter provides compositions and methods comprising isolated antibodies that can recognize human prostate-specific membrane antigen (PSMA). The presently disclosed antibodies can be used to for imaging and therapy of PSMA-expressing cancers, such as prostate cancer, in a subject.

18 Claims, 18 Drawing Sheets
Specification includes a Sequence Listing.

(56) References Cited

OTHER PUBLICATIONS

Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Schmittgen et al. (Int. J. Cancer. Nov. 1, 2003; 107 (2): 323-9).*
Ausubel et al., Current Protocols in Molecular Biology, Green Publishing Associates and Wiley Interscience, N.Y. 1994. TOC only. 14 pages.
Banerjee et al., Synthesis and Evaluation of Gd(lll) -Based Magnetic Resonance Contrast Agents for Molecular Imaging of Prostate-Specific Membrane Antigen. Angew Chern Int Ed Engl. Sep. 7, 2015;54(37):10778-82.
Barinka et al., Amino acids at the N- and C-termini of human glutamate carboxypeptidase II are required for enzymatic activity and proper folding. Eur J Biochem. Jul. 2004;271(13):2782-90.
Barinka et al., Glutamate carboxypeptidase II in diagnosis and treatment of neurologic disorders and prostate cancer. Curr Med Chem 2012;19(6):856-70.
Barinka et al., Selection and characterization of Anticalins targeting human prostate-specific membrane antigen (PSMA). Protein Eng Des Sel. Mar. 2016;29(3):105-15.
Bostwick et al., Prostate specific membrane antigen expression in prostatic intraepithelial neoplasia and adenocarcinoma: a study of 184 cases. Cancer. Jun. 1, 1998;82(11):2256-61.
Bouchelouche et al., Positron emission tomography/computed tomography and radioimmunotherapy of prostate cancer. Curr Opin Oncol. Sep. 2009;21(5):469-74.
Chang et al., Prostate-specific membrane antigen is produced in tumor-associated neovasculature. Clin Cancer Res. Oct. 1999;5(10):2674-81.
Dassie et al., Targeted inhibition of prostate cancer metastases with an RNA aptamer to prostate-specific membrane antigen. Mol Ther. Nov. 2014;22(11):1910-22.
Ellis et al., Ten-year outcomes: the clinical utility of single photon emission computed tomography/computed tomography capromab pendetide (Prostascint) in a cohort diagnosed with localized prostate cancer. Int J Radiat Oncol Biol Phys. Sep. 1, 2011;81(1):29-34.
Elsasser-Beile et al., A new generation of monoclonal and recombinant antibodies against cell-adherent prostate specific membrane antigen for diagnostic and therapeutic targeting of prostate cancer. Prostate. Sep. 15, 2006;66(13):1359-70.
Foss et al., GCPII imaging and cancer. Curr Med Chem. 2012;19(9):1346-59.
GenBank: 1DQJ_A. Downloaded Jul. 7, 2022. 2 pages.
GenBank: BAQ25544.1. Feb. 10, 2015. 2 pages.
Gordon et al., Prostate-specific membrane antigen expression in regeneration and repair. Mod Pathol. Dec. 2008;21(12):1421-7.
Haberkorn et al., New Strategies in Prostate Cancer: Prostate-Specific Membrane Antigen (PSMA) Ligands for Diagnosis and Therapy. Clin Cancer Res. Jan. 1, 2016;22(1):9-15.
Harlow and Lane "Antibodies, A Laboratory Manual", CSH Press, Cold Spring Harbor, 1988. TOC only. 9 pages.
Higgins et al., CLUSTAL V: improved software for multiple sequence alignment. Comput Appl Biosci. Apr. 1992;8(2):189-91.
Higgins et al., Fast and sensitive multiple sequence alignments on a microcomputer. Comput Appl Biosci. Apr. 1989;5(2):151-3.
Hlouchova et al., Structural insight into the evolutionary and pharmacologic homology of glutamate oarboxypeptidases II and III. FEBS J. Aug. 2009;276(16):4448-62.
Hohberg et al., Lacrimal Glands May Represent Organs at Risk for Radionuclide Therapy of Prostate Cancer with [Lu]DKFZ-PSMA-617, Molecular Imaging and Biology. 2016: 18: 437-445.
Holland et al., 892r-DFO-J591 for immunoPET of prostate-specific membrane antigen expression in vivo. J Nucl Med. Aug. 2010;51(8):1293-300.
Huber et al., Comprehensive validation of published immunohistochemical prognostic biomarkers of prostate cancer—what has gone wrong? A blueprint for the way forward in biomarker studies. Br J Cancer. Jan. 6, 2015;112(1):140-8.

International Search Report and Written Opinion for PCT/US2018/012530, dated Apr. 30, 2018. 13 pages.
Joyner, Gene Targeting, A Practical Approach, Oxford University Press. 2000. TOC only. 9 pages.
Kampmeier et al., Design and preclinical evaluation of a 99mTc-labelled diabody of mAb J591 for SPECT imaging of prostate-specific membrane antigen (PSMA). EJNMMI Res. Mar. 7, 2014;4(1):13. 10 pages.
Kiess et al., Auger Radiopharmaceutical Therapy Targeting Prostate-Specific Membrane Antigen. J Nucl Med. Sep. 2015;56(9):1401-1407.
Kiess et al., Prostate-specific membrane antigen as a target for cancer imaging and therapy. Q J Nucl Med Mol Imaging. Sep. 2015;59(3):241-68.
Kratochwil et al., PSMA-Targeted Radionuclide Therapy of Metastatic Castration-Resistant Prostate Cancer with 177Lu-Labeled PSMA-617. J Nucl Med. Aug. 2016;57(8):1170-6.
Kull et al., Mixtures of quaternary ammonium compounds and long-chain fatty acids as antifungal agents. Appl Microbiol. Nov. 1961;9(6):538-41.
Larson et al., Radioimmunotherapy of human tumours. Nat Rev Cancer. Jun. 2015;15(6):347-60.
Le Mouellic et al., Targeted replacement of the homeobox gene Hox-3.1 by the *Escherichia coli* lacZ in mouse chimeric embryos. Proc Natl Acad Sci U S A. Jun. 1990;87(12):4712-6.
Liu et al., Monoclonal antibodies to the extracellular domain of prostate-specific membrane antigen also react with tumor vascular endothelium. Cancer Res. Sep. 1, 1997;57(17):3629-34.
Malmborg et al., BIAcore as a tool in antibody engineering. J Immunol Methods. Jun. 14, 1995;183(1):7-13.
Milowsky et al., Vascular targeted therapy with anti-prostate-specific membrane antigen monoclonal antibody J591 in advanced solid tumors. J Clin Oncol. Feb. 10, 2007;25(5):540-7.
Myszka. Improving biosensor analysis. J Mol Recognit. Sep.-Oct. 1999;12(5):279-84.
Nakajima et al., Targeted, activatable, in vivo fluorescence imaging of prostate-specific membrane antigen (PSMA) positive tumors using the quenched humanized J591 antibody-indocyanine green (ICG) conjugate. Bioconjug Chem. Aug. 17, 2011;22(8):1700-5.
NCBI Reference sequence: NM_004476.1 . Apr. 25, 2017. Retrieved from internet: NCBI.NLM.NIH.GOV/nuccore/NM_004476.1 on Jul. 11, 2022. 5 pages.
Ng et al., Acute tumor vascular effects following fractionated radiotherapy in human lung cancer: In vivo whole tumor assessment using volumetric perfusion computed tomography. Int J Radiat Oncol Biol Phys. Feb. 1, 2007;67(2):417-24.
O'Keefe et al., Comparative analysis of prostate-specific membrane antigen (PSMA) versus a prostate-specific membrane antigen-like gene. Prostate. Feb. 1, 2004;58(2):200-10.
Osborne et al., Prostate-specific membrane antigen-based imaging. Urol Oncol. Feb. 2013;31(2):144-54.
Peknicova et al., Preparation and characterization of a monoclonal antibody against boar acrosin. Folia Biol (Praha) 1986;32(4):282-5.
Rovenska et al., Tissue expression and enzymologic characterization of human prostate specific membrane antigen and its rat and pig orthologs. Prostate. Feb. 1, 2008;68(2):171-82.
Rowe et al., PSMA-Based [18F]DCFPyL PET/CT Is Superior to Conventional Imaging for Lesion Detection in Patients with Metastatic Prostate Cancer. Mol Imaging Biol 2016; 18(3): 411-419.
Sacha et al., iBodies: Modular Synthetic Antibody Mimetics Based on Hydrophilic Polymers Decorated with Functional Moieties. Angew Chern Int Ed Engl. Feb. 12, 2016;55(7):2356-60.
Sambrook. Molecular Cloning a Laboratory Manual, Cold Spring Harbor Laboratory Third Edition. 2001. TOC only. 23 pages.
Schier et al., Efficient in vitro affinity maturation of phage antibodies using BIAcore guided selections. Hum Antibodies Hybridomas. 1996;7(3):97-105.
Scopes, "Protein Purification", Springer-Verlag, N.Y. 1993. TOC only. 15 pages.
Siegel et al., Cancer statistics, 2015. CA Cancer J Clin. Jan.-Feb. 2015;65(1):5-29.

(56) References Cited

OTHER PUBLICATIONS

Smith-Jones et al., In vitro characterization of radiolabeled monoclonal antibodies specific for the extracellular domain of prostate-specific membrane antigen. Cancer Res. Sep. 15, 2000;60(18):5237-43.

Sofou. Radionuclide carriers for targeting of cancer. Int J Nanomedicine. 2008;3(2):181-99.

Tagawa et al., Bone marrow recovery and subsequent chemotherapy following radiolabeled anti-prostate-specific membrane antigen monoclonal antibody j591 in men with metastatic castration-resistant prostate cancer. Front Oncol. Aug. 26, 2013;3:214.

Tagawa et al., Phase II study of Lutetium-177-labeled anti-prostate-specific membrane antigen monoclonal antibody J591 for metastatic castration-resistant prostate cancer. Clin Cancer Res. Sep. 15, 2013;19(18):5182-91.

Troyer et al., Location of prostate-specific membrane antigen in the LNCaP prostate carcinoma cell line. Prostate. Mar. 1, 1997;30(4):232-42.

Tykvart et al., Comparative analysis of monoclonal antibodies against prostate-specific membrane antigen (PSMA). Prostate. Dec. 2014;74(16):1674-90.

Tykvart et al., Efficient and versatile one-step affinity purification of in vivo biotinylated proteins: expression, characterization and structure analysis of recombinant human glutamate carboxypeptidase II. Protein Expr Purif. Mar. 2012;82(1):106-15.

Wernicke et al., Prostate-specific Membrane Antigen (PSMA) Expression in the Neovasculature of Gynecologic Malignancies: Implications for PSMA-targeted Therapy. Appl Immunohistochem Mol Morphol. Apr. 2017;25(4):271-276.

Wiehr et al., Pharmacokinetics and PET imaging properties of two recombinant anti-PSMA antibody fragments in comparison to their parental antibody. Prostate. May 2014;74(7):743-55.

Wittrup et al., Practical theoretic guidance for the design of tumor-targeting agents. Methods Enzymol 2012;503:255-68.

Yang et al., [(18)F]Fluorobenzoyllysinepentanedioic Acid Carbamates: New Scaffolds for Positron Emission Tomography (PET) Imaging of Prostate-Specific Membrane Antigen (PSMA). J Med Chem. 2016. 59(1):206-218.

Zhu et al., Nanoconjugation of PSMA-Targeting Ligands Enhances Perinuclear Localization and Improves Efficacy of Delivered Alpha-Particle Emitters against Tumor Endothelial Analogues. Mol Cancer Ther. Jan. 2016;15(1):106-113.

\* cited by examiner

5B1 light chain
Amino acid sequence – VL-CL domain

DIVLTQSPATLSVTPGDSVSLSCRASQSISNHLHWYQQKSHESPRLLIKFVSQSISGIPSRFSGSGSGTDFT
LSINSVETEDFGMYFCQQSNSWPWTFGGGTKLEIKRADAAPTVSIFPPSSEQLTSGGASVVCFLNNFYPKD
INVKWKIDGSERQNGVLNSWTDQDSKDSTYSMSSTLTLTKDEYERHNSYTCEATHKTSTSPIVKSFNRNEC
(SEQ. ID. NO. 1)

5B1 heavy chain
Amino acid sequence - VH-CH1 domain

DVKLVESGGDLVNLGGSLKLSCAASGFTFSGYYMSWVRQTPEKRLELVAAINSDGDNTYYTDTVKGRFTI
SRDNAKNTLYMQMSSLKSEDTALYYCARHEDGYWAWFVYWGQGTLVTVSAAKTTPPSVYPLAPGSAAQ
TNSMVTLGCLVKGYFPEPVTVTWNSGSLSSGVHTFPAVLQSDLYTLSSSVTVPSSTWPSETVTCNVAHPA
SSTKVDKK (SEQ. ID. NO. 2)

5B1 heavy chain
Amino acid sequence – CH2-CH3 domain (Fc part)

IVPRDCGCKPCICTVPEVSSVFIFPPKPKDVLTITLTPKVTCVVVDISKDDPEVQFSWFVDDVEVHTAQTQPR
EEQFNSTFRSVSELPIMHQDWLNGKEFKCRVNSAAFPAPIEKTISKTKGRPKAPQVYTIPPPKEQMAKDKV
SLTCMITDFFPEDITVEWQWNGQPAENYKNTQPIMDTDGSYFVYSKLNVQKSNWEAGNTFTCSVLHEGLH
NHHTEKSLSHSPG (SEQ. ID. NO. 3)

5B1 light chain
Nucleotide sequence – VL-CL domain
GATATTGTGCTaACTCAGTCTCCAGCCACCCTGTCTGTGACTCCAGGAGATAGCGTCAGTCTTTCCTGC
AGGGCCAGCCAAAGTATTAGCAACCACCTACACTGGTATCAACAAAAATCACATGAGTCTCCAAGGCTT
CTCATCAAGTTTGTTTCCCAGTCCATCTCTGGGATCCCCTCCAGGTTCAGTGGCAGTGGATCAGGGACA
GATTTCACTCTCAGTATCAACAGTGTGGAGACTGAAGATTTTGGAATGTATTTCTGTCAACAGAGTAACA
GCTGGCCGTGGACGTTCGGTGGAGGCACCAAGCTGGAgATcAAACGGGCTGATGCTGCACCAACTGTA
TCCATCTTCCCACCATCCAGTGAGCAGTTAACATCTGGAGGTGCCTCAGTCGTGTGCTTCTTGAACAAC
TTCTACCCCAAAGACATCAATGTCAAGTGGAAGATTGATGGCAGTGAACGACAAAATGGCGTCCTGAAC
AGTTGGACTGATCAGGACAGCAAAGACAGCACCTACAGCATGAGCAGCACCCTCACGTTGACCAAGGA
CGAGTATGAACGACATAACAGCTATACCTGTGAGGCCACTCACAAGACATCAACTTCACCCATIGTCAAG
AGCTTCAACAGGAATGAGTGT (SEQ. ID. NO. 4)

5B1 heavy chain
Nucleotide sequence - VH-CH1 domain

GACGTGAAGCTAGTGGAGTCTGGGGGAGACTTAGTGAACCTTGGAGGGTCCCTGAAACTCTCCTGTGC
AGCCTCTGGATTCACTTTCAGTGGCTATTATATGTCTTGGGTTCGCCAGACTCCAGAGAAGAGGCTGGA
GTTAGTCGCAGCCATTAATAGTGATGGTGATAATACCTATTATACAGACACTGTGAAGGGCCGATTCAC
CATCTCCAGAGACAATGCCAAGAACACCCTGTATATGCAAATGAGCAGTCTGAAGTCTGAGGACACAGC
CTTGTATTACTGTGCAAGACATGAGGATGGTTACTGGGCCTGGTTTGTTTACTGGGGCCAAGGGACTCT
GGTCACTGTCTCTGcAGCCAAAACGACACCCCCATCTGTCTATCCACTGGCCCCTGGATCTGCTGCCCA
AACTAACTCCATGGTGACCCTGGGATGCCTGGTCAAGGGCTATTTCCCTGAGCCAGTGACAGTGACCT
GGAACTCTGGATCCCTGTCCAGCGGTGTGCACACCTTCCCAGCTGTCCTGCAGTCTGACCTCTACACT
CTGAGCAGCTCAGTGACTGTCCCCTCCAGCACCTGGCCCAGCGAGACCGTCACCTGCAACGTTGCCC
ACCCGGCCAGCAGCACCAAGGTGGACAAGAAA (SEQ. ID. NO. 5)

*FIG. 1*

5D3 light chain
Aminoacid sequence – VL-CL domain

DIQMTQTTSSLSASLGDRVTISCSASQGINNFLTWYQQKPDGTLKLLIYYTSSLHSGVPSRFSGSGSGTDYSLTIRNLEP
EDIATYYCQQYSNLPFTFGGGTKVEIKRADAAPTVSIFPPSSEQLTSGGASVVCFLNNFYPKDINVKWKIDGSERQNGVL
NSWTDQDSKDSTYSMSSTLTLTKDEYERHNSYTCEATHKTSTSPIVKSFNRNEC (SEQ. ID. NO. 6)

5D3 heavy chain
Aminoacid sequence - VH-CH1 domain

EVQLQQSGPELVKPGASVKISCKTSGYAFNTSWMNWVKQRPGQGLEWIGRIYPGDGDTNYNGKFKGKATLTADKSSSTAH
MHLSSLTSVDSAVYFCARGEWYLYYFDYWGQGTTLTVSSAKTTPPSVYPLAPGSAAQTNSMVTLGCLVKGYFPEPVTVTW
NSGSLSSGVHTFPAVLQSDLYTLSSSVTVPSSTWPSETVTCNVAHPASSTKVDKK (SEQ. ID. NO. 7)

5D3 heavy chain
Aminoacid sequence – CH2-CH3 domain (Fc part)

IVPRDCGCKPCICTVPEVSSVFIFPPKPKDVLTITLTPKVTCVVVDISKDDPEVQFSWFVDDVEVHTAQTQPREEQFNST
FRSVSELPIMHQDWLNGKEFKCRVNSAAFPAPIEKTISKTKGRPKAPQVYTIPPPKEQMAKDKVSLTCMITDFFPEDITV
EWQWNGQPAENYKNTQPIMDTDGSYFVYSKLNVQKSNWEAGNTFTCSVLHEGLHNHHTEKSLSHSPG (SEQ. ID.
NO. 3)

5D3 light chain
Nucleotide sequence – VL-CL domain

GaCATCCAGATGaCCCAGACAACATCCTCCCTGTCTGCCTCTCTGGGAGACAGAGTCACCATCAGTTGCAGTGCAAGT
CAGGGCATTAACAATTTTTTAACCTGGTATCAGCAGAAACCAGATGGAACTCTTAAACTCCTGATCTATTACACATCAA
GTTTACACTCAGGAGTCCCATCAAGGTTCAGTGGCAGTGGGTCTGGGACAGATTATTCTCTCACCATTAGGAACCTGG
AACCTGAAGATATTGCCACTTACTATTGTCAGCAATATAGTAACCTTCCGTTCACGTTCGGAGGGGGGACCAAGGTGG
AAATAAAACGGGCTGATGCTGCACCAACTGTATCCATCTTCCCACCATCCAGTGAGCAGTTAACATCTGGAGGTGCCT
CAGTCGTGTGCTTCTTGAACAACTTCTACCCCAAAGACATCAATGTCAAGTGGAAGATTGATGGCAGTGAACGACAAA
ATGGCGTCCTGAACAGTTGGACTGATCAGGACAGCAAAGACAGCACCTACAGCATGAGCAGCACCCTCACGTTGACC
AAGGACGAGTATGAACGACATAACAGCTATACCTGTGAGGCCACTCACAAGACATCAACTTCACCCATTGTCAAGAG
CTTCAACAGGAATGAGTGT (SEQ. ID. NO. 8)

5D3 heavy chain VH+CH1
Nucleotide sequence - VH-CH1 domain

GAGGTTCAGCTTCAGCAGTCTGGACCTGAACTGGTGAAGCCTGGGGCCTCAGTGAAGATTTCCTGCAAAACTTCTGG
CTACGCATTCAATACCTCTTGGATGAACTGGGTGAAGCAGAGGCCTGGACAGGGTCTTGAGTGGATTGGACGGATTT
ATCCTGGAGATGGAGATACTAACTACAATGGGAAGTTCAAGGGCAAGGCCACACTGACTGCAGACAAATCCTCCAGC
ACAGCCCACATGCACCTCAGCAGTCTGACCTCTGTGGATTCTGCGGTCTATTTCTGTGCAAGAGGAGAATGGTACCTT
TACTACTTTGACTACTGGGGCCAAGGCACCACTCTCACAGTCTCCTCAGCCAAAACGACACCCCCATCTGTCTATCCAC
TGGCCCCTGGATCTGCTGCCCAAACTAACTCCATGGTGACCCTGGGATGCCTGGTCAAGGGCTATTTCCCTGAGCCAG
TGACAGTGACCTGGAACTCTGGATCCCTGTCCAGCGGTGTGCACACCTTCCCAGCTGTCCTGCAGTCTGACCTCTACAC
TCTGAGCAGCTCAGTGACTGTCCCCTCCAGCACCTGGCCCagcGAGACCGTcacCTGCaACgTTGCCCACCCGGCCAGC
AGCACCAAGGtGGACAAGAAA (SEQ. ID. NO. 9)

| | 230 | 240 | |
|---|---|---|---|
| human GCPII - | ILYSDPADYF | AGVKSYP | (SEQ. ID. NO. 10) |
| mouse GCPII - | ILYSDPADYF | VAVKSYP | (SEQ. ID. NO. 11) |
| canine GCPII - | ILYSDPADYF | AGVKSYP | (SEQ. ID. NO. 10) |
| rat GCPII - | ILYSDPADYF | VGVKSYP | (SEQ. ID. NO. 12) |
| pig GCPII - | ILYSDPADYF | AGYQSYP | (SEQ. ID. NO. 13) |
| human GCP3 - | ILYSDPADYF | ADVQPYP | (SEQ. ID. NO. 14) |
| mouse GCP3 - | ILYSDPADYF | ADVQPYP | (SEQ. ID. NO. 14) |

1A11

| | 275 | 285 | |
|---|---|---|---|
| human GCPII - | GYPANEYAYR | RGIAEAVG | (SEQ. ID. NO. 15) |
| mouse GCPII - | GYPANEHAYR | HELTNAVG | (SEQ. ID. NO. 16) |
| canine GCPII - | GYPANEYAYR | REVTEAVG | (SEQ. ID. NO. 17) |
| rat GCPII - | GYPANEYAYR | HEFTEAVG | (SEQ. ID. NO. 18) |
| pig GCPII - | GYPANEYAYR | LQIAEAVG | (SEQ. ID. NO. 19) |
| human GCP3 - | GYPAKEYTFR | LPVEEAVG | (SEQ. ID. NO. 20) |
| mouse GCP3 - | GYPAKEYTFR | LPVEEAVG | (SEQ. ID. NO. 20) |

*FIG. 5A*

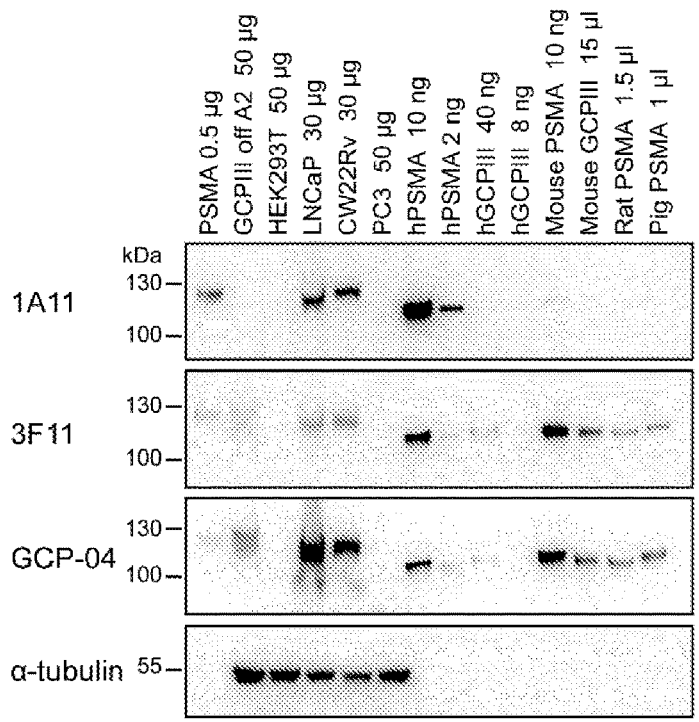

*FIG. 5B*

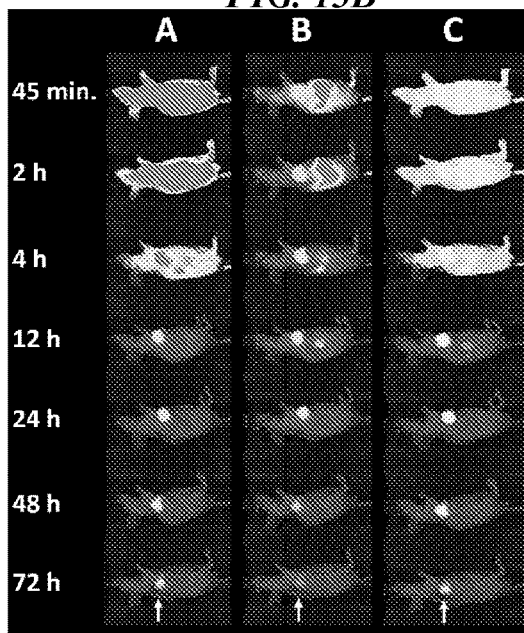 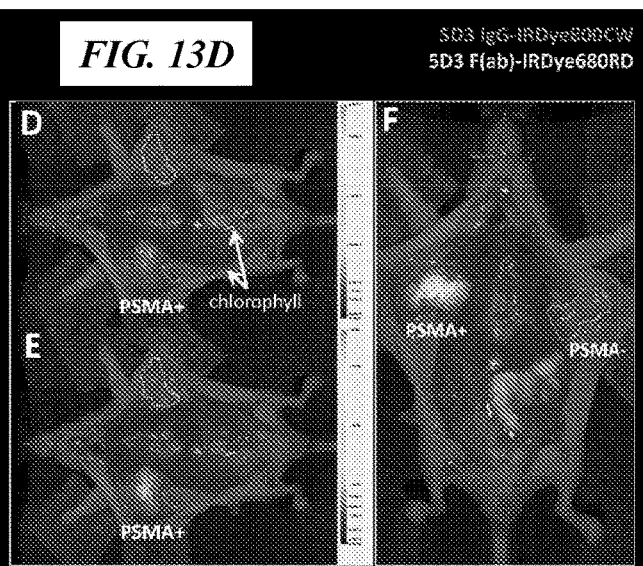
FIG. 13A  FIG. 13B  FIG. 13C  FIG. 13D  FIG. 13E  FIG. 13F

SEQUENCE LISTING

```
<160> NUMBER OF SEQ ID NOS: 23

<210> SEQ ID NO 1
<211> LENGTH: 214
<212> TYPE: PRT
<213> ORGANISM: Mus musculus

<400> SEQUENCE: 1

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn His
            20                  25                  30

Leu His Trp Tyr Gln Gln Lys Ser His Glu Ser Pro Arg Leu Leu Ile
        35                  40                  45

Lys Phe Val Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 2
<211> LENGTH: 216
<212> TYPE: PRT
<213> ORGANISM: Mus musculus

<400> SEQUENCE: 2

Asp Val Lys Leu Val Glu Ser Gly Gly Asp Leu Val Asn Leu Gly Gly
1               5                   10                  15
```

```
Ser Leu Lys Leu Ser Cys Ala Ala Ser Gly Phe Thr Phe Ser Gly Tyr
            20                  25                  30

Tyr Met Ser Trp Val Arg Gln Thr Pro Glu Lys Arg Leu Glu Leu Val
        35                  40                  45

Ala Ala Ile Asn Ser Asp Gly Asp Asn Thr Tyr Tyr Thr Asp Thr Val
 50                  55                  60

Lys Gly Arg Phe Thr Ile Ser Arg Asp Asn Ala Lys Asn Thr Leu Tyr
 65                  70                  75                  80

Met Gln Met Ser Ser Leu Lys Ser Glu Asp Thr Ala Leu Tyr Tyr Cys
                85                  90                  95

Ala Arg His Glu Asp Gly Tyr Trp Ala Trp Phe Val Tyr Trp Gly Gln
            100                 105                 110

Gly Thr Leu Val Thr Val Ser Ala Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys
            210                 215

<210> SEQ ID NO 3
<211> LENGTH: 227
<212> TYPE: PRT
<213> ORGANISM: Mus musculus

<400> SEQUENCE: 3

Ile Val Pro Arg Asp Cys Gly Cys Lys Pro Cys Ile Cys Thr Val Pro
1               5                   10                  15

Glu Val Ser Ser Val Phe Ile Phe Pro Pro Lys Pro Lys Asp Val Leu
            20                  25                  30

Thr Ile Thr Leu Thr Pro Lys Val Thr Cys Val Val Val Asp Ile Ser
        35                  40                  45

Lys Asp Asp Pro Glu Val Gln Phe Ser Trp Phe Val Asp Asp Val Glu
 50                  55                  60

Val His Thr Ala Gln Thr Gln Pro Arg Glu Glu Gln Phe Asn Ser Thr
 65                  70                  75                  80

Phe Arg Ser Val Ser Glu Leu Pro Ile Met His Gln Asp Trp Leu Asn
                85                  90                  95

Gly Lys Glu Phe Lys Cys Arg Val Asn Ser Ala Ala Phe Pro Ala Pro
            100                 105                 110

Ile Glu Lys Thr Ile Ser Lys Thr Lys Gly Arg Pro Lys Ala Pro Gln
            115                 120                 125

Val Tyr Thr Ile Pro Pro Pro Lys Glu Gln Met Ala Lys Asp Lys Val
            130                 135                 140

Ser Leu Thr Cys Met Ile Thr Asp Phe Phe Pro Glu Asp Ile Thr Val
145                 150                 155                 160

Glu Trp Gln Trp Asn Gly Gln Pro Ala Glu Asn Tyr Lys Asn Thr Gln
            165                 170                 175
```

Pro Ile Met Asp Thr Asp Gly Ser Tyr Phe Val Tyr Ser Lys Leu Asn
            180                 185                 190

Val Gln Lys Ser Asn Trp Glu Ala Gly Asn Thr Phe Thr Cys Ser Val
        195                 200                 205

Leu His Glu Gly Leu His Asn His His Thr Glu Lys Ser Leu Ser His
    210                 215                 220

Ser Pro Gly
225

<210> SEQ ID NO 4
<211> LENGTH: 642
<212> TYPE: DNA
<213> ORGANISM: Mus musculus

<400> SEQUENCE: 4

| | |
|---|---|
| gatattgtgc taactcagtc tccagccacc ctgtctgtga ctccaggaga tagcgtcagt | 60 |
| ctttcctgca gggccagcca agtattagc aaccacctac actggtatca acaaaaatca | 120 |
| catgagtctc caaggcttct catcaagttt gtttcccagt ccatctctgg atcccctcc | 180 |
| aggttcagtg gcagtggatc agggacagat ttcactctca gtatcaacag tgtggagact | 240 |
| gaagattttg gaatgtattt ctgtcaacag agtaacagct ggccgtggac gttcggtgga | 300 |
| ggcaccaagc tggagatcaa acgggctgat gctgcaccaa ctgtatccat cttcccacca | 360 |
| tccagtgagc agttaacatc tggaggtgcc tcagtcgtgt gcttcttgaa caacttctac | 420 |
| cccaaagaca tcaatgtcaa gtggaagatt gatggcagtg aacgacaaaa tggcgtcctg | 480 |
| aacagttgga ctgatcagga cagcaaagac agcacctaca gcatgagcag caccctcacg | 540 |
| ttgaccaagg acgagtatga cgacataaac agctatacct gtgaggccac tcacaagaca | 600 |
| tcaacttcac ccattgtcaa gagcttcaac aggaatgagt gt | 642 |

<210> SEQ ID NO 5
<211> LENGTH: 648
<212> TYPE: DNA
<213> ORGANISM: Mus musculus

<400> SEQUENCE: 5

| | |
|---|---|
| gacgtgaagc tagtggagtc tgggggagac ttagtgaacc ttggagggtc cctgaaactc | 60 |
| tcctgtgcag cctctggatt cactttcagt ggctattata tgtcttgggt tcgccagact | 120 |
| ccagagaaga ggctggagtt agtcgcagcc attaatagtg atggtgataa tacctattat | 180 |
| acagacactg tgaagggccg attcaccatc tccagagaca tgccaagaa caccctgtat | 240 |
| atgcaaatga gcagtctgaa gtctgaggac acagccttgt attactgtgc aagacatgag | 300 |
| gatggttact gggcctggtt tgtttactgg ggccaaggga ctctggtcac tgtctctgca | 360 |
| gccaaaacga caccccatc tgtctatcca ctggcccctg gatctgctgc ccaaactaac | 420 |
| tccatggtga ccctgggatg cctggtcaag ggctatttcc ctgagccagt gacagtgacc | 480 |
| tggaactctg gatccctgtc agcggtgtg cacaccttcc cagctgtcct gcagtctgac | 540 |
| ctctacactc tgagcagctc agtgactgtc ccctccagca cctggcccag cgagaccgtc | 600 |
| acctgcaacg ttgcccaccc ggccagcagc accaaggtgg acaagaaa | 648 |

<210> SEQ ID NO 6
<211> LENGTH: 214
<212> TYPE: PRT
<213> ORGANISM: Mus musculus

<400> SEQUENCE: 6

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Asn Asn Phe
            20                  25                  30

Leu Thr Trp Tyr Gln Gln Lys Pro Asp Gly Thr Leu Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Arg Asn Leu Glu Pro
65                  70                  75                  80

Glu Asp Ile Ala Thr Tyr Tyr Cys Gln Gln Tyr Ser Asn Leu Pro Phe
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 7
<211> LENGTH: 215
<212> TYPE: PRT
<213> ORGANISM: Mus musculus

<400> SEQUENCE: 7

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Asn Thr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala His
65                  70                  75                  80

Met His Leu Ser Ser Leu Thr Ser Val Asp Ser Ala Val Tyr Phe Cys
                85                  90                  95

Ala Arg Gly Glu Trp Tyr Leu Tyr Tyr Phe Asp Tyr Trp Gly Gln Gly
            100                 105                 110

Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140
```

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Pro Ser Ser
        180                 185                 190

Thr Trp Pro Ser Glu Thr Val Thr Cys Asn Val Ala His Pro Ala Ser
            195                 200                 205

Ser Thr Lys Val Asp Lys Lys
    210                 215

<210> SEQ ID NO 8
<211> LENGTH: 642
<212> TYPE: DNA
<213> ORGANISM: Mus musculus

<400> SEQUENCE: 8

```
gacatccaga tgacccagac aacatcctcc ctgtctgcct ctctgggaga cagagtcacc    60
atcagttgca gtgcaagtca gggcattaac aattttttaa cctggtatca gcagaaacca   120
gatggaactc ttaaactcct gatctattac acatcaagtt acactcagg agtcccatca    180
aggttcagtg gcagtgggtc tgggacagat tattctctca ccattaggaa cctggaacct   240
gaagatattg ccacttacta ttgtcagcaa tatagtaacc ttccgttcac gttcggaggg   300
gggaccaagg tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642
```

<210> SEQ ID NO 9
<211> LENGTH: 645
<212> TYPE: DNA
<213> ORGANISM: Mus musculus

<400> SEQUENCE: 9

```
gaggttcagc ttcagcagtc tggacctgaa ctggtgaagc ctggggcctc agtgaagatt    60
tcctgcaaaa cttctggcta cgcattcaat acctcttgga tgaactgggt gaagcagagg   120
cctggacagg tcttgagtg gattggacgg atttatcctg agatggaga tactaactac    180
aatgggaagt tcaagggcaa ggccacactg actgcagaca atcctccag cacagcccac   240
atgcacctca gcagtctgac ctctgtggat tctgcggtct atttctgtgc aagaggagaa   300
tggtaccttt actactttga ctactgggc caaggcacca ctctcacagt ctcctcagcc   360
aaaacgacac cccatctgt ctatccactg gcccctggat ctgctgccca actaactcc    420
atggtgaccc tgggatgcct ggtcaagggc tatttccctg agccagtgac agtgacctgg   480
aactctggat ccctgtccag cggtgtgcac accttcccag ctgtcctgca gtctgacctc   540
tacactctga gcagctcagt gactgtcccc tccagcacct ggcccagcga gaccgtcacc   600
tgcaacgttg cccacccggc cagcagcacc aaggtggaca gaaaa                   645
```

<210> SEQ ID NO 10
<211> LENGTH: 18
<212> TYPE: PRT

<213> ORGANISM: Homo sapiens

<400> SEQUENCE: 10

Ile Leu Tyr Ser Asp Pro Ala Asp Tyr Phe Ala Pro Gly Val Lys Ser
1               5                   10                  15

Tyr Pro

<210> SEQ ID NO 11
<211> LENGTH: 18
<212> TYPE: PRT
<213> ORGANISM: Mus musculus

<400> SEQUENCE: 11

Ile Leu Tyr Ser Asp Pro Ala Asp Tyr Phe Val Pro Ala Val Lys Ser
1               5                   10                  15

Tyr Pro

<210> SEQ ID NO 12
<211> LENGTH: 18
<212> TYPE: PRT
<213> ORGANISM: Rattus rattus

<400> SEQUENCE: 12

Ile Leu Tyr Ser Asp Pro Ala Asp Tyr Phe Val Pro Gly Val Lys Ser
1               5                   10                  15

Tyr Pro

<210> SEQ ID NO 13
<211> LENGTH: 18
<212> TYPE: PRT
<213> ORGANISM: Sus scrofa

<400> SEQUENCE: 13

Ile Leu Tyr Ser Asp Pro Ala Asp Tyr Phe Ala Pro Gly Val Gln Ser
1               5                   10                  15

Tyr Pro

<210> SEQ ID NO 14
<211> LENGTH: 18
<212> TYPE: PRT
<213> ORGANISM: Homo sapiens

<400> SEQUENCE: 14

Ile Leu Tyr Ser Asp Pro Ala Asp Tyr Phe Ala Pro Asp Val Gln Pro
1               5                   10                  15

Tyr Pro

<210> SEQ ID NO 15
<211> LENGTH: 18
<212> TYPE: PRT
<213> ORGANISM: Homo sapiens

<400> SEQUENCE: 15

Gly Tyr Pro Ala Asn Glu Tyr Ala Tyr Arg Arg Gly Ile Ala Glu Ala
1               5                   10                  15

Val Gly

<210> SEQ ID NO 16
<211> LENGTH: 18
<212> TYPE: PRT
<213> ORGANISM: Mus musculus

<400> SEQUENCE: 16

Gly Tyr Pro Ala Asn Glu His Ala Tyr Arg His Glu Leu Thr Asn Ala
1               5                   10                  15

Val Gly

<210> SEQ ID NO 17
<211> LENGTH: 18
<212> TYPE: PRT
<213> ORGANISM: Canis lupus

<400> SEQUENCE: 17

Gly Tyr Pro Ala Asn Glu Tyr Ala Tyr Arg Arg Glu Val Thr Glu Ala
1               5                   10                  15

Val Gly

<210> SEQ ID NO 18
<211> LENGTH: 18
<212> TYPE: PRT
<213> ORGANISM: Rattus rattus

<400> SEQUENCE: 18

Gly Tyr Pro Ala Asn Glu Tyr Ala Tyr Arg His Glu Phe Thr Glu Ala
1               5                   10                  15

Val Gly

<210> SEQ ID NO 19
<211> LENGTH: 18
<212> TYPE: PRT
<213> ORGANISM: Sus scrofa

<400> SEQUENCE: 19

Gly Tyr Pro Ala Asn Glu Tyr Ala Tyr Arg Leu Gln Ile Ala Glu Ala
1               5                   10                  15

Val Gly

<210> SEQ ID NO 20
<211> LENGTH: 18
<212> TYPE: PRT
<213> ORGANISM: Homo sapiens

<400> SEQUENCE: 20

Gly Tyr Pro Ala Lys Glu Tyr Thr Phe Arg Leu Pro Val Glu Glu Ala
1               5                   10                  15

Val Gly

<210> SEQ ID NO 21
<211> LENGTH: 119
<212> TYPE: PRT
<213> ORGANISM: Mus musculus

<400> SEQUENCE: 21

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Asn Thr Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Asn Tyr Asn Gly Lys Phe
        50                  55                  60

```
Lys Gly Lys Ala Thr Leu Thr Ala Asp Lys Ser Ser Thr Ala His
 65                  70                  75                  80

Met His Leu Ser Ser Leu Thr Ser Val Asp Ser Ala Val Tyr Phe Cys
                 85                  90                  95

Ala Arg Gly Glu Trp Tyr Leu Tyr Tyr Phe Asp Tyr Trp Gly Gln Gly
            100                 105                 110

Thr Thr Leu Thr Val Ser Ser
        115

<210> SEQ ID NO 22
<211> LENGTH: 109
<212> TYPE: PRT
<213> ORGANISM: Mus musculus

<400> SEQUENCE: 22

Asp Ile Gln Met Thr Gln Thr Thr Ser Ser Leu Ser Ala Ser Leu Gly
 1               5                  10                  15

Asp Arg Val Thr Ile Ser Cys Ser Ala Ser Gln Gly Ile Asn Asn Phe
             20                  25                  30

Leu Thr Trp Tyr Gln Gln Lys Pro Asp Gly Thr Leu Lys Leu Leu Ile
         35                  40                  45

Tyr Tyr Thr Ser Ser Leu His Ser Gly Val Pro Ser Arg Phe Ser Gly
     50                  55                  60

Ser Gly Ser Gly Thr Asp Tyr Ser Leu Thr Ile Arg Asn Leu Glu Pro
 65                  70                  75                  80

Glu Asp Ile Ala Thr Tyr Tyr Cys Gln Gln Tyr Ser Asn Leu Pro Phe
                 85                  90                  95

Thr Phe Gly Gly Gly Thr Lys Val Glu Ile Lys Arg Ala
            100                 105

<210> SEQ ID NO 23
<211> LENGTH: 2653
<212> TYPE: DNA
<213> ORGANISM: Homo sapiens

<400> SEQUENCE: 23
ctcaaaaggg gccggatttc cttctcctgg aggcagatgt tgcctctctc tctcgctcgg      60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gccgcgctg gctgtgcgct ggggcgctgg tgctggcggg tggcttcttt    360
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac tcctccagg atatgaaaat    720 gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
```

```
gttaaaaatg cccagctggc aggggccaaa ggagtcattc tctactccga ccctgctgac    960
tactttgctc ctggggtgaa gtcctatcca gatggttgga atcttcctgg aggtggtgtc   1020
cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
gttcatccaa ttggatacta tgatgcacag aagctcctag aaaaaatggg tggctcagca   1200
ccaccagata gcagctggag aggaagtctc aaagtgccct acaatgttgg acctggcttt   1260
actggaaact tttctacaca aaaagtcaag atgcacatcc actctaccaa tgaagtgaca   1320
agaatttaca atgtgatagg tactctcaga ggagcagtgg aaccagacag atatgtcatt   1380
ctgggaggtc accgggactc atgggtgttt ggtggtattg accctcagag tggagcagct   1440
gttgttcatg aaattgtgag gagctttgga acactgaaaa aggaagggtg gagacctaga   1500
agaacaattt tgtttgcaag ctgggatgca gaagaatttg gtcttcttgg ttctactgag   1560
tgggcagagg agaattcaag actccttcaa gagcgtggcg tggcttatat taatgctgac   1620
tcatctatag aaggaaacta cactctgaga gttgattgta caccgctgat gtacagcttg   1680
gtacacaacc taacaaaaga gctgaaaagc cctgatgaag gctttgaagg caaatctctt   1740
tatgaaagtt ggactaaaaa aagtccttcc ccagagttca gtggcatgcc aggataagc   1800 aaattgggat ctgaaatga ttttgaggtg ttcttccaac gacttggaat tgcttcaggc   1860
agagcacggt atactaaaaa ttgggaaaca aacaaattca gcggctatcc actgtatcac   1920
agtgtctatg aaacatatga gttggtggaa aagttttatg atccaatgtt taaatatcac   1980
ctcactgtgg cccaggttcg aggagggatg gtgtttgagc tagccaattc catagtgctc   2040
ccttttgatt gtcgagatta tgctgtagtt ttaagaaagt atgctgacaa aatctacagt   2100
atttctatga aacatccaca ggaaatgaag acatacagtg tatcatttga ttcacttttt   2160
tctgcagtaa agaattttac agaaattgct tccaagttca gtgagagact ccaggacttt   2220
gacaaaagca acccaatagt attaagaatg atgaatgatc aactcatgtt tctggaaaga   2280
gcatttattg atccattagg gttaccagac aggccttttt ataggcatgt catctatgct   2340
ccaagcagcc acaacaagta tgcagggag tcattcccag gaatttatga tgctctgttt   2400
gatattgaaa gcaaagtgga cccttccaag gcctggggag aagtgaagag acagatttat   2460
gttgcagcct tcacagtgca ggcagctgca gagactttga gtgaagtagc ctaagaggat   2520 tcttagaga atccgtattg aatttgtgtg gtatgtcact cagaaagaat cgtaatgggt   2580
atattgataa attttaaaat tggtatattt gaaataaagt tgaatattat atataaaaaa   2640
aaaaaaaaaa aaa                                                      2653
```

DEVELOPMENT OF NEW MONOCLONAL ANTIBODIES RECOGNIZING HUMAN PROSTATE-SPECIFIC MEMBRANE ANTIGEN (PSMA)

CROSS-REFERENCE TO RELATED APPLICATIONS

This is a national phase 35 U.S.C. § 371 application of PCT International Application No. PCT/US2018/012530, filed Jan. 5, 2018, which claims the benefit and priority to U.S. Patent Application No. 62/442,448, filed Jan. 5, 2017, the entire content of each of which is hereby incorporated by reference.

INCORPORATION-BY-REFERENCE OF MATERIAL SUBMITTED ELECTRONICALLY

This application contains a sequence listing. It has been submitted electronically via EFS-Web as an ASCII text file entitled "36627-252_SEQUENCE_LISTING_ST25". The sequence listing is 21,958 bytes in size, and was created on Nov. 15, 2022. It is hereby incorporated by reference in its entirety.

BACKGROUND

Prostate carcinoma (PCa) is by far the most common non-cutaneous malignancy in men and the second cause of cancer-related deaths, accounting for 9% of all male cancer-related fatalities in the US in 2015 (Siegel et al., 2015). A recently published comprehensive validation of immunohistochemical biomarkers of PCa emphasized prostate-specific membrane antigen (PSMA) as one of only four independent prognostic markers for prostate-specific antigen relapse following radical prostatectomy (Huber et al., 2015). PSMA, also known as glutamate carboxypeptidase II (GCPII), is a membrane-bound metallopeptidase with an expression pattern restricted mainly to the healthy prostate secretory-acinar epithelium and on the plasma membrane of epithelial PCa. Dysplastic and neoplastic transformation of the prostate tissue is accompanied by substantial increase in PSMA levels, with the most prominent expression observed in high-grade, metastatic, and castration-resistant disease (Bostwick et al., 1998). Apart from PCa tissue, PSMA was also found in the neovasculature of a variety of solid tumors, but not physiological healthy vasculature (Chang et al., 1999; Wernicke et al., 2016) aside from within granulation tissue, secretory endometrium and frequently within keloid scars (Gordon et al., 2008). As a result of a fairly restricted PSMA expression pattern, bioactive molecules targeting PSMA associated with either PCa or tumor neovasculature provide therapeutic opportunities and offer diagnostic tools for the detection of various solid cancers (Barinka et al., 2012; Foss et al., 2012; Kiess, Banerjee et al., 2015).

Small-molecule ligands comprise the most prominent class of PSMA-specific reagents. For biomedical applications (in particular, PCa imaging and therapy) the inhibitor molecules are functionalized with a suitable tracer, such as a radionuclide, fluorescent dye, magnetic resonance (MR) contrast agent, or a toxin (Foss et al., 2012; Kiess, Banerjee et al., 2015; Sacha et al., 2016). Within the last several years, urea-based compounds have become most prominent in the field, and numerous clinical trials are ongoing to validate their use in patients with PCa and other cancers (Haberkorn et al., 2016; Kratochwil et al., 2016; Rowe et al., 2016). Small molecules offer distinct advantages, such as high affinity, very rapid clearance and ease of synthesis and formulation. On the other hand, potential caveats especially for therapeutic applications might include promiscuous binding to glutamate carboxypeptidease 3 (GCP3; a human paralog of PSMA with high structural similarity), (Hlouchova et al., 2009), nephrotoxicity, and pronounced accumulation to lacrimal and salivary glands (Hohberg et al., 2016).

Macromolecular reagents, most notably monoclonal antibodies (mAbs), offer a viable alternative to small-molecule PSMA ligands for imaging and therapy (Barinka et al., 2016; Dassie et al., 2014; Zhu et al., 2016; Wiehr et al., 2014). Consequently, several mAbs, as well as their conjugates and derivatives are being evaluated in a variety of experimental and preclinical models. At present, J591 and 7E11 (including their conjugates) are the only two anti-PSMA antibodies that have been developed beyond phase I clinical trials, with the $^{111}$In-labeled 7E11/CYT-356 (PROSTASCINT) constituting the only mAb approved by the FDA for PCa imaging. However, (PROSTASCINT) recognizes an intracellular epitope of PSMA and, therefore, it primarily binds to necrotic cells. Accordingly, (PROSTASCINT) displays compromised sensitivity and is not suitable for live cell staining, including the imaging of tumor neovasculature (Ellis et al., 2011).

These limitations were mitigated by the development of second generation mAbs that recognize extracellular epitopes of human PSMA, most notably J591. The murine mAb J591 was described and characterized in 1997 by Liu et al. (1997) and, currently, is the most advanced second generation mAb. Various conjugates of J591 (or its humanized form) have been prepared and characterized as potential diagnostic and therapeutic agents and are subject to late-stage clinical trials (Liu et al., 1997; Holland et al., 2010; Kampmeier et al., 2014; Tagawa, Akhtar et al., 2013; Tagawa, Milowsky et al., 2013). Drawbacks of existing anti-PSMA antibodies, however, include limited commercial availability, poorly defined epitopes, and lack of data on cross-reactivity towards GCPII paralogs and orthologs.

SUMMARY

In one aspect, the presently disclosed subject matter provides an isolated antibody, antibody fragment, or derivative thereof that specifically binds prostate specific membrane antigen (PSMA) and comprises a protein sequence at least 90% identical to any one of SEQ ID NOs: 1, 2, 6 and 7. In some aspects, the antibody, fragment, or derivative comprises a protein sequence which is 100% identical to any one of SEQ ID NOs:1, 2, 6 and 7.

In some aspects, the antibody, fragment, or derivative comprises a VL-CL domain that comprises a protein sequence that is at least 90% identical to SEQ ID NO:1 and a VH-CH1 domain that comprises a protein sequence that is at least 90% identical to SEQ ID NO:2. In some aspects, the antibody, fragment, or derivative comprises a VL-CL domain that comprises a protein sequence that is 100% identical to SEQ ID NO:1 and a VH-CH1 domain that comprises a protein sequence that is 100% identical to SEQ ID NO:2.

In some aspects, the antibody, fragment, or derivative comprises a VL-CL domain that comprises a protein sequence that is at least 90% identical to SEQ ID NO:6 and a VH-CH1 domain that comprises a protein sequence that is at least 90% identical to SEQ ID NO:7. In some aspects, the antibody, fragment, or derivative comprises a VL-CL domain that comprises a protein sequence that is 100% identical to SEQ ID NO:6 and a VH-CH1 domain that comprises a protein sequence that is 100% identical to SEQ ID NO:7.

In some aspects, the antibody, fragment, or derivative binds PSMA in its native form. In some aspects, the binding of PSMA in its native form occurs on the surface of at least one PSMA-expressing cancer cell. In some aspects, the binding of PSMA in its native form by the antibody, fragment, or derivative on the surface of at least one PSMA-expressing cancer cell inhibits survival of the at least one PSMA-expressing cancer cell. In some aspects, the binding of PSMA in its native form by the antibody, fragment, or derivative on the surface of the at least one PSMA-expressing cancer cell can be used to image the at least one PSMA-expressing cancer cell. In some aspects, the antibody is a humanized antibody. In other aspects, the antibody is a chimeric antibody. In certain aspects, the presently disclosed antibody, fragment, or derivative binds PSMA and is suitable for targeting PSMA in its native conformation by techniques, such as (sandwich) ELISA, immunofluorescence, flow cytometry, and immunohistochemistry and in vivo imaging and therapy.

In some aspects, the antibody, fragment, or derivative is conjugated to at least one agent. In some aspects, the at least one agent is a therapeutic agent and/or an imaging agent. In particular aspects, the at least one agent comprises a therapeutic agent and the therapeutic agent comprises a radionuclide suitable for use in alpha therapy, including, but not limited to $^{211}$At, $^{225}$Ac, $^{213}$Bi, $^{212}$Bi, $^{227}$Th, $^{212}$Pb, and $^{223}$Ra. In some aspects, the antibody, fragment, or derivative is conjugated to the at least one agent via a linker.

In certain aspects, the presently disclosed subject matter provides a pharmaceutical composition comprising a presently disclosed antibody, fragment, or derivative thereof.

In other aspects, the presently disclosed subject matter provides a diagnostic composition comprising a presently disclosed antibody, fragment, or derivative thereof.

In some aspects, the presently disclosed subject matter provides a method for assessing the presence of a PSMA-expressing cancer cell or tissue, the method comprising: (a) contacting a cell or tissue suspected of expressing PSMA on its surface with a presently disclosed the antibody, fragment, or derivative thereof, wherein the presence of PSMA creates an antibody-PSMA complex; (b) applying a detection agent that detects the antibody-PSMA complex; and (c) determining the presence of the PSMA-expressing cancer cell or tissue when the detection agent detects the antibody-PSMA complex.

In certain aspects, the presently disclosed subject matter provides a method for inhibiting the growth or survival of a PSMA-expressing cancer cell, the method comprising contacting the surface of the PSMA-expressing cancer cell with a presently disclosed antibody, fragment, or derivative thereof, wherein the presence of PSMA creates an antibody-PSMA complex, thereby inhibiting the growth or survival of the PSMA-expressing cancer cell.

In some aspects, the contacting is performed in vitro or ex vivo. In some aspects, the contacting is performed in vivo in a subject. In some aspects, the subject is a human.

In particular aspects, the presently disclosed subject matter provides a method for inhibiting growth and/or metastasis of a tumor in a subject having or suspected of having a PSMA-expressing cancer, the method comprising administering to the subject a presently disclosed antibody, fragment, or derivative thereof, or a presently disclosed pharmaceutical composition, in an amount effective to inhibit growth and/or metastasis of the tumor in the subject, wherein administering to the subject creates antibody-PSMA complexes in the subject.

In certain aspects, the presently disclosed subject matter provides a method for the treatment of a PSMA-expressing cancer in a subject in need thereof, the method comprising administering to the subject a presently disclosed antibody, fragment, or derivative thereof, or a presently disclosed pharmaceutical composition, in an amount effective to treat the PSMA-expressing cancer in the subject, wherein administering to the subject creates antibody-PSMA complexes in the subject.

In some aspects, the method further comprises administering to the subject an effective amount of a conventional cancer treatment. Examples of conventional cancer treatment include, but are not limited to, chemotherapy, radiotherapy, immunotherapy, proton therapy, photodynamic therapy, and surgery.

In other aspects, the presently disclosed subject matter provides a method for targeting PSMA expressed by a PSMA-expressing cancer cell in a subject, the method comprising administering to the subject a presently disclosed antibody, fragment, or derivative thereof, a presently disclosed pharmaceutical composition, or a presently disclosed diagnostic composition, wherein administering to the subject creates antibody-PSMA complexes in the subject.

In some aspects, the PSMA-expressing cancer is prostate cancer.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 3A:
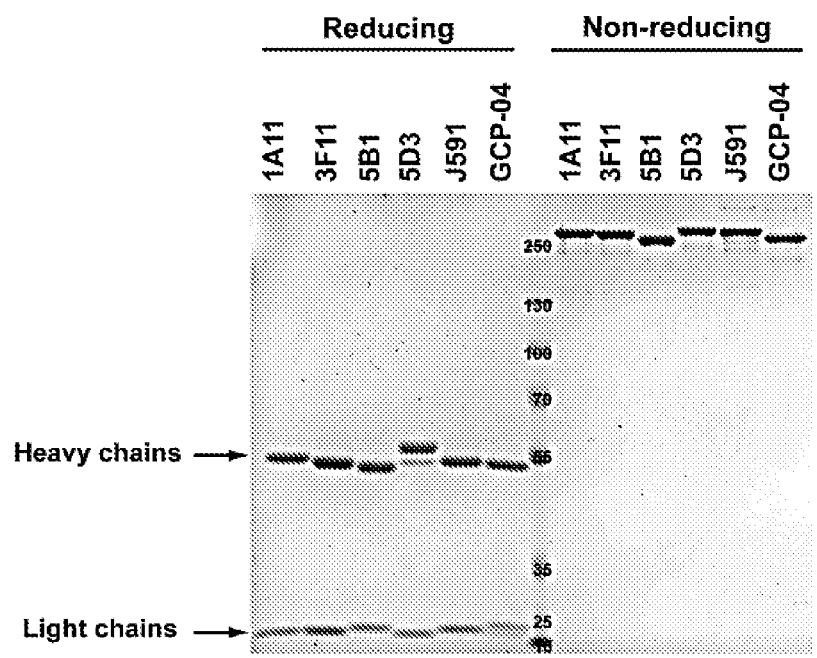
Figure 3B:
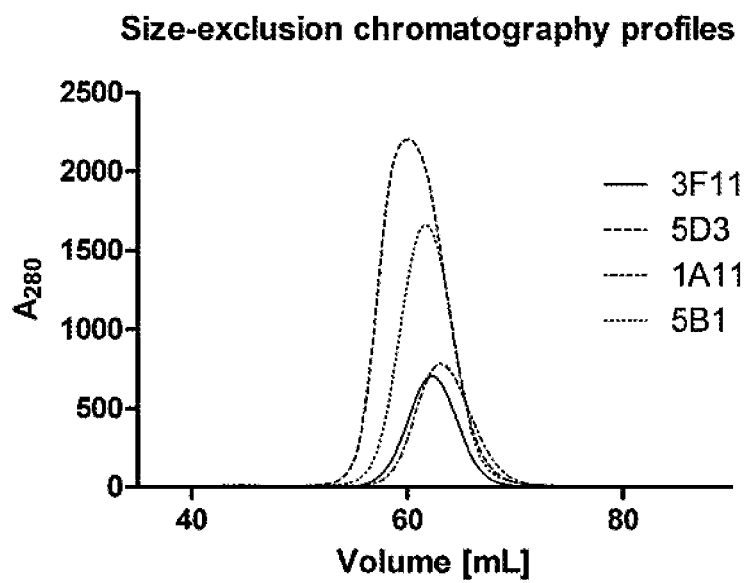
Figure 4:
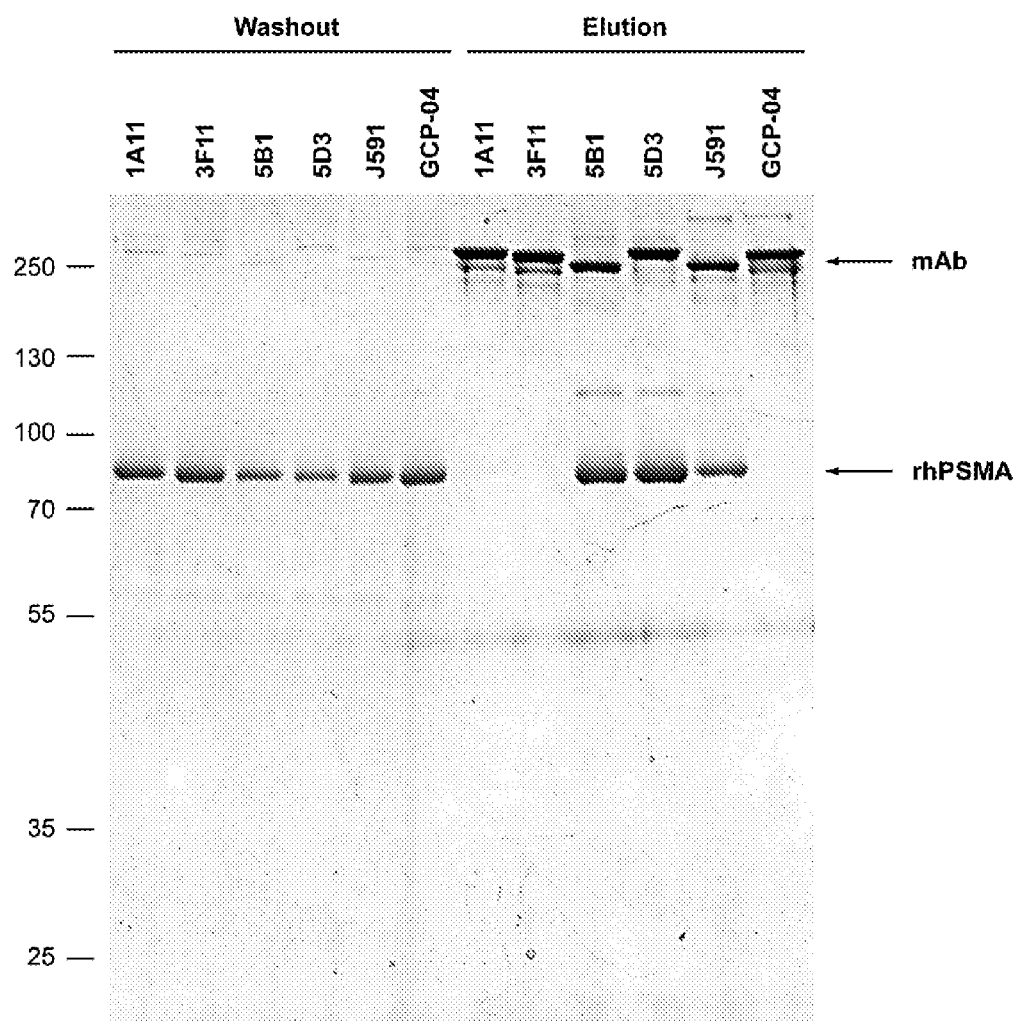
Figure 6:
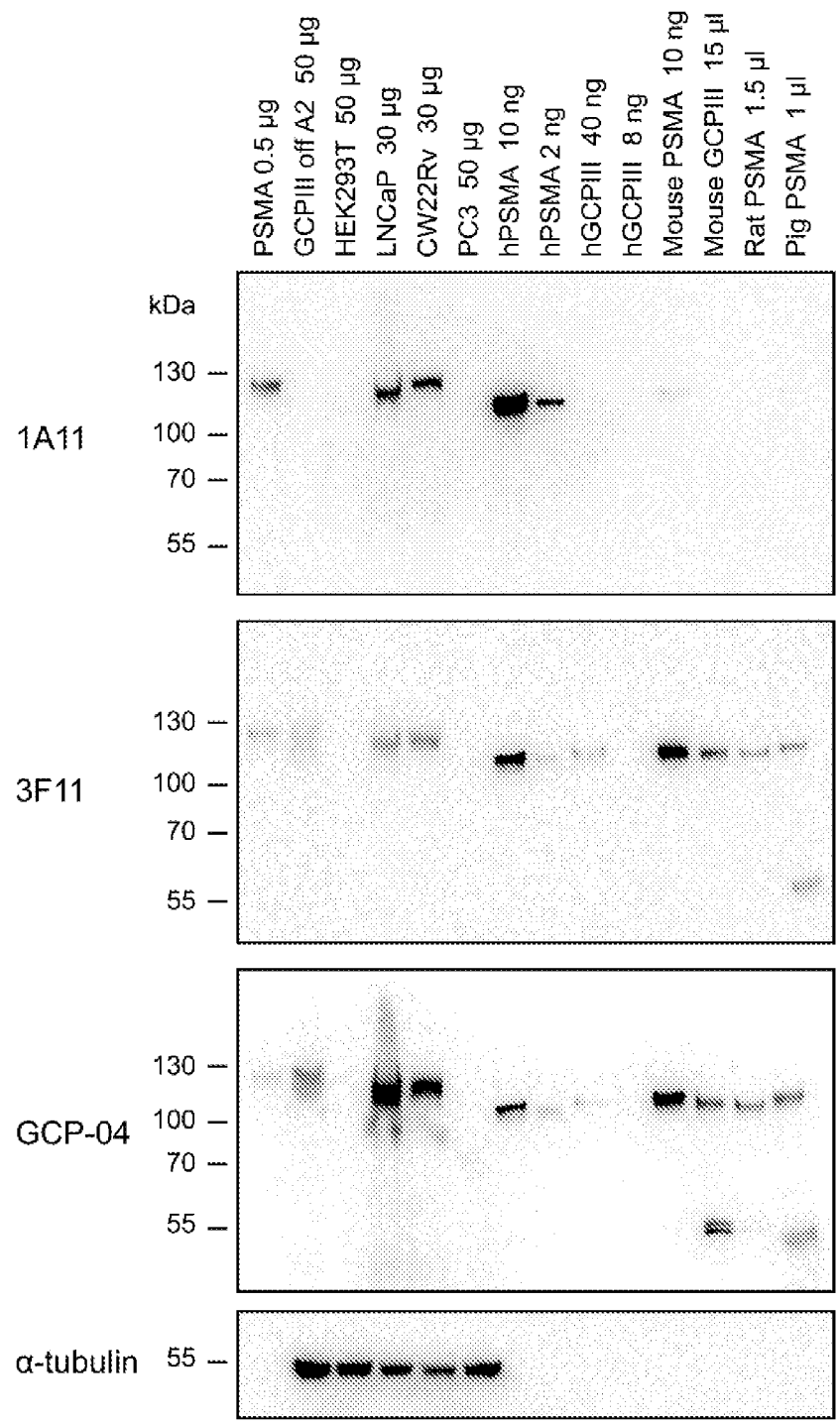
Figure 7:
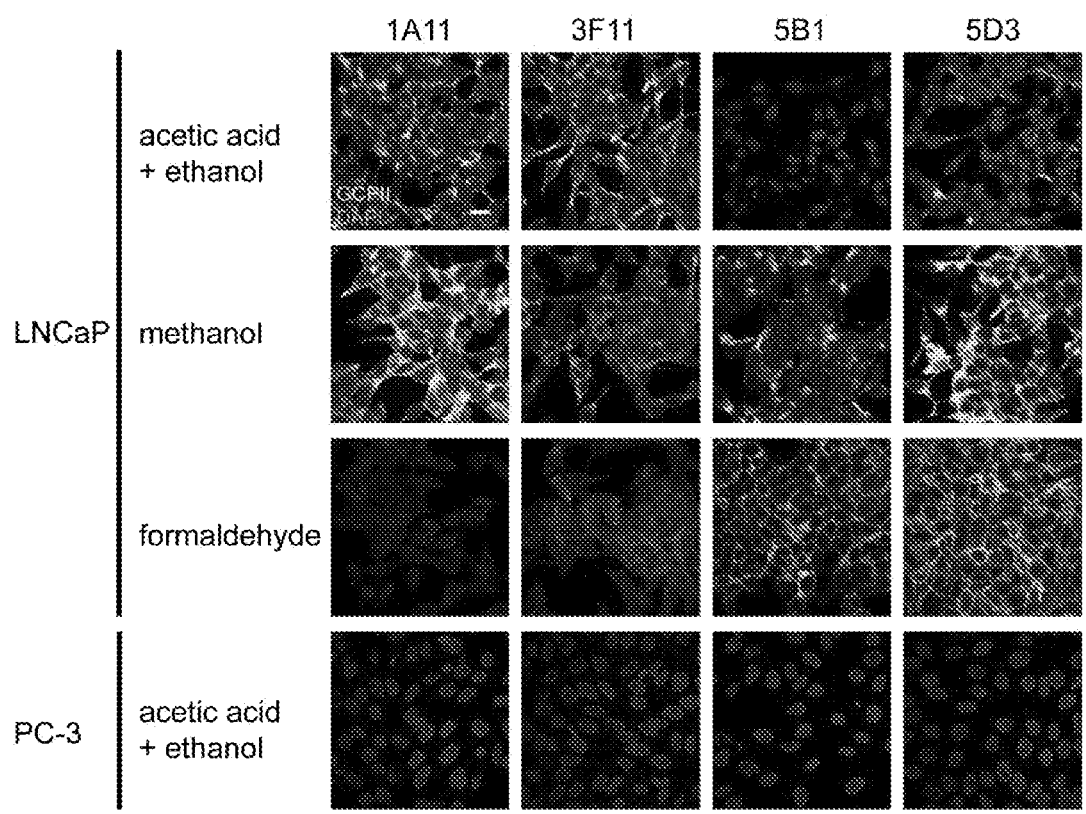
Figure 8A:
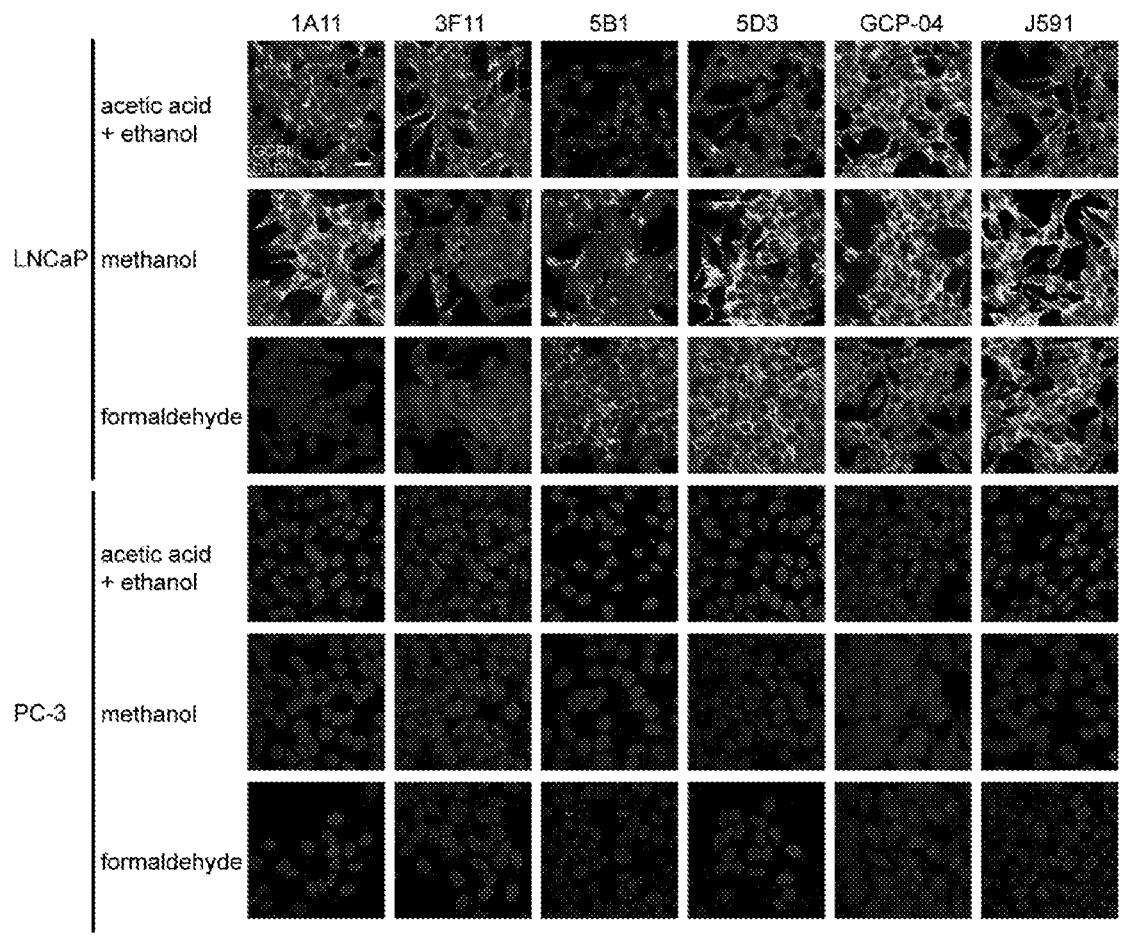
Figure 8B:
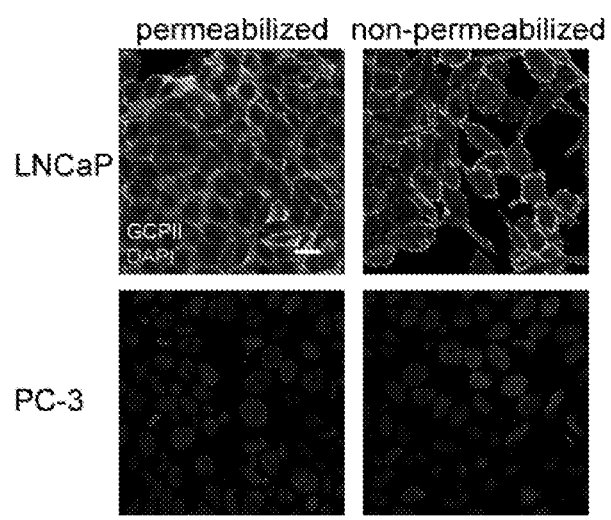
Figure 9:
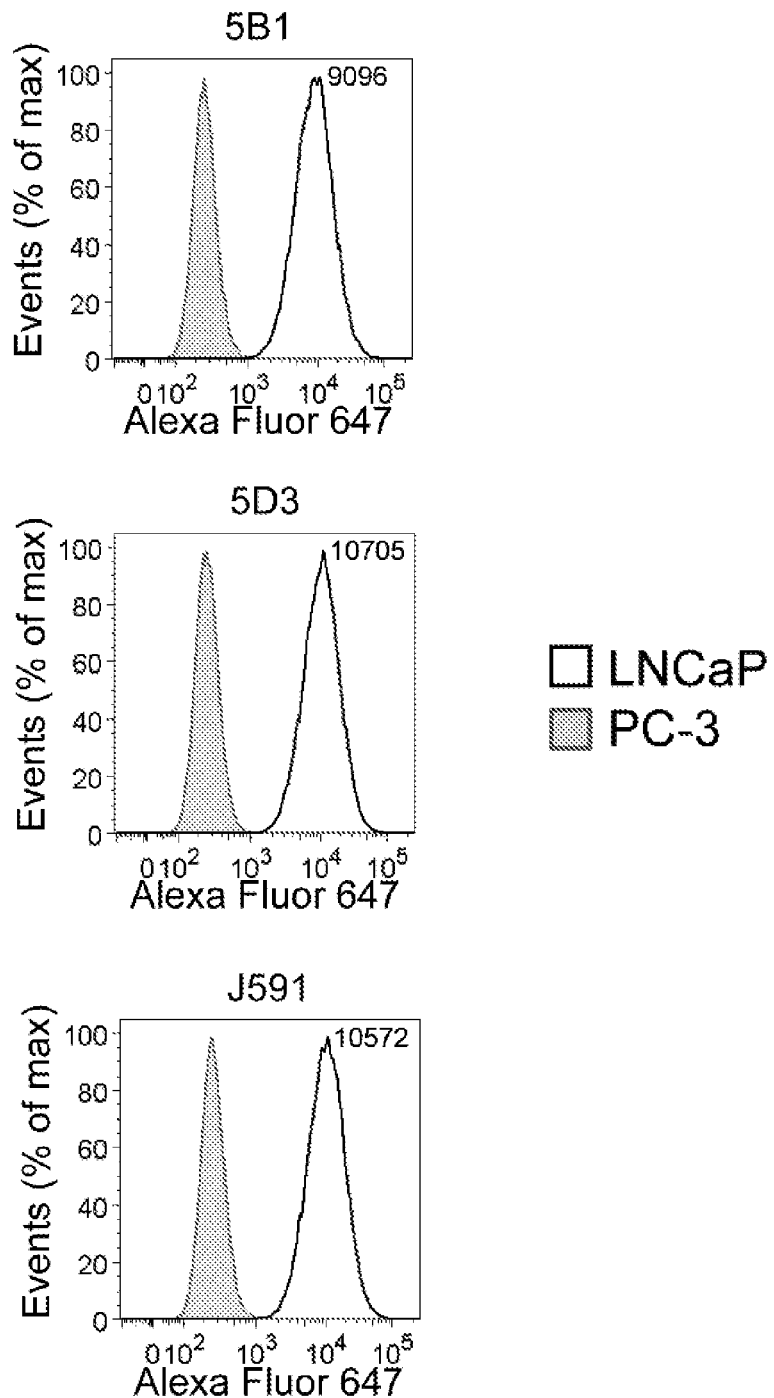
Figure 10A:
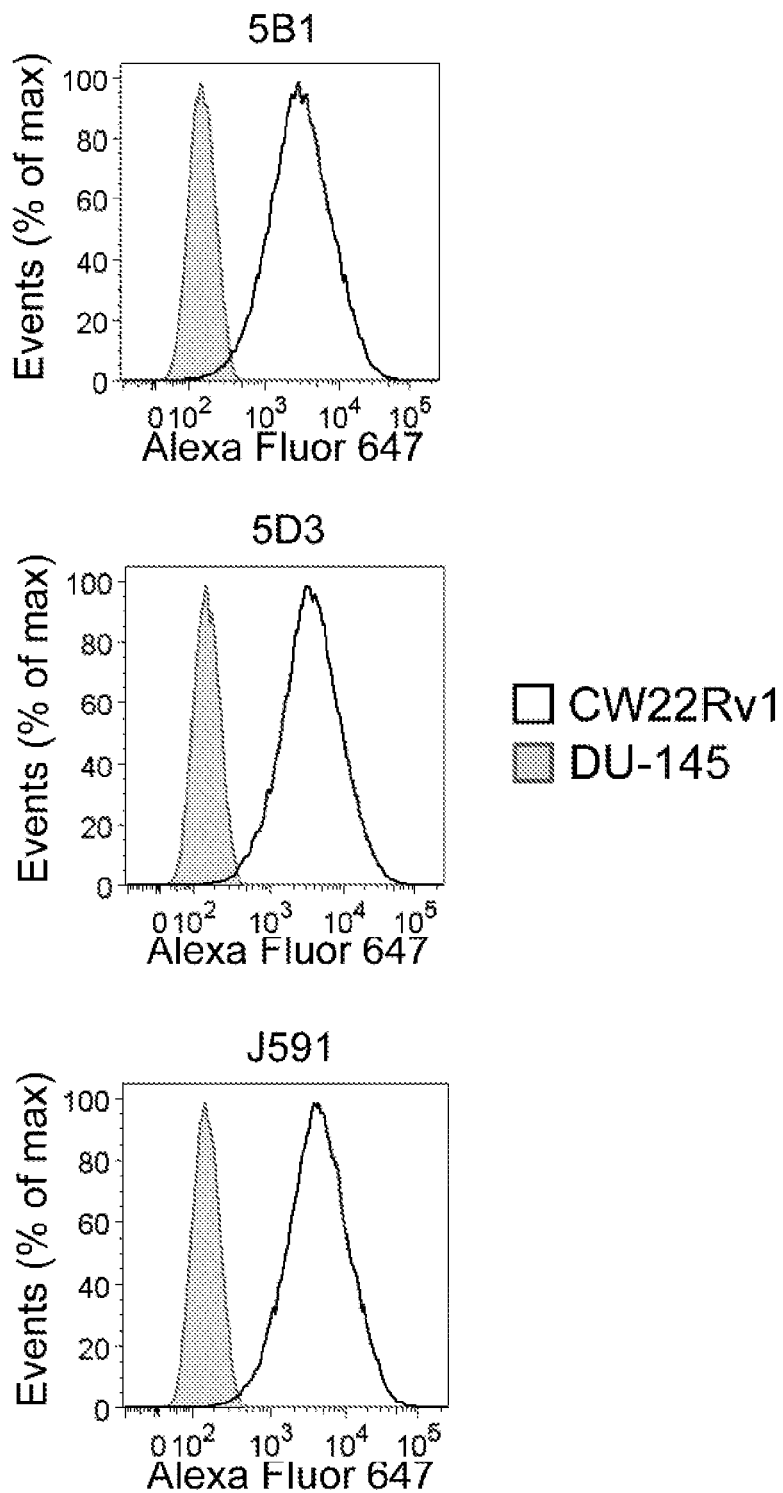
Figure 10B:
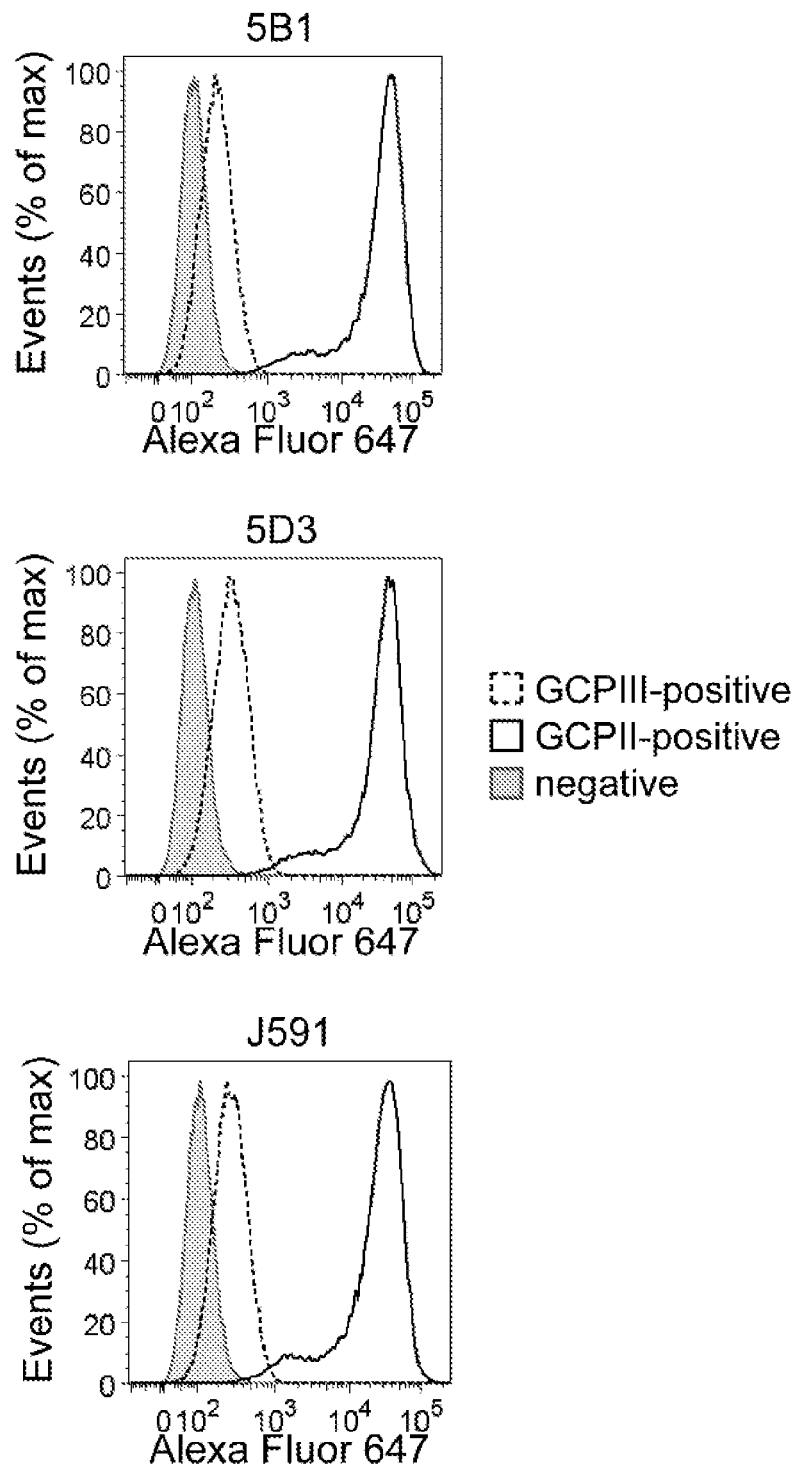
Figure 10C:
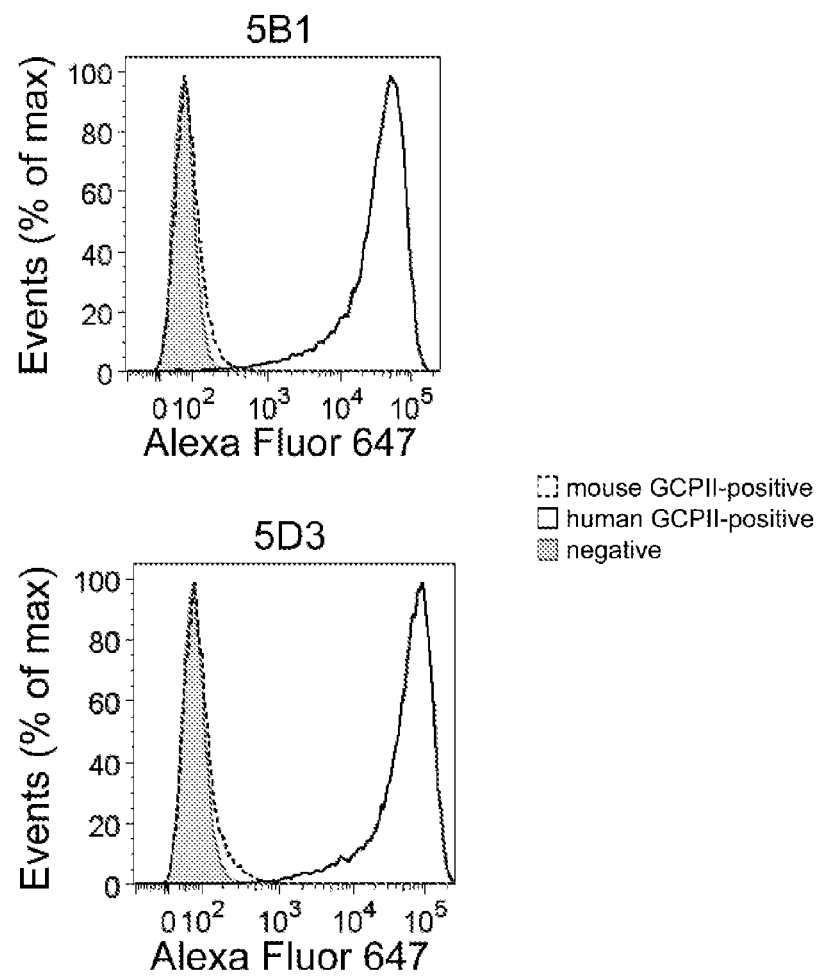
Figure 11A:
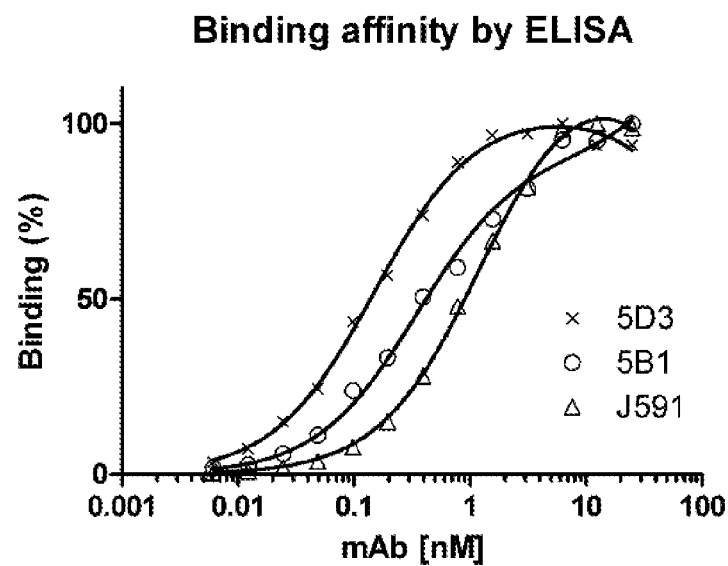
Figure 11B:
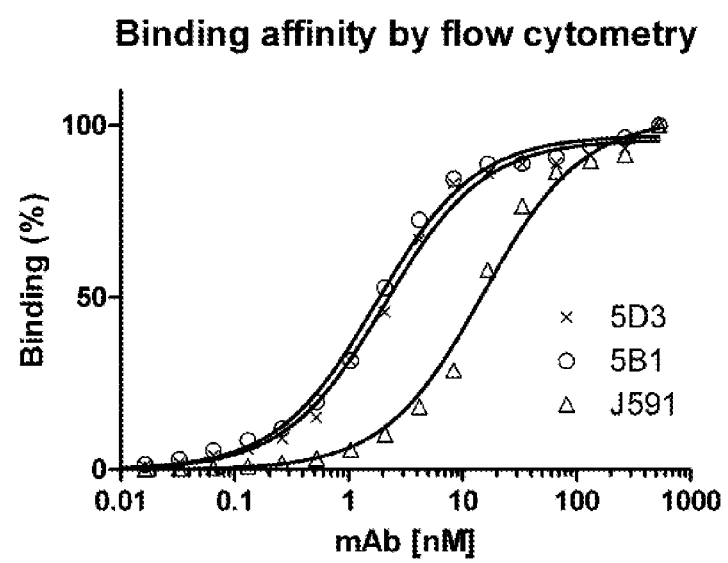
Figure 11C:
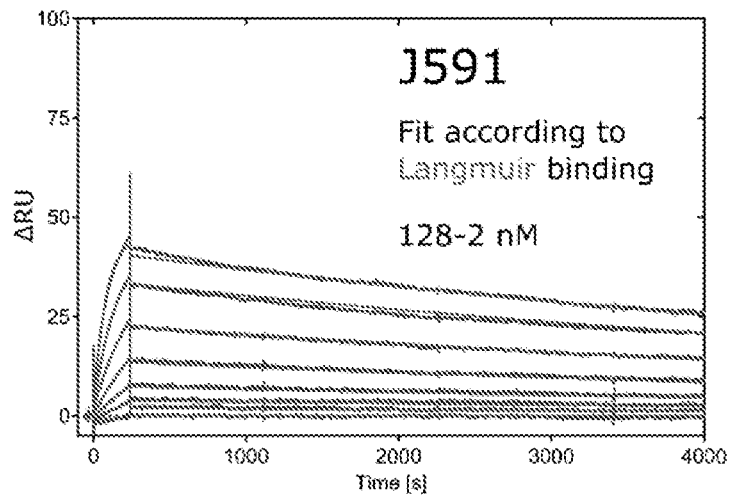
Figure 11D:
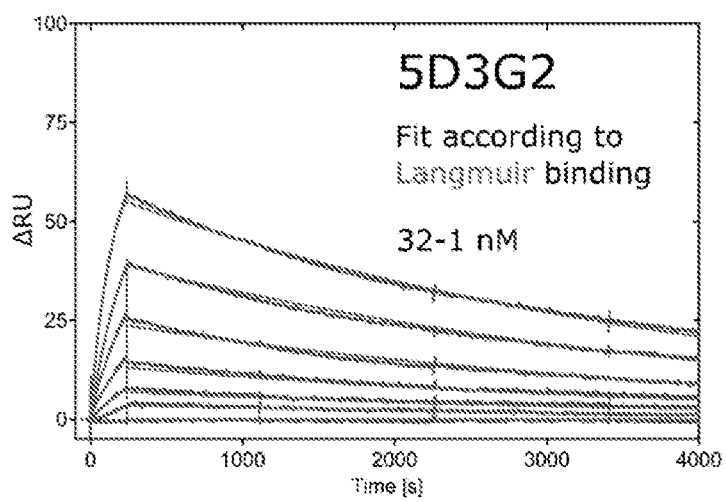
Figure 11E:
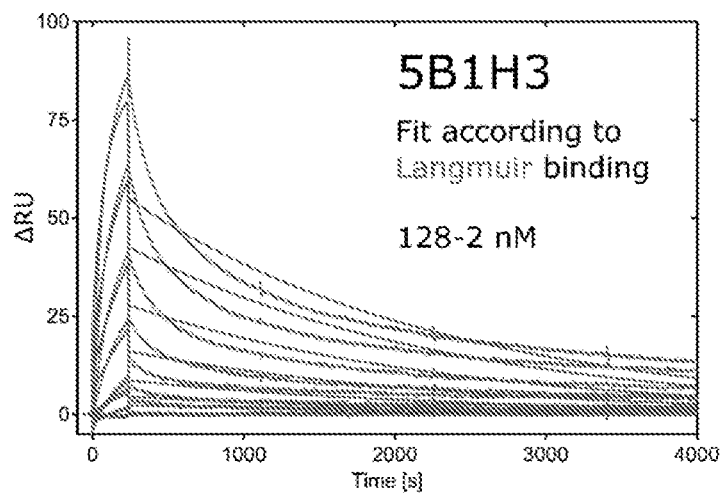
Figure 11F:
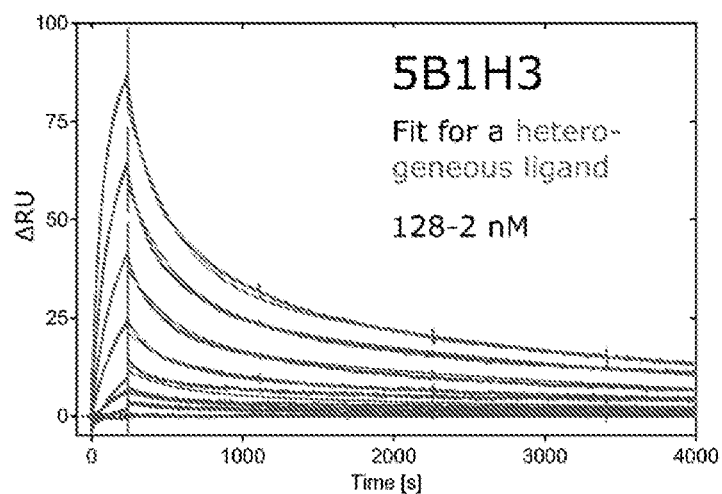
Figure 12A:
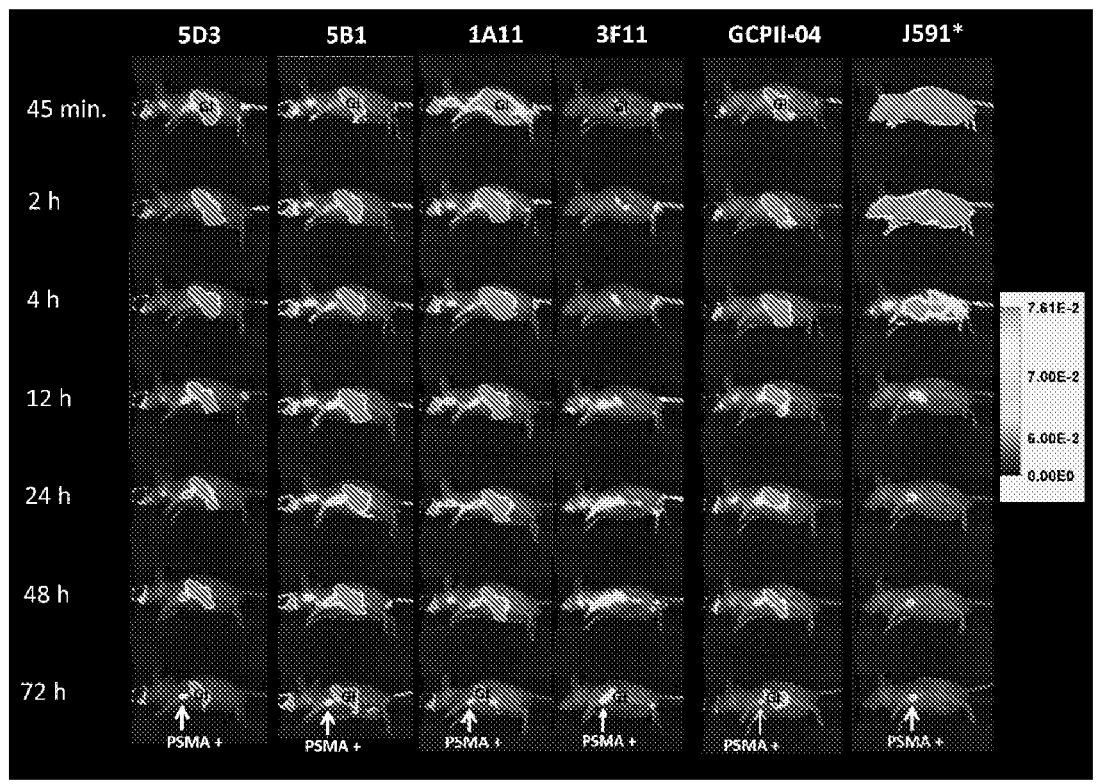
Figure 12B:
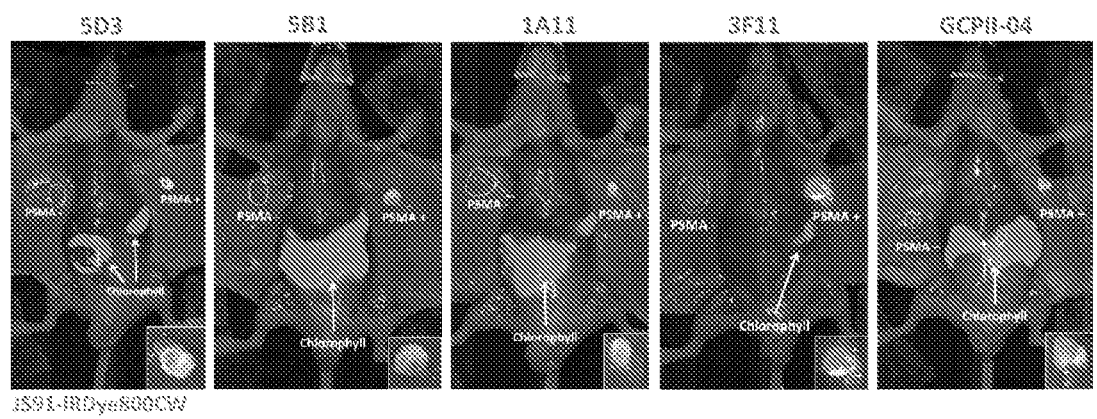
Figures 13G, 13H:
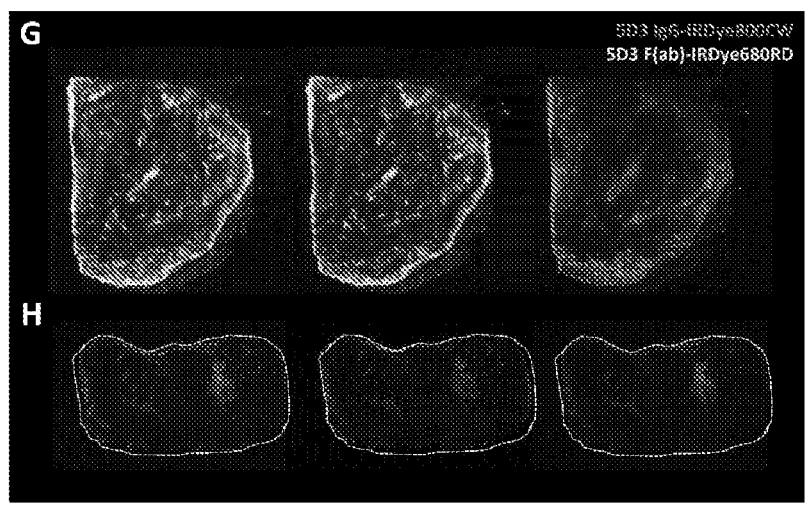

Having thus described the presently disclosed subject matter in general terms, reference will now be made to the accompanying Figures, which are not necessarily drawn to scale, and wherein:

FIG. 1 shows amino acid sequences of the 5B1 mAb and nucleotide sequences of the VL-CL domain and the VH-CH1 domain of the 5B1 mAb;

FIG. 2 shows amino acid sequences of the 5D3 mAb and nucleotide sequences of the VL-CL domain and the VH-CH1 domain of the 5D3 mAb; the VH domain amino acid sequence is provided by SEQ ID NO: 21 and the VL domain amino acid sequence is provided by SEQ ID NO: 22;

FIG. 3A and FIG. 3B show purity and homogeneity of studied mAbs determined by SDS-PAGE (FIG. 3A) and size-exclusion chromatography (FIG. 3B): FIG. 3A shows purified mAbs (1 µg per lane) in a non-reducing (lanes 1-6) and reducing (lanes 8-12) sample buffer separated by SDS-PAGE using a gradient 4-12% gel and stained with Coomassie Blue; and FIG. 3B shows elution profiles from a SUPERDEX HR200 size-exclusion column documenting monodispersity of mAb preparations;

FIG. 4 shows immunoprecipitation of rhPSMA by individual mAbs. mAbs were captured on magnetic Protein G DYNABEADS and the beads used to immunoprecipitate rhPSMA. Captured proteins were eluted from beads with 50 mM glycine, pH 2.8, and eluates analyzed by Coomassie Blue-stained SDS-PAGE. Sample legend: 1. MWM; lines 2-7: rhPSMA input (supernatant following mixing rhPSMA with mAbs-loaded Protein G DYNABEADS); lines 8-13: rhPSMA/mAb complexes released from beads by acidic elution. It was noted that only 5B1, 5D3 and J591 could immunoprecipitate rhPSMA from the solution;

FIG. 5A and FIG. 5B show epitope mapping and mAb Western blotting: FIG. 5A shows alignment of the epitopes on PSMA from different species recognized by the mAbs 3F11 and 1A11 as revealed by peptide scanning and FIG. 5B shows purified ectodomains of human PSMA and several orthologs/paralogs. Conditioned media of corresponding cell cultures, as well as cell lysates were separated by reducing 10% SDS-PAGE, electrotransferred onto a PVDF membrane and probed with individual mAbs. Lanes: 1. human PSMA-overexpressing HEK293T/17 lysate (0.5 µg); 2. GCPIII overexpressing HEK293T/17 lysate (50 µg); 3. HEK293T/17 lysate (50 µg); 4. LNCaP lysate (30 µg); 5. CW22Rv lysate (30 µg); 6. PC-3 lysate (50 µg); 7. human PSMA (10 ng); 8. human PSMA (2 ng); 9. human GCPIII (40 ng); 10. human GCPIII (8 ng); 11. mouse PSMA (10 ng); 12. mouse GCPIII (conditioned medium; 15 µL); 13. Rat PSMA (conditioned medium; 1.5 µL); and 14. pig PSMA (conditioned medium; 1 µL);

FIG. 6 shows complete Western blots developed using individual mAbs. Purified proteins, conditioned media and cell lysates were separated by reducing 10% SDS-PAGE, electrotransferred onto a PVDF membrane and detected using individual mAbs. Sample legend: 1. human PSMA-overexpressing HEK293T/17 lysate (0.5 µg); 2. GCPIII overexpressing HEK293T/17 lysate (50 µg); 3. HEK293T/17 lysate (50 µg); 4. LNCaP lysate (30 µg); 5. CW22Rv lysate (30 µg); 6. PC-3 lysate (50 µg); 7. human PSMA (10 ng); 8. human PSMA (2 ng); 9. human GCPIII (40 ng); 10. human GCPIII (8 ng); 11. mouse PSMA (10 ng); 12. mouse GCPIII conditioned (15 µL); 13. Rat PSMA conditioned lysate (1.5 µL); and 14. pig PSMA conditioned lysate (1 µL);

FIG. 7 shows PSMA detection on LNCaP (PSMA-positive) and PC3 (PSMA-negative) cell lines by immunofluorescence microscopy. Individual cell lines were fixed on glass coverslips using three different fixation protocols and probed with tested mAbs (20 µg/ml), followed by detection with a secondary antibody conjugated with ALEXA FLUOR 488 (green channel). Under these varying conditions, distinct intensities of both cytoplasmic and plasma membrane staining were observed on LNCaP cells. The PSMA-negative PC-3 prostate cell line revealed no staining (cells fixed by acetic acid+ethanol are shown as an example). Nuclei were visualized with DAPI (blue channel); bar: 20 µm;

FIG. 8A and FIG. 8B show immunofluorescence detection of endogenous human PSMA protein in fixed cells: FIG. 8A shows LNCaP (PSMA⁺) and PC-3 (PSMA⁻) cell lines fixed on glass coverslips using three different fixation protocols and probed with a given primary antibody (20 µg/ml), followed by the detection with a secondary antibody conjugated with ALEXA FLUOR 488 (green channel). 1A11 and 3F11 preferentially detect PSMA protein denatured by alcohol-based fixations, while 5B1 and 5D3 are preferably used together with methanol-fixed (5D3) and formaldehyde-fixed cells (5D3 and 5B1). Staining with J591 and GCP-04 is shown for comparison. PSMA-negative PC-3 prostate cell line revealed no staining: FIG. 8B shows that antibodies detect cell surfaced, as well as intracellularly localized PSMA protein in cells fixed by formaldehyde and permeabilized by TRITON X-100 (5B1 shown). Only PSMA protein anchored on the cell surface was detected when cells were not permeabilized prior incubation with antibodies. Nuclei were visualized with DAPI (blue channel); scale bar 20 µm;

FIG. 9 shows flow cytometry analysis of PSMA expression on live cells. Specificity and labeling intensity of the mAbs 5D3 and 5B1 were compared to J591 using LNCaP (PSMA-positive) and PC3 (PSMA-negative) cell lines of prostate origin. Harvested cells were incubated with 5 µg/mL of individual mAb and binding detected by a secondary antibody conjugated to ALEXA FLUOR 647 using an LSRII flow cytometer. A minimum of 30,000 cells were analyzed for each sample using FLOWJO software. While staining on PC3 cells was negative, staining profiles on LNCaP cells suggest comparable performance for all three mAbs tested. According to the indicated median fluorescence values, 5D3 revealed the strongest binding activity toward PSMA protein on LNCaP cells;

FIG. 10A, FIG. 10B, and FIG. 10C show flow cytometry analysis of mAb specificity to human PSMA, human GCPIII and mouse PSMA on live cells: FIG. 10A shows lower endogenous expression of PSMA as compared to in LNCaP cells. Specificity of mAbs for human PSMA was verified using the CW22Rv1 cell line. DU-145 cells were used as a negative control; FIG. 10B shows a comparison of staining intensity for human PSMA and GCPIII. Staining intensity of 5D3, 5B1 and J591 for human PSMA and GCPIII was evaluated using HEK293T cells stably expressing human PSMA/GCPIII at similar levels. Substantially weaker staining intensity was noted for GCPIII; and FIG. 10C shows that 5D3 and 5B1 mAbs do not recognize mouse PSMA on the surface on stably transfected HEK293T cells. In all experiments, harvested cells were incubated with 5 µg/mL of individual mAb and binding detected by a secondary antibody conjugated to ALEXA FLUOR 647 using the LSRII flow cytometer. A minimum of 30,000 cells were analyzed for each sample using FLOWJO software;

FIG. 11A, FIG. 11B, FIG. 11C, FIG. 11D, FIG. 11E, and FIG. 11F show the affinity of the mAbs 5B1 and 5D3 for PSMA determined by ELISA, flow cytometry and surface-plasmon resonance: FIG. 11A shows chemiluminiscence signal plotted against mAb concentration. For direct ELISA, a 384-well MAXISORP plate was coated with streptavidin and loaded with N-terminally biotinylated Avi-PSMA. mAbs were applied in 2-fold dilution series and binding was detected by a secondary antibody conjugated to horseradish peroxidase. The resulting chemiluminiscence signal was plotted against the mAb concentration and data were analyzed by curve fitting with GRAPHPAD; FIG. 11B shows fluorescence signals plotted against mAb concentration. LNCaP cells were incubated with two-fold dilution series of tested mAbs and binding was detected by a secondary antibody conjugated to ALEXA FLUOR 647 using a LSRII flow cytometer. Fluorescence signals were plotted against the mAb concentration and data were analyzed by curve fitting with GRAPHPAD; FIG. 11C, FIG. 11D, FIG. 11E, and FIG. 11F show real-time SPR measurement for individual mAbs determined using a BIACORE 2000 instrument. A CMS sensorchip was amino-coupled with a Fc-specific capture antibody and ~Δ80 RU of the respective mAb was immobilized. Application of rhPSMA in a dilution series resulted in sensograms which were fitted to a Langmuir 1:1 binding model for 5D3 (FIG. 11C) and J591 (FIG. 11D). In contrast, 5B1 clearly showed biphasic dissociation, not in agreement with the Langmuir model (FIG. 11E), but suggesting a heterogeneous analyte (FIG. 11F);

FIG. 12A and FIG. 12B show pharmacokinetics of new anti-PSMA mAbs compared with J591 and ex vivo NIRF imaging showing tumor specificity: FIG. 12 A shows that representative mice, each bearing a PSMA-positive and PSMA-negative (not depicted in views shown) xenograft, was co-injected with the indicated IRDye680RD-labeled mAb (designated in the top row) and J591-IRDye800CW. Images collected at various times post-injection at the 710 nm peak emission (except for J591, asterisk) were normalized to the same exposure time. All mAbs bound to the PSMA-positive tumor as detectable 12 h post-injection and were cleared from non-target sites by 72 h. 3F11 displayed particularly low uptake overall while 5D3 and 5B1 both showed high tumor uptake with 5D3 displaying the highest tumor signal, as well as non-target tissue clearance by 48 h, similar to J591. Autofluorescence due to dietary chlorophyll was observed across the gastrointestinal (GI) tract. As J591 was imaged at 800 nm, autofluorescence was not detected in this case; and FIG. 12B shows each mouse shown from panel A after the 72 h data point. The ventral skin was removed to reduce attenuation and reveal both tumors. The IRDye680RD-labeled antibody studied is displayed in red at the top of each image. Each antibody was co-injected with J591-IRDye800CW, displayed in green; hence, yellow denotes co-localization of J591 uptake (green) with the indicated mAb (red) tested in each mouse. Panels at the lower right show an enlargement of the PSMA-positive tumor. Notably, all antibodies tested except 3F11 displayed specificity for the PSMA-positive PC3 PIP tumor versus the antigen-negative tumor. 5D3 and 5B1 both showed mostly yellow/orange co-localization with J591 while 1A11 showed more heterogeneous tumor uptake. The mAb GCPII-04, which binds to a cytoplasmic epitope of PSMA, also displayed a more heterogeneous binding pattern compared with J591; and FIG. 13A, FIG. 13B, FIG. 13C, FIG. 13D, FIG. 13E, FIG. 13F, FIG. 13G, and FIG. 13H show in vivo pharmacokinetics and ex vivo high resolution NIRF imaging (tumor sections) of the 5D3 IgG and Fab fragment. FIG. 13A, FIG. 13B, FIG. 13C, FIG. 13D, FIG. 13E, and FIG. 13F: A mouse was co-injected with the IgG-IRDye800CW (FIG. 13A) and the Fab-IRDye680RD (FIG. 13B) with overlay shown in FIG. 13C, where IgG is displayed in green and the Fab is displayed in red. FIG. 13A shows that high tumor contrast is achieved 12 h post-injection and by 24 h the whole-mouse background uptake is also low; FIG. 13B shows that high tumor contrast is achieved 2 h post-injection [gastrointestinal (GI) signal is chlorophyll] and continues till 48 h post-injection]; the overlay in FIG. 13C shows a high degree of co-localization from 12 h onwards; FIG. 13D and FIG. 13E show the 72 h uptake without skin of the Fab and IgG, respectively. Both are selective for the PSMA-positive tumor at 72 h; FIG. 13F reveals largely yellow co-localization of both antibody formats within the PSMA-positive tumor; for FIG. 13G and FIG. 13H, PSMA-positive PC-3 PIP and PSMA-negative PC3 flu tumors were harvested following imaging, sectioned and scanned to detect the high-resolution distribution of IgG-IRDye800CW and Fab-IRDye680RD within the tumors; FIG. 13G shows a section of the PSMA-positive PC3 PIP tumor where green depicts IgG, red depicts Fab and yellow shows co-localized IgG and Fab in the leftmost section; and FIG. 13H shows the same, but in sections of PSMA-negative PC3 flu tumor (dotted lines). In the PSMA-positive section, IgG uptake (green) appears more confined to the tumor rim and small focal regions near the rim while the Fab (red) appears to display a wider uptake pattern both away from the rim and within tumor.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Prostate-specific membrane antigen (PSMA) is a validated target for the imaging and therapy of prostate cancer. The presently disclosed mAbs reveal high specificity and affinity for native PSMA, and have significantly higher affinity for PSMA than the best second-generation mAb J591 that has been clinically validated for in vivo imaging of PSMA. Accordingly, the presently disclosed mAbs are prime candidates for the development of next-generation theranostics targeting PSMA.

I. Isolated Antibodies

The presently disclosed subject matter provides antibodies, or fragments or derivatives thereof that can be used for imaging or therapy of PSMA-expressing cancer cells, such as prostate cancer cells.

In some embodiments, the presently disclosed subject matter provides an isolated antibody, antibody fragment, or derivative thereof that specifically binds prostate specific membrane antigen (PSMA) and comprises a protein sequence at least 80%, at least 85%, at least 90%, at least 91%, at least 92%, at least 93%, at least 94%, at least 95%, at least 96%, at least 97%, at least 98%, at least 99% identical, or at least 100% identical to any one of SEQ ID NOs:1, 2, 6, and 7. In some embodiments, the presently disclosed subject matter provides an isolated antibody, antibody fragment, or derivative thereof that specifically binds prostate specific membrane antigen (PSMA) and comprises a protein sequence at least 80% identical to any one of SEQ ID NOs:1, 2, 6, and 7. In some embodiments, the presently disclosed subject matter provides an isolated antibody, antibody fragment, or derivative thereof that specifically binds prostate specific membrane antigen (PSMA) and comprises a protein sequence at least 90% identical to any one of SEQ ID NOs:1, 2, 6, and 7. In some embodiments, the antibody, antibody fragment, or derivative thereof comprises a protein sequence which is 100% identical to any one of SEQ ID NOs:1, 2, 6, and 7. In some embodiments, the isolated antibody, antibody fragment, or derivative thereof is a monoclonal antibody, antibody fragment, or derivative thereof.

"Sequence identity" or "identity" in the context of proteins or polypeptides refers to the amino acid residues in two amino acid sequences that are the same when aligned for maximum correspondence over a specified comparison window. Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MEGALIGN program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) *CABIOS* 5:151-153; Higgins et al. (1992) *Comput. Appl. Biosci.* 8:189-191) and found in the MEGALIGN program of the LASERGENE bioinformatics computing suite (DNASTAR Inc., Madison, Wis.).

In some embodiments, the antibody, antibody fragment, or derivative thereof comprises a VL-CL domain that comprises a protein sequence that is at least 90% identical to SEQ ID NO:1 and a VH-CH1 domain that comprises a protein sequence that is at least 90% identical to SEQ ID NO:2. In some embodiments, the antibody, antibody fragment, or derivative thereof comprises a VL-CL domain that comprises a protein sequence that is 100% identical to SEQ ID NO:1 and a VH-CH1 domain that comprises a protein sequence that is 100% identical to SEQ ID NO:2.

In some embodiments, the antibody, antibody fragment, or derivative thereof comprises a VL-CL domain that comprises a protein sequence that is at least 90% identical to SEQ ID NO:6 and a VH-CH1 domain that comprises a protein sequence that is at least 90% identical to SEQ ID NO:7. In some embodiments, the antibody, antibody fragment, or derivative thereof comprises a VL-CL domain that comprises a protein sequence that is 100% identical to SEQ ID NO:6 and a VH-CH1 domain that comprises a protein sequence that is 100% identical to SEQ ID NO:7.

In some embodiments, the antibody, antibody fragment, or derivative thereof comprises a VL domain that comprises a protein sequence that is at least 90% identical to the VL domain shown in SEQ ID NO:1 or SEQ ID NO:6. In some embodiments, the antibody, antibody fragment, or derivative thereof comprises a VL domain that comprises a protein sequence that is 100% identical to the VL domain shown in SEQ ID NO:1 or SEQ ID NO:6. In some embodiments, the antibody, antibody fragment, or derivative thereof comprises a CL domain that comprises a protein sequence that is at least 90% identical to the CL domain shown in SEQ ID NO:1 or SEQ ID NO:6. In some embodiments, the antibody, antibody fragment, or derivative thereof comprises a CL domain that comprises a protein sequence that is 100% identical to the CL domain shown in SEQ ID NO:1 or SEQ ID NO:6.

In some embodiments, the antibody, antibody fragment, or derivative thereof comprises a VH domain that comprises a protein sequence that is at least 90% identical to the VH domain shown in SEQ ID NO:2 or SEQ ID NO:7. In some embodiments, the antibody, antibody fragment, or derivative thereof comprises a VH domain that comprises a protein sequence that is 100% identical to the VH domain shown in SEQ ID NO:2 or SEQ ID NO:7. In some embodiments, the antibody, antibody fragment, or derivative thereof comprises a CH1 domain that comprises a protein sequence that is at least 90% identical to the CH1 domain shown in SEQ ID NO:2 or SEQ ID NO:7. In some embodiments, the antibody, antibody fragment, or derivative thereof comprises a CH1 domain that comprises a protein sequence that is 100% identical to the CH1 domain shown in SEQ ID NO:2 or SEQ ID NO:7.

In some embodiments, the antibody fragment or derivative thereof is a Fab-fragment, a F(ab$_2$)'-fragment, a single-chain antibody, a chimeric antibody, a CDR-grafted antibody, a bivalent antibody-construct, a humanized antibody, a human, a synthetic antibody, or a chemically modified derivative thereof, a multispecific antibody, a diabody, a Fv-fragment, or another type of a recombinant antibody.

In particular embodiments, the antibody, fragment, or derivative thereof is a chimeric antibody. In such embodiments, for example, in the case of a chimeric Fab fragment, the antibody comprises a protein sequence that is only approximately 50% identical to any one of SEQ ID Nos. 1, 2, 6 and 7.

Fragments or derivatives of the presently disclosed antibodies directed to at least one epitope of PSMA can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIACORE system can be used to increase the efficiency of phage antibodies which bind to at least one epitope of PSMA (Schier, Human Antibodies Hybridomas 7 (1996), 97-105; Malmborg, J. Immunol. Methods 183 (1995), 7-13).

The presently disclosed subject matter contemplates using nucleic acid molecules, vectors and host cells to produce mutated PSMA antibodies. The antibodies may be mutated in the variable domains of the heavy and/or light chains to alter a binding property of the antibody. For example, a mutation may be made in one or more of the CDR regions to increase or decrease the Kd of the antibody for PSMA, or to alter the binding specificity of the antibody. Techniques in site directed mutagenesis are well-known in the art. See, e.g., Sambrook et al. and Ausubel et al., supra. Furthermore, mutations are made at an amino acid residue that is known to be changed compared to germline in a variable region of a PSMA antibody. In another aspect, the nucleic acid molecules are mutated in one or more of the framework regions. A mutation may be made in a framework region or constant domain to increase the half-life of the PSMA antibody. See, e.g., WO 00/09560, published Feb. 24, 2000. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

The production of chimeric antibodies is described, for example, in WO89/09622. Methods for the production of humanized antibodies are described in, e.g., EP-A1 0 239 400 and WO90/07861. A further source of antibodies to be utilized in accordance with the presently disclosed subject matter are so-called xenogenic antibodies. The general principle for the production of xenogenic antibodies, such as human antibodies in mice is described in, e.g., WO 91/10741, WO 94/02602, WO 96/34096 and WO 96/33735. As discussed above, the antibody of the presently disclosed subject matter may exist in a variety of forms besides complete antibodies; including, for example, Fv, Fab and F(ab)2, as well as in single chains; see e.g., WO88/09344.

Aspects of the presently disclosed subject matter relate to a nucleic acid molecule encoding the antibody, antibody fragment or derivative thereof. As used interchangeably herein, the terms "nucleic acids," "oligonucleotides," and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT Patent App. Pub. No. WO 95/04064. The polynucleotide sequences of the presently disclosed subject matter may be prepared by any known method, including synthetic, recombinant, ex vivo generation, or a combination thereof, as well as utilizing any purification methods known in the art.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. The term "polypeptide" or "protein" as used herein refers to a molecule comprising a string of at least three amino acids linked together by peptide bonds. The terms "protein" and "polypeptide" may be used interchangeably. Proteins may be recombinant or naturally derived.

Nucleic acid molecules encoding an antibody, antibody fragment or derivative thereof may be, e.g., DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions.

The presently disclosed subject matter also relates to a vector comprising a nucleic acid molecule described herein. Said vector may be, for example, a phage, plasmid, viral or retroviral vector. Retroviral vectors may be replication competent or replication defective. In the latter case, viral propagation generally will occur only in complementing host cells.

The nucleic acid molecules described herein may be joined to a vector containing selectable markers for propagation in a host cell. Generally, a plasmid vector is introduced in a precipitate, such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

In some embodiments, the vector is an expression vector wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional, as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOXI or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art, such as Okayama-Berg cDNA expression vector pcDV1 (PHARMACIA), pCDM8, pRc/CMV, pcDNA1, pcDNA3 (INVITROGEN), pSPORTI (GIBCO BRL). Preferably, said vector is an expression vector and/or a gene transfer or targeting vector. Expression vectors derived from viruses, such as retroviruses, vaccinia virus, adenoassociated virus, herpes viruses, or bovine papilloma virus, may be used for delivery of the polynucleotides or vector of the presently disclosed subject matter into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001, Third Edition) N.Y. and Ausubel, Current Protocols in Molecular Biology, Green Publishing Associates and Wiley Interscience, N.Y. (1994). Alternatively, the nucleic acid molecules of the presently disclosed subject matter can be reconstituted into liposomes for delivery to target cells.

The presently disclosed subject matter further relates to a host cell comprising a vector of the presently disclosed subject matter. Said host cell may be a prokaryotic or eukaryotic cell. The polynucleotide or vector of the presently disclosed subject matter which is present in the host cell may either be integrated into the genome of the host cell or it may be maintained extrachromosomally. In this respect, it is also to be understood that the nucleic acid molecule of the presently disclosed subject matter can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host cell can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the presently disclosed subject matter. Prokaryotic host cells may include gram negative, as well as gram positive bacteria, such as, for example, *E. coli, S. typhimurium, Serratia marcescens* and *Bacillus subtilis*. A polynucleotide coding for a mutant form of variant polypeptides of the presently disclosed subject matter can be used to transform or transfect the host cell using any of the techniques commonly known to those of ordinary skill in the art. Methods for preparing fused, operably linked genes and expressing them in bacteria or animal cells are well-known in the art (Sambrook, Molecular Cloning A Laboratory Manual, Cold Spring Harbor Laboratory (2001, Third Edition). The genetic constructs and methods described therein can be utilized for expression of variant antibodies, antibody fragments or derivatives thereof of the presently disclosed subject matter in, e.g., prokaryotic host cells. In general, expression vectors containing promoter sequences which facilitate the efficient transcription of the inserted nucleic acid molecule are used in connection with the host cell. The expression vector typically contains an origin of replication, a promoter, and a terminator, as well as specific genes which are capable of providing phenotypic selection of the transformed cells. The transformed prokaryotic host cells can be grown in fermentors and cultured according to techniques known in the art to achieve optimal cell growth. The antibodies, antibody fragments or derivatives thereof of the presently disclosed subject matter can then be isolated from the grown medium, cellular lysates, or cellular membrane fractions. The isolation and purification of the microbially or otherwise expressed antibodies, antibody fragments or derivatives thereof of the presently disclosed subject matter may be by any conventional means, such as, for example, preparative chromatographic separations and immunological separations, such as those involving the use of monoclonal or polyclonal antibodies.

In some embodiments, the host cell is a bacteria, fungal, plant, amphibian or animal cell. Animal cells include, but are not limited to, Chinese hamster ovary (CHO) cells, baby hamster kidney (BHK) cells, monkey kidney cells (COS), 3T3 cells, NSO cells, and a number of other cell lines.

In some embodiments, the host cell is an insect cell. Insect cells include, but are not limited to, cells of the SF9 cell lines. In some embodiments, the host cell is a human cell or human cell line. Said human cells include, but are not limited to Human embryonic kidney cells (HEK293, 293T, 293 freestyle). Furthermore, said human cell lines include, but are not limited to HeLa cells, human hepatocellular carcinoma cells (e.g., Hep G2), A549 cells.

It is likely that antibodies expressed by different cell lines or in transgenic animals will have different glycosylation status. However, all antibodies encoded by the nucleic acid molecules provided herein, or comprising the amino acid sequences provided herein are part of the presently disclosed subject matter, regardless of the glycosylation status of the antibodies.

The presently disclosed subject matter also provides transgenic non-human animals comprising one or more nucleic acid molecules of the presently disclosed subject matter that may be used to produce an antibody, antibody fragment, or derivative thereof of the presently disclosed subject matter. Antibodies can be produced in and recovered from tissue or body fluids, such as milk, blood or urine, of goats, cows, horses, pigs, rats, mice, rabbits, hamsters or other mammals. See, e.g., U.S. Pat. Nos. 5,827,690, 5,756, 687, 5,750,172, and 5,741,957. As described above, non-human transgenic animals that comprise human immunoglobulin loci can be produced by immunizing with PSMA or a portion thereof.

Aspects of the presently disclosed subject matter relate to a method for the preparation of an antibody, antibody fragment or derivative thereof, comprising culturing a host cell of the presently disclosed subject matter under conditions that allow synthesis of said antibody, antibody fragment or derivative thereof and recovering said antibody, antibody fragment or derivative thereof from said culture.

The transformed host cells can be grown in fermentors and cultured according to techniques known in the art to achieve optimal cell growth. Once expressed, the whole antibodies, their dimers, individual light and heavy chains, or other immunoglobulin forms of the presently disclosed subject matter, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the presently disclosed subject matter can then be isolated from the growth medium, cellular lysates, or cellular membrane fractions. The isolation and purification of the, e.g., microbially expressed antibodies or immunoglobulin chains of the presently disclosed subject matter may be by any conventional means, such as, for example, preparative chromatographic separations and immunological separations, such as those involving the use of monoclonal or polyclonal antibodies directed, e.g., against the constant region of the antibody of the presently disclosed subject matter.

In some embodiments, the antibody, antibody fragment, or derivative thereof binds PSMA in its native form. In some embodiments, the binding of PSMA in its native form occurs on the surface of at least one PSMA-expressing cancer cell. As used herein, the term "native form" refers to the form of a molecule, such as a protein, when it is properly folded or assembled.

In some embodiments, the binding of PSMA in its native form by the antibody, antibody fragment, or derivative on the surface of at least one PSMA-expressing cancer cell inhibits survival of at least one PSMA-expressing cancer cell. In some embodiments, the antibody, antibody fragment, or derivative thereof inhibits survival of at least 10%, at least 20%, at least 30%, at least 40%, at least 50%, at least 60%, at least 70%, or at least 75% of PSMA-expressing cancer cells in a bulk tumor (e.g., a prostate tumor, etc.). In some embodiments, the antibody, antibody fragment, or derivative thereof inhibits survival of at least 85%, at least 90%, at least 95%, at least 96%, at least 97%, at least 98%, or at least 99% of PSMA-expressing cancer cells in a bulk tumor (e.g., a prostate tumor, etc.). In some embodiments, the antibody, antibody fragment, or derivative thereof inhibits survival of all PSMA-expressing cancer cells in a bulk tumor (e.g., a prostate tumor, etc.).

The presently disclosed antibodies demonstrate advantageous properties with respect to their binding specificity and biological activity, in particular with respect to their capacity to recognize epitopes of PSMA, and to decrease cell growth. Since the pharmaceutical and/or diagnostic applications of the presently disclosed antibodies include, but are not limited to humans, the presently disclosed subject matter contemplates humanizing antibodies to minimize potential negative immunogenic side effects for use in humans. The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences. In some embodiments, the antibody, fragment, or derivative thereof is a humanized antibody.

It will be apparent to those skilled in the art that the antibodies of the presently disclosed subject matter can be conjugated to other moieties for, e.g., drug targeting and imaging applications. In some embodiments, the antibody, antibody fragment or derivative thereof is conjugated to an effector, such as a radioisotope, a fluorophore, or a toxic chemotherapeutic agent. In some embodiments, the antibody conjugates are useful in targeting cells, e.g., cancer cells, expressing PSMA, for elimination. In some embodiments, the antibody conjugates are useful in diagnosing a PSMA-expressing cancer, such as prostate cancer.

In some embodiments, the antibody, fragment, or derivative thereof is conjugated to at least one agent. In some embodiments the antibody, fragment, or derivative thereof is conjugated to at least two agents. The agent may be a therapeutic agent. The agent may be an imaging agent. The antibody, fragment, or derivative thereof may be conjugated to a therapeutic agent. The antibody, fragment, or derivative thereof may be conjugated to an imaging agent. The antibody, fragment, or derivative thereof may be conjugated to a radionucleotide. The antibody, fragment, or derivative thereof may be conjugated to a fluorophore. The antibody, fragment, or derivative thereof may be conjugated to a therapeutic agent and an imaging agent. The antibody, fragment, or derivative thereof may be conjugated to a radionucleotide and a fluorophore.

Examples of radionucleotides include, but are not limited to, $^{11}$C, $^{13}$N, $^{15}$O, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, $^{89}$Zr, $^{90}$Y, $^{86}$Y, $^{177}$Lu, $^{225}$Ac, $^{213}$Bi, $^{212}$Bi, $^{227}$Th, $^{212}$Ph, $^{115}$In, $^{203}$Ph, $^{60}$Cu, $^{62}$Cu, $^{64}$Cu, $^{223}$Ra, $^{67}$Ga, and $^{68}$Ga. Stable isotopes as controls, may include, but are not limited to, $^{115}$In and $^{203}$Pb, or an $^{18}$F-labeled substrate.

Examples of fluorophores include, but are not limited to, ALEXAFLUOR 350, ALEXAFLUOR 430, ALEXAFLUOR 405, ALEXAFLUOR 488, ALEXAFLUOR 546, ALEXAFLUOR 555, ALEXAFLUOR 594, ALEXAFLUOR 660, ALEXAFLUOR 633, ALEXAFLUOR 647, ALEXAFLUOR 680, ALEXAFLUOR 700, ALEXAFLUOR 750, ALEXAFLUOR 790, AMCA, (BODIPY) dye, or derivatives thereof, including, but not limited to, BODIPY 630/650, BODIPY 650/665, BODIPY 581/591, BODIPY-FL, BODIPY-R6G, BODIPY-TR, BODIPY-TMR, BODIPY-TRX, Cascade Blue, Cy3, Cy5, Cy5.5, Cy7, 6-FAM, fluorescein, Fluorescein Isothiocyanate, TRITC, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, Texas Red, carbocyanine, indocarbocyanine, oxacarbocyanine, thuicarbocyanine, merocyanine, polymethine, coumarine, rhodamine, xanthene, a boron-dipyrromethane VIVOTAG-680, VIVOTAG-S680, VIVOTAG-S750, Dy677, Dy676, Dy682, Dy752, Dy780, DYLIGHT 547, DYLIGHT 647, DYLIGHT 350 (Ex/Em=353 nm/432 nm), DYLIGHT 405 (400/420), DYLIGHT 488 (493/518), DYLIGHT 550 (562/576), DYLIGHT 594 (593/618), DYLIGHT 633 (638/658), DYLIGHT 650 (652/672), DYLIGHT 680 (692/712), DYLIGHT 755 (754/776), DYLIGHT 800 (777/794), and derivatives thereof, including, but not limited to, NHS esters, maleimides, phosphines, and free acids, HILYTE FLUOR 647, HILYTE FLUOR 680, HILYTE FLUOR 750, IR800 (Dimethyl{4-[1,5,5-tris(4-dimethylaminophenyl)-2,4-pentadienylidene]-2,5-cyclohexadien-1-ylidene}ammonium perchlorate), IRDye 800CW, IRDye 800RS, IRDye 700DX, ADS780WS, ADS830WS, ADS832WS, R-Phycoerythrin, FLAMMA 749, FLAMMA 774 and ICG. In some embodiments, the antibody, fragment, or derivative is conjugated to the at least one agent via a linker.

In some embodiments, at least one agent comprises an imaging agent, wherein the imaging agent comprises a radionuclide suitable for use with positron emission tomography (PET) imaging, including, but not limited to, $^{11}$C, $^{13}$N, $^{15}$O, $^{124}$I, $^{18}$F, $^{60}$Cu, $^{62}$Cu, $^{64}$Cu, $^{86}$Y, $^{89}$Zr, and $^{68}$Ga.

In other embodiments, the imagining agent comprises a radionuclide suitable for use with single-photon emission computed tomography (SPECT) imaging, including, but not limited to, $^{123}$I, $^{125}$I, and $^{111}$In.

In some embodiments, stable isotopes, including, but not limited to, $^{115}$In and $^{203}$Pb can be used as controls.

Moreover, the linking of antibodies, antibody fragments, or derivatives thereof of the presently disclosed subject matter to radioisotopes e.g., provides advantages to tumor treatments. Unlike chemotherapy and other conventional forms of cancer treatment, radioimmunotherapy or the administration of a radioisotope-antibody combination directly targets the cancer cells with minimal damage to surrounding normal, healthy tissue.

Accordingly, in particular embodiments, the at least one agent comprises a therapeutic agent. In some embodiments, the therapeutic agent comprises a radionuclide suitable for use in alpha therapy, including, but not limited to $^{211}$At, $^{225}$Ac, $^{213}$Bi, $^{212}$Bi, $^{227}$Th, $^{212}$Pb, and $^{223}$Ra. In other embodiments, the therapeutic agent comprises a radionuclide suitable for use in beta therapy, including, but not limited to $^{90}$Y, $^{177}$Lu, and $^{131}$I. In yet other embodiments, the therapeutic agent comprises a radionuclide suitable for use in Auger therapy, including, but not limited to $^{123}$I, $^{125}$I, $^{111}$In, and $^{67}$Ga.

In some embodiments, the binding of PSMA in its native form by the antibody, antibody fragment, or derivative thereof on the surface of at least one PSMA-expressing cancer cell can be used to image at least one PSMA-expressing cancer cell.

In certain embodiments, the presently disclosed antibody, fragment, or derivative binds PSMA and is suitable for targeting PSMA in its native conformation by techniques, such as (sandwich) ELISA, immunofluorescence, flow cytometry, and immunohistochemistry and in vivo imaging and therapy.

In some embodiments, the antibody, antibody fragment, or derivative thereof is conjugated to at least one agent via a linker. Different linkers that release the drugs under acidic or reducing conditions or upon exposure to specific proteases are employed with this technology. In some embodiments, the linker is a cleavable linker, such as a peptide linker. In some embodiments, the linker is an uncleavable linker, such as a thioether linker.

In some embodiments, the presently disclosed subject matter provides a pharmaceutical composition comprising a presently disclosed antibody, antibody fragment, or derivative thereof. In some embodiments, the presently disclosed subject matter provides a diagnostic composition comprising a presently disclosed antibody, antibody fragment, or derivative thereof.

The term "composition" as employed herein comprises at least one compound of the invention. Preferably, such a composition is a pharmaceutical or a diagnostic composition.

The composition may be in solid, liquid or gaseous form and may be, inter alia, in a form of (a) powder(s), (a) tablet(s), (a) solution(s) or (an) aerosol(s). Said composition may comprise at least two, preferably three, more preferably four, most preferably five compounds of the presently disclosed subject matter or nucleic acid molecules encoding said compounds. Said composition may also comprise optimized antibodies, antibody fragments or derivatives thereof obtainable by the methods of the presently disclosed subject matter.

In some embodiments, the pharmaceutical composition optionally comprises a pharmaceutically acceptable carrier and/or diluent. The herein disclosed pharmaceutical composition may be used for the treatment of a disorder associated with excessive PSMA expression levels and/or activity (e.g., PSMA-expressing or overexpressing diseases (e.g., PSMA-expressing cancers).

The presently disclosed subject matter invention provides for pharmaceutical compositions comprising the compounds of the presently disclosed subject matter to be used for the treatment of diseases/disorders associated with PSMA expression or overexpression.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions of the presently disclosed subject matter may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 µg and 100 mg/kg body weight per dose; however, doses below or above this exemplary range are envisioned, especially considering the aforementioned factors. If the regimen is a continuous infusion, it should also be in the range of 1 µg to 100 mg per kilogram of body weight per minute.

Progress can be monitored by periodic assessment. The compositions of the presently disclosed subject matter may be administered locally or systemically.

Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, anti-oxidants, chelating agents, and inert gases and the like. Furthermore, the pharmaceutical composition of the presently disclosed subject matter may comprise further agents depending on the intended use of the pharmaceutical composition, such as antineoplastic agents, photosensitizing agents, etc.

In some embodiments, when administered in combination, two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In some embodiments, the pharmaceutical composition of the presently disclosed subject matter can also be used for veterinary purposes.

In some embodiments, the presently disclosed subject matter relates to the use of the antibody, antibody fragment or derivative thereof, the nucleic acid molecule, the vector, the host cell of the presently disclosed subject matter, or an antibody, antibody fragment or derivative thereof obtained by the method of the presently disclosed subject matter for the preparation of a pharmaceutical composition for prevention or treatment of a disorder associated with excessive and/or aberrant PSMA expression and/or activity.

In some embodiments, the presently disclosed subject matter provides a diagnostic composition comprising the antibody, antibody fragment or derivative thereof of the presently disclosed subject matter, the nucleic acid molecule, the vector, the host cell of the presently disclosed subject matter, or an antibody, antibody fragment or derivative thereof obtained by the method of the presently disclosed subject matter, and optionally a pharmaceutically acceptable carrier.

The diagnostic composition of the presently disclosed subject matter is useful in the detection of an undesired expression or over-expression of PSMA in different cells, tissues, or samples, comprising contacting a sample with an antibody of the presently disclosed subject matter, and detecting the presence of PSMA in the sample. Accordingly, the diagnostic composition of the presently disclosed subject matter may be used for assessing the onset or the disease status of a PSMA-associated disease. As used herein, "PSMA-associated disease" refers to any disease, condition, or disorder which is correlated directly or indirectly with abnormal levels of expression and/or activity of PSMA. As used herein, "PSMA-expressing cells" refer to those cells that abnormally express PSMA as compared to cells from a subject that does not have a PSMA-associated disease, such as a PSMA-expressing cancer. Furthermore, malignant cells, such as cancer cells expressing PSMA, can be targeted with the antibody, antibody fragment or derivative thereof of the presently disclosed subject matter. The cells which have bound the antibody of the presently disclosed subject matter might thus be attacked by immune system functions, such as the complement system or by cell-mediated cytotoxicity, therefore reducing in number of or eradicating cancer cells. These considerations equally apply to the diagnosis of metastases and re-current tumors.

In another aspect of the presently disclosed subject matter, the antibody, antibody fragment or derivative thereof described herein is conjugated to a labeling agent or labeling group. Such antibodies are suitable for diagnostic applications. As used herein, the term "labeling group" or "imaging group" refers to a detectable marker, e.g., a radiolabeled amino acid or biotinyl moieties that can be detected by marker avidin. Various methods for labelling polypeptides and glycoproteins, such as antibodies, are known in the art and may be used in performing the presently disclosed subject matter. Examples of suitable labeling groups include, but are not limited to, the following: radioisotopes or radionuclides (e.g., $^{11}$C, $^{13}$N, $^{15}$O, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, and $^{211}$At or an $^{18}$F-labeled substrate), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags).

In certain embodiments, it may be desirable, that the labelling groups are attached by spacer arms of various lengths to reduce potential steric hindrance.

II. Methods for the Use of the Presently Disclosed Isolated Antibodies

The presently disclosed subject matter also provides methods for the use of the presently disclosed antibodies, antibody fragments, or derivatives thereof.

In some embodiments, the presently disclosed subject matter provides a method for assessing the presence of PSMA-expressing cells, the method comprising contacting a cell or tissue suspected of expressing PSMA on its surface with a presently disclosed antibody, antibody fragment, or derivative thereof. In some embodiments, the presently disclosed subject matter provides a method for assessing the presence of a PSMA-expressing cancer cell or tissue, the method comprising: (a) contacting a cell or tissue suspected of expressing PSMA on its surface with a presently disclosed antibody, fragment, or derivative thereof, wherein the presence of PSMA creates an antibody-PSMA complex; (b) applying a detection agent that detects the antibody-PSMA complex; and (c) determining the presence of the PSMA-expressing cancer cell or tissue when the detection agent detects the antibody-PSMA complex.

In some embodiments, the presently disclosed subject matter provides a method for diagnosing a PSMA-expressing cancer in a subject, the method comprising: (a) obtaining a biological sample from the subject, wherein the biological sample is suspected of comprising a PSMA-expressing cancer; (b) contacting the biological sample with a presently disclosed antibody, antibody fragment, or derivative thereof, wherein the presence of a PSMA-expressing cancer in the biological sample creates an antibody-PSMA complex; and (c) diagnosing PSMA-expressing cancer in the subject when an antibody-PSMA complex is detected.

In some embodiments, the presently disclosed subject matter provides a method for inhibiting the growth or survival of a PSMA-expressing cancer cell, the method comprising contacting the surface of the PSMA-expressing cancer cell with a presently disclosed antibody, antibody fragment, or derivative thereof. In some embodiments, the presently disclosed subject matter provides a method for inhibiting the growth or survival of a PSMA-expressing cancer cell, the method comprising contacting the surface of the PSMA-expressing cancer cell with a presently disclosed antibody, fragment, or derivative thereof, wherein the presence of PSMA creates an antibody-PSMA complex, thereby inhibiting the growth or survival of the PSMA-expressing cancer cell.

As used herein, the term "antibody-PSMA complex" refers to the complex formed by a presently disclosed antibody, antibody fragment, or derivative thereof, as a result of the specific interaction between an antibody and PSMA.

As used herein, the term "contacting" refers to any action that results in at least one antibody, antibody fragment, or derivative thereof of the presently disclosed subject matter physically contacting at least one cell or tissue. It thus may comprise exposing the cell or tissue to the antibody, antibody fragment, or derivative thereof in an amount sufficient to result in contact of the antibody, antibody fragment, or derivative thereof with at least one cell. The method can be practiced in vitro or ex vivo by introducing, and preferably mixing, the antibody, antibody fragment, or derivative thereof and cells in a controlled environment, such as a culture dish or tube. The method can be practiced in vivo, in which case contacting means exposing at least one cell in a subject to the antibody, antibody fragment, or derivative thereof of the presently disclosed subject matter, such as administering the antibody, antibody fragment, or derivative thereof to a subject via any suitable route. According to the presently disclosed subject matter, contacting may comprise introducing, exposing, and the like, the antibody, antibody fragment, or derivative thereof at a site distant to the cells to be contacted, and allowing the bodily functions of the subject, or natural (e.g., diffusion) or man-induced (e.g., swirling) movements of fluids to result in contact of the antibody, antibody fragment, or derivative thereof and cells. In some embodiments, contacting is performed in vitro or ex vivo. In some embodiments, contacting is performed in vivo in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like). In some embodiments, the subject is a human.

In some embodiments, the presently disclosed subject matter provides a method for inhibiting growth and/or metastasis of a tumor in a subject having or suspected of having a PSMA-expressing cancer, the method comprising administering to the subject a presently disclosed antibody, antibody fragment, or derivative thereof, or a presently disclosed pharmaceutical composition, in an amount effective to inhibit growth and/or metastasis of the tumor in the subject. In some embodiments, the presently disclosed subject matter provides a method for inhibiting growth and/or metastasis of a tumor in a subject having or suspected of having a PSMA-expressing cancer, the method comprising administering to the subject a presently disclosed antibody, antibody fragment, or derivative thereof, or a presently disclosed pharmaceutical composition, in an amount effective to inhibit growth and/or metastasis of the tumor in the subject, wherein administering to the subject creates antibody-PSMA complexes in the subject.

A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant.

In general, the "effective amount" or "therapeutically effective amount" of an active agent refers to the amount necessary to elicit the desired biological response. As will be appreciated by those of ordinary skill in this art, the effective amount of an agent may vary depending on such factors as the desired biological endpoint, the agent to be delivered, the composition of the encapsulating matrix, the target tissue, and the like.

In some embodiments, the presently disclosed subject matter provides a method for the treatment of a PSMA-expressing cancer in a subject in need thereof, the method comprising administering to the subject a presently disclosed antibody, antibody fragment, or derivative thereof, or a presently disclosed pharmaceutical composition, in an amount effective to treat the PSMA-expressing cancer in the subject. In some embodiments, the presently disclosed subject matter provides a method for the treatment of a PSMA-expressing cancer in a subject in need thereof, the method comprising administering to the subject a presently disclosed antibody, antibody fragment, or derivative thereof, or a presently disclosed pharmaceutical composition, in an amount effective to treat the PSMA-expressing cancer in the subject, wherein administering to the subject creates antibody-PSMA complexes in the subject.

As disclosed herein, the presently disclosed antibodies, antibody fragments, or derivatives thereof may be used for therapy of PSMA-expressing cancers. In some embodiments, the presently disclosed method further comprises administering to the subject an effective amount of a conventional cancer treatment in addition to the presently disclosed antibodies, antibody fragments, or derivatives thereof. Examples of conventional cancer treatments include, but are not limited to, chemotherapy, radiotherapy, immunotherapy, proton therapy, photodynamic therapy, and surgery. In some embodiments, the conventional cancer treatment includes, but is not limited to chemotherapy, radiotherapy, immunotherapy, proton therapy, photodynamic therapy, and surgery.

In some embodiments, the presently disclosed subject matter provides a method for diagnosing and treating a PSMA-expressing cancer in a subject, the method comprising: administering to the subject a presently disclosed antibody, antibody fragment, or derivative thereof in an amount effective to diagnose the PSMA-expressing cancer in the subject; and administering a cancer treatment to the subject. In some embodiments, the cancer treatment may be a presently disclosed antibody, antibody fragment, or derivative thereof. In some embodiments, the cancer treatment may be a conventional cancer treatment. In some embodiments, the cancer treatment may be a combination of at least one presently disclosed antibody, antibody fragment, or derivative thereof and a conventional cancer treatment. In some embodiments, diagnosing and treating a PSMA-expressing cancer with a presently disclosed antibody, antibody fragment, or derivative thereof may occur simultaneously.

In some embodiments, the presently disclosed subject matter provides a method for treating cancer in a subject, the method comprising: requesting a test providing the results of an analysis to determine whether the subject has PSMA-expressing cells and administering at least one presently disclosed antibody, antibody fragment, or derivative thereof to the subject if the subject has PSMA-expressing cells.

In some embodiments, the presently disclosed subject matter provides a method for targeting PSMA expressed by a PSMA expressing cancer cell in a subject, the method comprising administering to the subject a presently disclosed antibody, fragment, or derivative thereof, a presently disclosed pharmaceutical composition, or a presently disclosed diagnostic composition. In some embodiments, the presently disclosed subject matter provides a method for targeting PSMA expressed by a PSMA-expressing cancer cell in a subject, the method comprising administering to the subject a presently disclosed antibody, fragment, or derivative thereof, a presently disclosed pharmaceutical composition, or a presently disclosed diagnostic composition, wherein administering to the subject creates antibody-PSMA complexes in the subject. In some embodiments, the PSMA-expressing cancer is prostate cancer.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Development of New Monoclonal Antibodies Recognizing Human Prostate-Specific Membrane Antigen Methods Cell lines: HEK293T/17 cells obtained from the American Type Culture Collection were grown in DMEM medium (Sigma-Aldrich, Steinheim, Germany) supplemented with 10% v/v fetal bovine serum (FBS; Gibco, Life Technologies, Carlsbad, Calif.). PC-3 and DU145 cells, also from the American Type Culture Collection, LNCaP cells, kindly provided by Z. Hodny (IMG, Prague, Czech Republic), and CW22Rv1 cells, a gift from R. Lapidus (UMBC, Baltimore, Md., USA), were all grown in RPMI 1640 medium (Sigma-Aldrich) with 10% v/v FBS. All cell lines were kept under humidified 5% $CO_2$ atmosphere at 37° C. Stable overexpression of human PSMA in HEK293T/17 cells was realized by transfection of pcDNA4/V5-His A vector (Invitrogen, Carlsbad, Calif.) comprising the cDNA for full-length human PSMA (FOLH1; NCBI Reference sequence: NM_004476.1).

```
>NM_004476.1 Homo sapiens folate hydrolase 1
(FOLH1), transcript variant 1, mRNA
                                    (SEQ ID NO: 23)
CTCAAAAGGGGCCGGATTTCCTTCTCCTGGAGGCAGATGTTGCCTCTCTC

TCTCGCTCGGATTGGTTCAGTGCACTCTAGAAACACTGCTGTGGTGGAGA

AACTGGACCCCAGGTCTGGAGCGAATTCCAGCCTGCAGGGCTGATAAGCG

AGGCATTAGTGAGATTGAGAGAGACTTTACCCCGCCGTGGTGGTTGGAGG

GCGCGCAGTAGAGCAGCAGCACAGGCGCGGGTCCCGGGAGGCCGGCTCTG

CTCGCGCCGAGATGTGGAATCTCCTTCACGAAACCGACTCGGCTGTGGCC

ACCGCGCGCCGCCCGCGCTGGCTGTGCGCTGGGGCGCTGGTGCTGGCGGG

TGGCTTCTTTCTCCTCGGCTTCCTCTTCGGGTGGTTTATAAAATCCTCCA

ATGAAGCTACTAACATTACTCCAAAGCATAATATGAAAGCATTTTTGGAT

GAATTGAAAGCTGAGAACATCAAGAAGTTCTTATATAATTTTACACAGAT
```

-continued

```
ACCACATTTAGCAGGAACAGAACAAAACTTTCAGCTTGCAAAGCAAATTC

AATCCCAGTGGAAAGAATTTGGCCTGGATTCTGTTGAGCTAGCACATTAT

GATGTCCTGTTGTCCTACCCAAATAAGACTCATCCCAACTACATCTCAAT

AATTAATGAAGATGAAATGAGATTTTCAACACATCATTATTTGAACCAC

CTCCTCCAGGATATGAAAATGTTTCGGATATTGTACCACCTTTCAGTGCT

TTCTCTCCTCAAGGAATGCCAGAGGGCGATCTAGTGTATGTTAACTATGC

ACGAACTGAAGACTTCTTTAAATTGGAACGGGACATGAAAATCAATTGCT

CTGGGAAAATTGTAATTGCCAGATATGGGAAAGTTTTCAGAGGAAATAAG

GTTAAAAATGCCCAGCTGGCAGGGGCCAAAGGAGTCATTCTCTACTCCGA

CCCTGCTGACTACTTTGCTCCTGGGGTGAAGTCCTATCCAGATGGTTGGA

ATCTTCCTGGAGGTGGTGTCCAGCGTGGAAATATCCTAAATCTGAATGGT

GCAGGAGACCCTCTCACACCAGGTTACCCAGCAAATGAATATGCTTATAG

GCGTGGAATTGCAGAGGCTGTTGGTCTTCCAAGTATTCCTGTTCATCCAA

TTGGATACTATGATGCACAGAAGCTCCTAGAAAAAATGGGTGGCTCAGCA

CCACCAGATAGCAGCTGGAGAGGAAGTCTCAAAGTGCCCTACAATGTTGG

ACCTGGCTTTACTGGAAACTTTTCTACACAAAAAGTCAAGATGCACATCC

ACTCTACCAATGAAGTGACAAGAATTTACAATGTGATAGGTACTCTCAGA

GGAGCAGTGGAACCAGACAGATATGTCATTCTGGGAGGTCACCGGGACTC

ATGGGTGTTTGGTGGTATTGACCCTCAGAGTGGAGCAGCTGTTGTTCATG

AAATTGTGAGGAGCTTTGGAACACTGAAAAAGGAAGGGTGGAGACCTAGA

AGAACAATTTTGTTTGCAAGCTGGGATGCAGAAGAATTTGGTCTTCTTGG

TTCTACTGAGTGGGCAGAGGAGAATTCAAGACTCCTTCAAGAGCGTGGCG

TGGCTTATATTAATGCTGACTCATCTATAGAAGGAAACTACACTCTGAGA

GTTGATTGTACACCGCTGATGTACAGCTTGGTACACAACCTAACAAAAGA

GCTGAAAAGCCCTGATGAAGGCTTTGAAGGCAAATCTCTTTATGAAAGTT

GGACTAAAAAAAGTCCTTCCCCAGAGTTCAGTGGCATGCCCAGGATAAGC

AAATTGGGATCTGGAAATGATTTTGAGGTGTTCTTCCAACGACTTGGAAT

TGCTTCAGGCAGAGCACGGTATACTAAAAATTGGGAAACAAACAAATTCA

GCGGCTATCCACTGTATCACAGTGTCTATGAAACATATGAGTTGGTGGAA

AAGTTTTATGATCCAATGTTTAAATATCACCTCACTGTGGCCCAGGTTCG

AGGAGGGATGGTGTTTGAGCTAGCCAATTCCATAGTGCTCCCTTTTGATT

GTCGAGATTATGCTGTAGTTTTAAGAAAGTATGCTGACAAAATCTACAGT

ATTTCTATGAAACATCCACAGGAAATGAAGACATACAGTGTATCATTTGA

TTCACTTTTTCTGCAGTAAAGAATTTTACAGAAATTGCTTCCAAGTTCA

GTGAGAGACTCCAGGACTTTGACAAAAGCAACCCAATAGTATTAAGAATG

ATGAATGATCAACTCATGTTTCTGGAAAGAGCATTTATTGATCCATTAGG

GTTACCAGACAGGCCTTTTTATAGGCATGTCATCTATGCTCCAAGCAGCC

ACAACAAGTATGCAGGGGAGTCATTCCCAGGAATTTATGATGCTCTGTTT

GATATTGAAAGCAAAGTGGACCCTTCCAAGGCCTGGGGAGAAGTGAAGAG

ACAGATTTATGTTGCAGCCTTCACAGTGCAGGCAGCTGCAGAGACTTTGA

GTGAAGTAGCCTAAGAGGATTCTTTAGAGAATCCGTATTGAATTTGTGTG

GTATGTCACTCAGAAAGAATCGTAATGGGTATATTGATAAATTTTAAAAT

TGGTATATTTGAAATAAAGTTGAATATTATATATAAAAAAAAAAAAAAAA

AAA
```

Following transfection using jetPRIME (Polyplus-transfection, Illkirch, France), cells were selected in the presence of Zeocin (25 μg/ml; InvivoGen, San Diego, USA). Stable transfectants were isolated by repeated cloning of single cell progeny.

Proteins used in this study: rhPSMA: purification of the extracellular part of human PSMA (rhPSMA; denoted rhGCPII in the original paper, residues 44-750) was described in detail elsewhere (Barinka et al., 2004). Briefly, the recombinant protein was expressed in Schneider S2 cells and purified by ion-exchange chromatography (Q and SP Sepharose FF), affinity chromatography on Lentil-Lectin Sepharose, and size-exclusion chromatography (SEC) on a Superdex 200 column with 20 mM Tris-HCl, 150 mM NaCl, pH 8.0 as mobile phase (all resins/columns from GE Healthcare Bio-Sciences, Uppsala, Sweden). Purified rhPSMA was concentrated and stored at −80° C. until further use.

Avi-PSMA: the extracellular part of human PSMA comprising an N-terminal Avi-tag (Avi-PSMA) was prepared as previously described (Tykvart et al., 2012). Briefly, the recombinant protein was expressed in Schneider S2 cells stably transfected with E. coli biotin protein ligase localized to the endoplasmic reticulum. Avi-PSMA was purified from the cell culture supernatant by affinity chromatography using Streptavidin Mutein Matrix (Roche, Basel, Switzerland) and elution with 2 mM D-biotin. Pooled fractions were concentrated and loaded onto a Superdex 200 column equilibrated with 20 mM Tris-HCl, 150 mM NaCl, pH 8.0 as mobile phase. Purified Avi-PSMA was aliquoted, shock-frozen in liquid nitrogen and stored at −80° C. until further use.

Mouse GCPII, rat GCPII, pig GCPII, human GCPIII, human N-acetylated-alpha-linked acidic dipeptidase (NAALADase) L, mouse GCP3: The recombinant proteins were a kind gift from J. Konvalinka, IOCB, Prague, and their cloning, expression, and purification was described elsewhere (Rovenska et al., 2008; Tykvart et al., 2014).

Hybridomas: Murine mAbs were prepared by immunizing BALB/c mice with purified rhPSMA using a standard protocol (Peknicova et al., 1986). Briefly, two 12-week old female mice were injected subcutaneously with 50 μg rhPSMA in 100 μL PBS mixed with 100 μL of Complete Freund's Adjuvant (Sigma-Aldrich). Three booster subcutaneous injections (50 μg rhPSMA in 100 μL PBS+100 μl Incomplete Freund's Adjuvant) were applied in weekly intervals. The final intraperitoneal booster of 100 μg rhPSMA in 200 μL PBS was administered approximately one month later. Three days after that, mice were sacrificed and spleen-derived immune cells were fused with SP2/0Ag14 myeloma cells using 50% w/v polyethylene glycol 1450 solution (Sigma-Aldrich) (Peknicova et al., 1986). Positive clones were selected by enzyme-linked immunosorbent assay (ELISA) with rhPSMA as target antigen, and then mAb-producing cells were re-cloned by dilution into OptiClone Hybridoma Cloning Factor (MP Biomedicals, Santa Ana, Calif., USA) to isolate a single cell colony, which was expanded and stored in liquid nitrogen.

mAb expression and purification: A starter culture of the hybridoma was expanded in RPMI 1640 supplemented with 10% v/v FBS, ribonucleosides (Gibco), penicillin and streptomycin (PAA, Pasching, Austria).

mAb production was performed in a spinner cultivation system in serum-free RPMI 1640 at 37° C. and 95% humidity under 5% $CO_2$ atmosphere. The production was carried on for 10 days while the culture was additionally spiked twice with a new aliquot of growing hybridoma cells. Cell culture supernatants were harvested by centrifugation at 2701×g for 10 min and concentrated to approximately 1/10 of the original volume using tangential flow filtration (TFF; Millipore, Mosheim, France). mAbs were then purified by affinity chromatography on HiTrap rProtein A Sepharose (GE Healthcare Bio-Sciences). To this end, the concentrated supernatants were loaded onto the column equilibrated in PBS (equilibration buffer), followed by washing with 10 volumes of the equilibration buffer, and the captured mAbs were eluted with 100 mM Na-citrate, pH 5.0. The eluate was immediately neutralized by addition of 1/10 volume of 1M Tris-HCl, pH 8.0, concentrated and subjected to SEC on a Superdex 200 column with PBS as mobile phase. Purified mAbs were concentrated to approximately 5 mg/mL (concentration determined by $A_{280}$) and stored at 4° C. until further use. Purified J591 and GCP-04 mAbs were obtained from Dr. Bander and Dr. Konvalinka, respectively (Barinka et al., 2004; Smith-Jones et al., 2000).

Isotyping: Individual mAbs were isotyped using the Rapid ELISA Mouse mAb Isotyping Kit (Pierce, Thermo Scientific, Rockford, Ill.) according to the manufacturer's protocol. Briefly, 50 µl of the tested sample (250 ng/mL of purified mAb in PBS) was added to all eight wells of a strip, which are pre-coated with different class- or subclass-specific capture antibodies. Then, 50 µL of the Goat Anti-Mouse IgG+IgA+IgM HRP Conjugate was added to each well and incubated for 1 hour at room temperature. Following extensive washing, 75 µL of the supplied tetramethylbenzidine (TMB) substrate was added to each well and the signal was quantified via absorbance measurement at 450 nm (CLARIOstar, BMG Labtech, Ortenberg, Germany).

Fab fragment preparation: Fab fragments of the individual mAbs were prepared using the Mouse $IgG_1$ Fab and $F(ab')_2$ Preparation Kit (Pierce) according to the manufacturer's protocol. Briefly, 5 mg of a given mAb was incubated with 100 µL of Immobilized Ficin in the digestion buffer supplemented with 25 mM cysteine in a final volume of 300 µL for 5 h at 37° C. The digested mAb was separated from the Ficin resin by centrifugation, and the Fab fragment was recovered and separated from undigested mAb and Fc fragment by affinity chromatography using an immobilized Protein A resin in a spin column format. Finally, the Fab fragment was concentrated, loaded onto the Superdex 200 column with PBS as mobile phase and fractions containing the purified Fab were pooled, concentrated, shock-frozen in liquid nitrogen, and stored at −80° C. until further use.

Immunoprecipitation: Purified mAb (8 µg in 400 µL TBS/T; Tris buffered saline/0.1% v/v Tween-20) was added to 25 µL of settled Protein G Dynabeads (Life Technologies) and the mixture was incubated on a rotator for 20 min at room temperature. The beads were then washed three times with 0.3 mL TBS/T, mixed with 100 µL of rhPSMA in TBS (8 µg total) and the mixture was incubated on a rotator for 20 min at room temperature. Following magnetic separation, supernatant containing free rhPSMA was aspired and the beads were washed three times with TBS/T. Finally, captured proteins were eluted from the beads with 50 µL 50 mM glycine, pH 2.8, for 3 min at room temperature. The eluate was immediately neutralized with 1/10 volume of 1M Tris-HCl, pH 8.0, and analyzed by SDS-PAGE followed by Coomassie Brilliant Blue G-250 staining.

Western blotting: Samples of cell lysates and purified proteins were resolved by reducing sodium dodecyl sulfate polyacrylamide gel electrophoresis (SDS-PAGE). Following SDS-PAGE, the proteins were electroblotted onto a PVDF membrane using a Trans-Blot SD Semi-Dry Transfer Cell (Bio-Rad Laboratories, Hercules, Calif.). The membrane was blocked with 5% w/v non-fat dry milk/TBS (blocking buffer) for 1 h and subsequently incubated overnight with 5 µg/mL of mAb in the blocking buffer. Membranes were washed three times with TBS/T and incubated for 2 h with HRP-conjugated goat anti-mouse antibody (1 mg/mL; Bio-Rad) in blocking buffer at 1:10,000 dilution. Finally, blots were washed in TBS/T and developed with Luminata Forte chemiluminescence substrate (Merck, Millipore) according to the manufacturer's protocol. Chemiluminescence signals were visualized using the ImageQuant LAS4000 Imaging System (GE Healthcare Bio-Sciences).

Epitope mapping: A set of 18-mer peptides, in total 83 peptides with 9-residue overlaps, covering the complete sequence of human PSMA was custom-made by PepScan (Lelystad, The Netherlands). A biotin tag was attached to the N-terminus of each peptide via a 6-aminohexanoic acid linker. Maxisorp microtiter plates (Nunc, Thermo Fisher Scientific) were coated with 50 µL of 5 µg/mL strepavidin in TBS buffer overnight at 4° C. The coating solution was discarded and plates were blocked with 200 µL of 0.5% (w/v) BSA for 2 h at room temperature. Subsequently, 50 µL of the peptide solution (2 µM in PBS+0.5 mg/mL BSA) was added to individual wells and incubated for 1 h at room temperature. Excess peptide was washed away and plates were treated with 50 µL mAb solution in PBS (2 µg/mL) for 2 h at RT. Finally, the plates were washed three times in PBS/T and remaining bound mAb was detected after 1 h incubation with a goat-anti-mouse secondary antibody conjugated to horseradish peroxidase (Bio-Rad) diluted 1:10,000 in PBS. Signals were developed by hydrolysis of 0.5 mg/ml o-phenylenediamine dihydrochloride (OPD)+0.015% v/v hydrogen peroxide in 0.05M phosphate-citrate buffer, pH 5, and monitored via absorbance measurement at 492 nm (CLARIOstar).

Native ELISA: ELISA experiments were carried out in white 384-well MaxiSorp plates at 25° C. Plates were coated with 20 µL of streptavidin solution (5 µg/mL in 100 mM Na-borate, pH 9.5) for 1 h. The coating solution was discarded, plates were washed twice with TBS and blocked with 80 µL of 1% w/v BSA for 1 h. Following washing steps (3×TBS/0.05% v/v Tween-20), 20 µL of Avi-PSMA (0.4 nM in TBS/0.1% v/v Tween-20) was added to each well and incubated for 1 h. Plates were washed again with TBS/T and probed with a 2-fold serial dilution of the mAb (20 µL, starting concentration 50 nM in TBS/0.1% v/v Tween-20). Following washing steps, bound mAb was detected after 1 h incubation with a goat-anti-mouse secondary antibody conjugated to horseradish peroxidase (Bio-Rad) diluted 1:50,000 in TBS/T. Signals were developed using the Luminata Forte ELISA chemiluminescence substrate (Merck) according to the manufacturer's protocol. Baseline-corrected data were analyzed with Prism 5 software (GraphPad, San Diego, Calif.).

Surface plasmon resonance real-time affinity measurements: Surface plasmon resonance (SPR) spectroscopy was performed on a BIACORE 2000 instrument (BIACORE, GE Healthcare Bio-Sciences). The Mouse Antibody Capture Kit (GE Healthcare Bio-Sciences) was used to immobilize 6000 resonance units (ΔRU) of anti-mouse IgG on a measuring and a reference channel of a CMS sensorchip using the amine coupling kit (both GE Healthcare Bio-Sciences). The mAbs 5B1, 5D3 and J591 were diluted to 1 µg/mL in HEPES buffered saline (HBS; 10 mM HEPES/NaOH, 150 mM NaCl, pH 7.4) with 0.005% v/v Tween 20 (HBS/T0.005) and applied to the sensorchip to reach ~Δ80 RU immobilized antibody (5B1: Δ85 RU; 5D3: Δ75 RU; J591: Δ80-85 RU). A dilution series from 128-1 nM rhPSMA was prepared in HBS/T0.005 and applied to the sensorchip in the same buffer. Complex formation was monitored for 240 s at a flow rate of 25 µL/min, whereas dissociation was followed for 4,000 s. Regeneration of the sensorchip was achieved by applying up to four injections of the regeneration reagent (glycine/HCl, pH 1.7). The sensorgrams were corrected by double subtraction of the corresponding signals measured for the in-line reference channel and an averaged baseline determined from three buffer blank injections (Myszka et al., 1999). Kinetic parameters were determined by data fitting using BIAevaluation software version 4.1 (BIACORE).

Immunofluorescence microscopy: Cells grown on coverslips coated by 0.1% w/v gelatin from porcine skin were fixed, washed with PBS and incubated with tested mAbs (20 µg/ml) overnight at 4° C. Three fixation protocols were used: i) 4% w/v formaldehyde/PBS for 15 min followed by permeabilization with 0.1% v/v Triton X-100/PBS for 15 min, ii) methanol cooled to −20° C. for 10 minutes, and iii) 5% v/v acetic acid diluted in 95% v/v ethanol cooled to −20° C. for 10 minutes. After washing with PBS/0.05% v/v Tween-20 (PBS/T), slides were incubated for 1 h at RT with the goat anti-mouse secondary antibody conjugated with Alexa Fluor 488 (5 µg/mL in PBS/T; Life Technologies). Following a washing step with PBS/T, processed slides were treated with 4',6-diamidino-2-phenylindole (DAPI; 1 µg/mL) for 5 min. Finally, cells were mounted in VectaShield medium (Vector Laboratories, Burlingame, Calif.). Fluorescence signal was visualized under the confocal microscope TCS SP8 (Leica Microsystems, Wetzlar, Germany) using the immersion oil objective with 63× magnification. Digital scans were processed with Adobe Photoshop software (Adobe Systems, San Jose, Calif.).

Flow cytometry: Cells were harvested by treatment with 0.025% w/v Trypsin/0.01% w/v EDTA/PBS for 3 min, washed and incubated with tested mAbs at a final concentration of 5 µg/ml in a total volume of 20 µL for 30 min at 4° C. In case of titration experiments, the anti-PSMA mAbs 5B1, 5D3 and J591 were used in two-fold dilution series spanning the concentration range from 533 nM down to 0.25 pM. Following the washing step, cells were incubated with a goat anti-mouse secondary antibody conjugated to Alexa Fluor 647 (4 µg/ml; Life Technologies). Finally, cells were washed and stained with Hoechst 33258 to gate the viable cell population. All incubation and washing steps were done in PBS supplemented with 0.5% w/v gelatin from cold water fish skin (Sigma-Aldrich). Cell samples were immediately analyzed using the LSRII flow cytometer (BD Biosciences, San Jose, Calif.). Minimum 30,000 viable cells were gated for subsequent analysis with FlowJo software (FlowJo, LLC, Ashland, Oreg.).

Antibody Labeling: 50 µg of each carrier-free IgG or Fab were labeled by pipetting into a microcentrifuge tube containing 10 µg of IRDye680RD-NHS ester or IRDye800CW-NHS ester (LI-COR Biosciences, Lincoln, Nebr.) in 2 µL of DMSO and complementing the volume to 100 µL by adding 50-70 µL of PBS, pH 7.4. The conjugation reaction was performed for 12 min at ambient temperature before loading the sample on a PBS-conditioned Sephadex G-25 size-exclusion column (GE Healthcare Bio-Sciences), which was operated according to the manufacturer's instructions. Antibody was assayed to contain ≤5% (by fluorescence) unincorporated dye using silica gel HLF in normal phase TLC (Analtech, Newark Del.) developed in 100% v/v MeCN+ 0.1% v/v TFA, where the $R_f$ of the antibody conjugate is 0 and the $R_f$ of free dye is >0.5. Labeled antibodies were formulated as 30 µg of conjugate in 200 µL of sterile PBS, pH 7.5 immediately prior to injection.

In vivo near infrared fluorescence (NIRF) imaging: All animal studies were conducted in full compliance with a protocol approved by the Johns Hopkins University Animal Care and Use Committee. Young adult male athymic nude mice (Taconic Biosciences, Hudson, N.Y.) were prepared as described previously (Banerjee et al., 2015; Yang et al., 2016) to contain a single subcutaneous xenograft each of PSMA-positive PC-3 PIP cells and PSMA-negative PC-3 flu cells (a gift from Warren B. Heston, the Cleveland Clinic). Near IR dye-labeled intact IgG or 5D3 Fab, as indicated, was injected via the tail vein when tumor xenografts had reached 4-6 mm in diameter. Imaging was performed on a Pearl Impulse imager (LI-COR Biosciences). All images were displayed using the manufacturer's software and normalized to the same acquisition time to facilitate direct comparison between mice and over time. Image acquisition began 45 min after fluorescent antibody injection and concluded 72 h post-injection. Following the 72 h image acquisition, each mouse was euthanized by 3% v/v isoflurane-anesthetized cervical dislocation and dissected to allow imaging of the tumors without attenuation from the skin.

Ex vivo NIRF imaging of tumor sections: Immediately following euthanasia, both PSMA-positive PC-3 PIP and PSMA-negative PC3 flu tumors were harvested and frozen over dry ice. The tumors were then sectioned to 20 µm using an HM Microm 550 cryotome (Thermo Fisher Scientific) and annealed to charged glass slides (VWR, Radnor, Pa.). Slides were allowed to thaw to ambient temperature and dry prior to scanning using a LI-COR Odyssey imager (LI-COR Biosciences). Both 700 nm and 800 nm emission channels were captured and displayed using the manufacturer's software.

Results and Discussion mAb preparation and purification: Four hybridoma cell lines were prepared according to standard protocols using rhPSMA as an immunogen and later as a target for the identification of antibody-producing hybridoma clones. The PSMA-specific mAbs were purified to homogeneity from the hybridoma supernatants by protein A affinity chromatography followed by size exclusion chromatography (FIG. 3A and FIG. 3B). The overall yield was 5.2, 5.7, 17.6 and 33.4 mg per liter cell culture supernatant for 1A11, 3F11, 5B1 and 5D3, respectively. Using Rapid ELISA Mouse Antibody Isotyping Kit, it was determined that all mAbs are of the IgG1/κ isotype (Table 1, below).

TABLE 1

Basic characteristics of the newly developed mAbs

| mAb | Isotype | Epitope | Residues* | Species$ | Experimental use# |
|---|---|---|---|---|---|
| 1A11 | IgG1/κ | linear | 271-288 | Human | WB, ICC, IHC, ELISA |
| 3F11 | IgG1/κ | linear | 226-243 | Human, mouse, rat, pig, dog | WB, ICC, IHC, ELISA |

TABLE 1-continued

Basic characteristics of the newly developed mAbs

| mAb | Isotype | Epitope | Residues* | Species$ | Experimental use# |
|---|---|---|---|---|---|
| 5B1 | IgG1/κ | conformational | ND | Human | IF, ICC, IHC, ELISA, FC, in vivo |
| 5D3 | IgG1/κ | conformational | ND | Human | IF, ICC, IHC, ELISA, FC, in vivo |

*residues of human PSMA recognized by a given mAb
$PSMA orthologs recognized by a given mAb
WB, Western blotting; ELISA, enzyme-linked immunosorbent assay; IHC—immunohistochemistry; ICC—immunocytochemistry; FC—flow cytometry; IF—immunofluorescence Immunoprecipitation and epitope mapping: The initial experiments were aimed to determine whether a given mAb recognizes a linear or a conformational epitope of human PSMA as this information helps in governing subsequent experimental approaches. To this end, immunoprecipitation (IP) was used to identify mAbs recognizing rhPSMA in its native conformation. Individual mAbs were captured on protein-G paramagnetic beads and then incubated with rhPSMA. Following extensive washing, beads were treated with 100 mM glycine/HCl, pH 2.8, and released proteins were analyzed by SDS-PAGE (FIG. 4). Results clearly showed that clones 5D3 and 5B1 are able to bind and immunoprecipitate native rhPSMA, while 1A11 and 3F11 did not recognize the fully folded native PSMA ectodomain. The J591 and GCP-04 mAbs, which are known to recognize native and denatured PSMA, respectively, were used as control mAbs (Liu et al., 1997; Barinka et al., 2004).

To pinpoint epitopes recognized by individual mAbs, a set of 83 overlapping 18-mer peptides covering the entire sequence of human PSMA was used. N-terminally biotinylated peptides were immobilized on a streptavidin-coated 96-well plate and probed with a given mAb at 2 µg/mL concentration. Following extensive washing, bound mAbs were detected by anti-mouse secondary antibody conjugated to horse radish peroxidase. The results were in agreement with the immunoprecipitation experiments. First, the absence of any detectable signal for 5B1 and 5D3 suggests that these two mAbs only recognize conformational epitopes present at the PSMA surface and cannot bind to linear 18-mer peptides comprising the library. Conversely, 1A11 and 3F11 specifically bound the PSMA-derived linear peptides spanning residues 271-288 and 226-243, respectively (Table 1 above, FIG. 5A). Of note, within fully folded PSMA, the 271-288 amino acid segment is located at the dimer interface and, therefore, not accessible to the mAb binding. The 226-243 epitope is partially buried in the three-dimensional structure of the native enzyme and adopts a distinct α-helical fold, again precluding efficient binding of mAb 3F11 to this epitope within the context of native PSMA.

Combined IP and epitope-mapping data clearly define suitable experimental setups for the individual mAbs to be used (Table 1 above). 1A11 and 3F11 are mostly suitable for techniques dealing with denatured PSMA, including Western blotting, immunocytochemistry, immunohistochemistry, and ELISA under denaturing conditions. On the contrary, 5B1 and 5D3 are the best suited for immunofluorescence (IF), immunocytochemistry (ICC), immunohistochemistry (IHC), ELISA, flow cytometry (FC), and in vivo experiments where native PSMA prevails.

PSMA specificity and species cross-reactivity: Although all four mAbs were raised against purified human PSMA, whether they (i) cross-react with non-related human proteins; (ii) recognize human glutamate carboxypeptidase III (GCPIII), a close PSMA homolog with 67% identity at the amino acid level; and (iii) recognize PSMA/GCPIII orthologs from different species was of interest. To this end, Western blotting was first employed, in which PSMA-expressing cells and purified PSMA orthologs/paralogs were used to probe the specificity of 1A11 and 3F11. The data (FIG. 5B and FIG. 6) can be summarized as follows: (i) both 1A11 and 3F11 do not cross-react with non-related human proteins as PC-3 and HEK293 cell lysates are negative for any staining and only a single band with a size corresponding to PSMA was observed in lysates from PSMA-positive LNCaP and CWR22 cells; (ii) 1A11 does not recognize any PSMA paralogs/orthologs, whereas 3F11 can be used to detect mouse, rat and pig PSMA, human and mouse GCPIII (FIG. 5B), but not human and mouse NAALADase L (not shown).

FIG. 5A shows epitopes of human PSMA recognized by 1A11 and 3F11, together with the alignment with corresponding sequences from PSMA orthologs/paralogs. Although not tested experimentally, this sequence alignment suggests that 3F11 will also recognize canine PSMA, expanding thus the utility of this mAb to yet another experimental animal model. The 3F11 PSMA cross-reactivity with several mammalian species is similar to that of the mAb GCP-04, although the latter is somewhat more sensitive for human PSMA (cf. FIG. 5B). However, as 3F11 and GCP-04 recognize distinct epitopes within the PSMA sequence, they may be used back-to-back to confirm the specificity of staining in human/animal tissues.

We recently determined that epitopes recognized by YPSMA-1 and YPSMA-2, two widely used commercial mAbs, span amino acids 469-486 (Tykvart et al., 2014). Consequently, these mAbs will definitely cross-react with human PSMA-L, an intracellular protein with 98% amino acid sequence identity to human PSMA (O'Keefe et al., 2004). PSMA-L is only found in humans and higher primates, and the two sequence homology regions between PSMA and PSMA-L comprise residues 1-442 and 309-750, respectively. Contrary to YPSMA-1 and YPSMA-2, our 3F11 and 1A11 mAbs (as well as GCP-04 and the mAb 3E6 from Dako) will not cross-react with PSMA-L as their recognized epitopes are missing there. Consequently, the new mAbs can be preferably used for IHC staining to ensure high specificity for PSMA in human tissue samples.

Immunofluorescence microscopy: To determine compatibility of individual mAbs with different methods of sample preparation for immunofluorescence microscopy, their performance was evaluated using LNCaP and control PC-3 cells (FIG. 7). Cell lines were fixed on glass coverslips using various fixation protocols including ethanol/5% acetic acid, methanol, and 4% paraformaldehyde. Following a blocking step, samples were probed with the indicated mAb at 20 µg/mL and specific binding was detected using an Alexa 488-labeled anti-mouse secondary antibody.

The observed staining pattern is in line with the findings on mAb specificity stated above, including their recognition of the denatured (3F11 and 1A11) or native (5B1 and 5D3) antigen. First, the absence of a fluorescence signal in PC-3 cells confirmed high specificity of all mAbs for human PSMA. For the 3F11 and 1A11 and LNCaP cells, the strongest signal was observed when a denaturing fixation by ethanol/acetic acid or methanol was used, while much weaker labeling was seen when cells were fixed with paraformaldehyde. To the contrary, the staining intensity for 5B1 and 5D3 was highest using the "native" paraformaldehyde fixation, less pronounced in methanol fixation and very weak (negligible) when acetic acid/ethanol mixture was used.

Side-by-side comparison of the mAbs described here with GCP-04 and J591 revealed identical staining pattern and similar staining intensity for the particular type of fixation. Furthermore, the staining pattern of 5B1 on Triton-permeabilized and non-permeabilized LNCaP cells also were compared. With permeabilized cells, both cytoplasmic and plasma-membrane localization of PSMA was visible, while only the cell-surface signal was detected using non-permeabilized cells (FIG. 8A and FIG. 8B).

Flow cytometry: LNCaP and PC3 cells were used to assess the suitability of mAbs 5D3 and 5B1 for flow cytometry, as well as to compare their performance with J591. mAb binding (5 μg/mL) to the PSMA displayed on the surface of live cells was detected via indirect staining with a secondary antibody labeled with Alexa Fluor 647 (FIG. 9). As seen from the flow cytometry histograms, no staining was observed for PSMA-negative PC3 cells, confirming the lack of cross-reactivity of all tested mAbs with other human proteins. At the same time, the PSMA-positive LNCaP cell line was specifically labeled by all three mAbs with the median signal intensity highest for 5D3, followed by J591 and 5B1 (FIG. 9). These results were further corroborated using additional PSMA-positive (CW22Rv1) and PSMA-negative (DU-145) cells (FIG. 10A, FIG. 10B, and FIG. 10C). Additionally, HEK293T cells transfected with human PSMA, human GCP3 or mouse PSMA were used to test reactivity of the three mAbs towards these proteins. As predicted, all three mAbs stained cells expressing human PSMA, but no staining was observed for HEK293T cells transfected with mouse PSMA and a much weaker signal was detected for human GCP3 (FIG. 10A, FIG. 10B, and FIG. 10C). Collectively, both 5D3 and 5B1 mAbs are highly specific for human PSMA; in the case of 5D3, performance was similar or even better than J591.

Affinity determined by ELISA, surface plasmon resonance, and flow cytometry: To determine the affinity of mAbs 5D3 and 5B1 in comparison with J591 for PSMA, three complementary experimental setups were employed, including ELISA, surface-plasmon resonance, and flow cytometry. The results are summarized in Table 2 below and FIG. 11A, FIG. 11B, FIG. 11C, FIG. 11D, FIG. 11E and FIG. 11F. First, ELISA under native conditions was used to both verify the practical applicability of 5B1 and 5D3 in this experimental setup and determine binding affinities. Max-iSorp plates were coated with streptavidin and charged with Avi-PSMA at 0.04 μg/mL (0.4 nM). Blocked plates were then incubated with a dilution series of 5B1, 5D3 and J591, and bound mAb was detected by anti-mouse secondary mAb conjugated to HRP and a Luminata Forte ELISA chemiluminescence substrate. Resulting signals were fitted using GraphPad (one site total binding model), and normalized binding curves are shown in FIG. 11A. Dissociation constants ($K_D$) for 5B1, 5D3, and J591 were determined to be 0.26 nM, 0.14 nM, and 1.12 nM, respectively (Table 2 below).

TABLE 2

Affinities of individual mAbs as determined by ELISA, flow cytometry, and surface-plasmon resonance.

| mAb | ELISA [nM] | FC [nM] | SPR $k_{on}$ [$10^5 \cdot (M \cdot s)^{-1}$] | $k_{off}$ [$10^{-4} \cdot s^{-1}$] | $K_D$ [nM] | $\chi^2$ for Langmuir fit |
|---|---|---|---|---|---|---|
| 5B1 | 0.26 ± 0.07 | 1.8 ± 0.13 | n.d.$^a$ | n.d.$^a$ | n.d.$^a$ | 5.86$^a$ |
| 5D3 | 0.14 ± 0.01 | 2.1 ± 0.10 | 2.36 ± 0.003 | 2.56 ± 0.002 | 1.08 ± 0.002 | 0.40 |
| J591 | 1.12 ± 0.10 | 15.2 ± 1.3 | 1.02 ± 0.0008 (1.12 ± 0.06)$^b$ | 1.23 ± 0.002 (0.84 ± 0.15)$^b$ | 1.21 ± 0.002 (0.75 ± 0.14)$^b$ | 0.29 |

$^a$The binding mode of the 5B1 antibody did not show a simple 1:1 association according to the Langmuir model as indicated by the high Chi$^2$ value.
$^b$Kinetic data obtained with an inverted SPR measurement by (Tykvart et al., 2014) for J591 are given in brackets.

In a complementary approach, affinities of 5B1, 5D3 and J591 were determined by flow cytometry. To this end, LNCaP cells were incubated with dilution series of all three mAbs (533 nM-0.25 pM) followed by visualization with a secondary antibody conjugated to Alexa Fluor 647. Resulting signals were fitted using GraphPad (one site total binding model), and normalized binding curves are shown in FIG. 11B and calculated affinity constants are listed in Table 2 above. Overall, these data are consistent with those from ELISA measurements showing that under this experimental setup our novel mAbs have approximately 8-fold higher affinity for PSMA than J591.

Finally, to precisely determine kinetic and thermodynamic binding constants of individual mAbs, surface-plasmon resonance (SPR) real-time analyses on a BIACORE instrument were performed. Here, a sensorchip surface was coated with an anti-mouse IgG capture antibody, which was subsequently used to capture the respective mAb. The sensograms obtained by applying recombinant rhPSMA were fitted to a 1:1 binding model according to Langmuir, which resulted in dissociation constants of 1.08 nM for 5D3 and 1.21 nM for J591 (FIG. 11C, FIG. 11D). In line with the ELISA and FC measurements, these results reveal a $K_D$ in the low single-digit nanomolar range, with the best affinity for mAb 5D3. Previous affinity measurements for J591 in an inverted setup with Avi-PSMA immobilized on the sensorchip via NEUTRAVIDIN indicated 1.6-fold higher affinity (750 pM, (Tykvart et al., 2014)). In contrast, the fit of the 5B1 sensograms to a Langmuir binding model (FIG. 11E) resulted in a strong discrepancy, causing an elevated Chi$^2$ ($\chi^2$) of 5.9 compared to 0.4 and 0.3 for the 5D3 and J591 antibodies, respectively.

Hence, the raw data measured for 5B1 were fitted to different binding models including (i) bivalent analyte ($\chi^2$=3.7), (ii) 1:1 binding with mass transfer ($\chi^2$=4.1), (iii) two state reaction ($\chi^2$=46.1), and (iv) heterogeneous ligand ($\chi^2$=0.75). Thus, the biphasic dissociation observed for the 5B1 sample could point to an inhomogeneous antibody pool secreted by the hybridoma clone, such as the differential N-glycosylation or other post-translational modifications in the V-regions. However, additional experiments including 5B1 gene cloning/sequencing, separation of the putative mAb mixture by anion- or cation-exchange chromatography and isoelectric focusing did not confirm the existence of different antibody species (data not shown).

In vivo/ex vivo NIRF imaging: Finally, as a proof-of-concept experiment for our future endeavors focusing on the development of imaging and therapeutic reagents, an established mouse model implanted with paired PC3 based xenograft lines that are isogenic except for PSMA expression (Kiess, Minn et al., 2015) was used to (i) assess the suitability of 5D3, the best performing mAb, as well as its Fab, fragment for in vivo imaging; and (ii) to directly compare the performance of our mAbs to J591 and GCPII-04, two commercially available mAbs. Each whole IgG antibody (5B1, 3F11, 5D3, GCPII-04 and 1A11) was fluorescently labeled with IRDye680RD to allow for co-injection and direct comparison with the gold standard for immunoimaging of PSMA, J591 (Bouchelouche et al., 2009; Milowsky et al., 2007; Nakajima et al., 2011; Osborne et al., 2013), which was labeled with the orthogonal IRDye800CW.

As shown in FIG. 12A, all antibodies accumulated within the PSMA-positive PC3 tumor and the highest signal-to-noise occurred around 72 h post-injection for all clones with the exception of J591, which yielded tumor-specific images 48 h post-injection. Notably, clone 3F11 displayed an overall low uptake in comparison with all other clones.

The specificity of each antibody was assessed by opening the ventral skin following euthanasia 72 h post-injection such that both tumors could easily be imaged without attenuation from skin. FIG. 12B shows mice with the indicated IRDye680RD-labeled mAb in red overlaid with IRDye800CW-labeled J591 in green where yellow indicates co-localization. Again, all mAbs were taken up by the PSMA-expressing tumor whereas, notably, 3F11 was also accumulated by the PSMA-negative tumor. Additionally, 3F11 and 1A11 both displayed non-homogenous co-localization with J591, suggesting reduced specificity for native PSMA. Both 5D3 and 5B1 displayed uptake in the PSMA-positive tumor only and co-localized with J591. Likewise, GCPII-04 displayed PSMA-specific tumor uptake and homogenous distribution and co-localized with J591 in vivo, even though GCPII-04 recognizes denatured PSMA (Barinka et al., 2004; Tykvart et al., 2014).

In the interest of developing a theranostic agent suitable for clinical translation, a Fab fragment of 5D3 was prepared and evaluated for its in vivo pharmacokinetics and tumor specificity alongside the parental IgG. FIG. 13A, FIG. 13B, and FIG. 13C show the pharmacokinetic distribution of 5D3 IgG (FIG. 13A), Fab (FIG. 13B) and their overlay (FIG. 13C), where IgG is displayed in red and the Fab is indicated green. Both the IgG and Fab accumulated in the PSMA-positive tumor, although the Fab was observed in the tumor as early as 45 min post-injection, while with the IgG the tumor was first observed only 4 h post-injection. The high signal-to-noise for Fab and IgG was achieved at 4 h and 24 h post-injection, respectively, and 12 h post-injection, the degree of observed overlap between IgG and Fab uptake was nearly 100% (FIG. 13C). Ex vivo data reveal homogeneous uptake in the PSMA-positive tumor by both IgG and Fab and confirm their high specificity for PSMA (FIG. 13D, FIG. 13E, and FIG. 13F).

Both tumors were sectioned after imaging and then the sections were imaged at high (≥25 µm) resolution to determine whether the 5D3 Fab exhibits broader uptake within the tumor sections relative to IgG distribution. Panels G and H show representative sections of the PSMA-positive and PSMA-negative tumors and the distribution of each immunoglobulin format. The IgG (red) is taken up by the PSMA-positive tumor (panel G) primarily along the rim with focal uptake scattered throughout the interior. The Fab (green) is also primarily distributed along the rim with less scattered uptake in the interior. The overlay (leftmost section) demonstrates more Fab along the rim than IgG, suggesting greater perfusion allowing for more binding to epithelial PSMA. The PSMA-negative tumor section (panel H) revealed very little uptake by either IgG or Fab and showed a small amount of uptake around the tumor rim, as well as a small region in the interior, which might reflect blood flow and pooling (Ng et al., 2007).

In summary, the 5D3 IgG provided high tumor contrast between 12-24 h post-injection (depending on which IRDye was used) and exhibited homogenous uptake consistent with that demonstrated by J591 in the PSMA-positive tumor (FIG. 12A, and FIG. 12B). There was no observable mAb uptake in the PSMA-negative tumor. Likewise, the Fab fragment of 5D3 also displayed PSMA-specific tumor uptake and provided high tumor contrast as early as 2 h post-injection and maintained high contrast through 24 h, after which the signal within the tumor began to wane (FIG. 13B). Whole mount tumor sections taken at 72 h post-injection revealed more intense distribution of the Fab fragment within the tumor compared with the IgG, also radiating further from the tumor rim than the IgG (FIG. 13G). The faster pharmacokinetics observed with the 5D3 Fab coupled with its greater penetration into the tumor make it an attractive option for both diagnostic imaging and radioimmunotherapy, which benefit from fast binding kinetics and widespread epithelial target binding (Larson et al., 2015; Sofou 2008; Wittrup et al., 2012).

The mAb 5B1 also displayed favorable pharmacokinetics, but exhibited some non-target background uptake in cervical lymph nodes through the first 72 h.

The mAb 1A11 was selective for PSMA-positive tumor uptake but also suffered from non-target tissue uptake through the initial 48 h post-injection, while mAb 3F11 displayed a large extent of non-specific uptake throughout the mouse, including uptake in the PSMA-negative tumor (FIG. 12A and FIG. 12B). This likely reflects the finding that the 3F11 clone also recognizes murine forms of GCPII, which are present in many tissues including blood (Rovenska et al., 2008).

The mAb GCPII-04 was described before and has been included here for comparison due to its known affinity and specificity for denatured PSMA (Barinka et al., 2004; Tykvart et al., 2014). GCPII-04 also displayed high-contrast, though lower intensity of PSMA-specific tumor uptake. Comparison of intra-tumor accumulation with J591 at 72 h revealed GCPII-04 uptake in regions of the tumor where J591 binding was largely absent (FIG. 12B, tumor inset), suggesting the binding of GCPII-04 to necrotic, denatured tumor tissue, similar to the in vivo binding mechanism of the mAb 7E11 (ProstaScint™) (Troyer et al., 1997).

Summary

Provided herein is the detailed characterization of four novel murine monoclonal antibodies (mAbs) recognizing human PSMA, as well as PSMA orthologs from different species. Performance of purified mAbs was assayed using a comprehensive panel of in vitro experimental setups including Western blotting, immunofluorescence, immunohistochemistry, ELISA, flow cytometry, and surface-plasmon resonance. Furthermore, a mouse xenograft model of prostate cancer was used to compare the suitability of the mAbs in in vivo applications. All mAbs demonstrate high specificity for PSMA as documented by the lack of cross-reactivity to unrelated human proteins.

The 3F11 and 1A11 mAbs bind linear epitopes spanning residues 226-243 and 271-288 of human PSMA, respectively. Additionally, 3F11 is suitable for the detection of PSMA orthologs from mouse, pig, dog, and rat in experimental setups, where the denatured form of PSMA is used.

5D3 and 5B1 mAbs recognize distinct surface-exposed conformational epitopes and are suitable for targeting PSMA in its native conformation. Using a mouse xenograft model of prostate cancer, it is shown that both the intact 5D3 and its Fab fragment are suitable for in vivo imaging. With apparent affinities of 0.14 nM and 1.2 nM as determined by ELISA and flow cytometry, respectively, 5D3 has approximately 10-fold higher affinity for PSMA than the clinically validated mAb J591. The presently disclosed mAbs are prime candidates for the development of next-generation theranostics targeting PSMA.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Banerjee, S. R., Ngen, E. J., Rotz, M. W., Kakkad, S., Lisok, A., Pracitto, R., Pullambhatla, M., Chen, Z., Shah, T., Artemov, D., Meade, T. J., Bhujwalla, Z. M. & Pomper, M. G. (2015) Synthesis and Evaluation of Gd(III)-Based Magnetic Resonance Contrast Agents for Molecular Imaging of Prostate-Specific Membrane Antigen, *Angewandte Chemie*. 54, 10778-82.

Barinka, C., Mlcochova, P., Sacha, P., Hilgert, I., Majer, P., Slusher, B. S., Horejsi, V. & Konvalinka, J. (2004) Amino acids at the N- and C-termini of human glutamate carboxypeptidase II are required for enzymatic activity and proper folding, *European journal of biochemistry/FEBS* 271, 2782-90.

Barinka, C., Ptacek, J., Richter, A., Novakova, Z., Morath, V. & Skerra, A. (2016) Selection and characterization of Anticalins targeting human prostate-specific membrane antigen (PSMA), *Protein Eng Des Sel*. 29, 105-15.

Barinka, C., Rojas, C., Slusher, B. & Pomper, M. (2012) Glutamate carboxypeptidase II in diagnosis and treatment of neurologic disorders and prostate cancer, *Current medicinal chemistry* 19, 856-70.

Bostwick, D. G., Pacelli, A., Blute, M., Roche, P. & Murphy, G. P. (1998) Prostate specific membrane antigen expression in prostatic intraepithelial neoplasia and adenocarcinoma: a study of 184 cases, *Cancer*. 82, 2256-2261.

Bouchelouche, K., Capala, J. & Oehr, P. (2009) Positron emission tomography/computed tomography and radioimmunotherapy of prostate cancer, *Current opinion in oncology*. 21, 469-74.

Chang, S. S., O'Keefe, D. S., Bacich, D. J., Reuter, V. E., Heston, W. D. & Gaudin, P. B. (1999) Prostate-specific membrane antigen is produced in tumor-associated neovasculature, *ClinCancer Res*. 5, 2674-2681.

Dassie, J. P., Hernandez, L. I., Thomas, G. S., Long, M. E., Rockey, W. M., Howell, C. A., Chen, Y, Hernandez, F. J., Liu, X. Y, Wilson, M. E., Allen, L. A., Vaena, D. A., Meyerholz, D. K. & Giangrande, P. H. (2014) Targeted inhibition of prostate cancer metastases with an RNA aptamer to prostate-specific membrane antigen, *Molecular therapy: the journal of the American Society of Gene Therapy*. 22, 1910-22.

Ellis, R. J., Kaminsky, D. A., Zhou, E. H., Fu, P., Chen, W. D., Brelin, A., Faulhaber, P. F. & Bodner, D. (2011) Ten-year outcomes: the clinical utility of single photon emission computed tomography/computed tomography capromab pendetide (Prostascint) in a cohort diagnosed with localized prostate cancer, *International journal of radiation oncology, biology, physics*. 81, 29-34.

Foss, C. A., Mease, R. C., Cho, S. Y, Kim, H. J. & Pomper, M. G. (2012) GCPII imaging and cancer, *Current medicinal chemistry*. 19, 1346-59.

Gordon, I. O., Tretiakova, M. S., Noffsinger, A. E., Hart, J., Reuter, V. E. & Al-Ahmadie, H. A. (2008) Prostate-specific membrane antigen expression in regeneration and repair, *Modern pathology: an official journal of the United States and Canadian Academy of Pathology, Inc.* 21, 1421-7.

Haberkom, U., Eder, M., Kopka, K., Babich, J. W. & Eisenhut, M. (2016) New Strategies in Prostate Cancer: Prostate-Specific Membrane Antigen (PSMA) Ligands for Diagnosis and Therapy, *Clinical cancer research: an official journal of the American Association for Cancer Research*. 22, 9-15.

Hlouchova, K., Barinka, C., Konvalinka, J. & Lubkowski, J. (2009) Structural insight into the evolutionary and pharmacologic homology of glutamate carboxypeptidases II and III, *FEBS J*. 276, 4448-62.

Hohberg, M., Eschner, W., Schmidt, M., Dietlein, M., Kobe, C., Fischer, T., Drzezga, A. & Wild, M. (2016) *Lacrimal Glands May Represent Organs at Risk for Radionuclide Therapy of Prostate Cancer with [Lu]DKFZ-PSMA-617, Molecular imaging and biology: MIB: the official publication of the Academy of Molecular Imaging*.

Holland, J. P., Divilov, V., Bander, N. H., Smith-Jones, P. M., Larson, S. M. & Lewis, J. S. (2010) 89Zr-DFO-J591 for immunoPET of prostate-specific membrane antigen expression in vivo, *Journal of nuclear medicine: official publication, Society of Nuclear Medicine*. 51, 1293-300.

Huber, F., Montani, M., Sulser, T., Jaggi, R., Wild, P., Moch, H., Gevensleben, H., Schmid, M., Wyder, S. & Kristiansen, G. (2015) Comprehensive validation of published immunohistochemical prognostic biomarkers of prostate cancer—what has gone wrong? A blueprint for the way forward in biomarker studies, *British journal of cancer*. 112, 140-8.

Kampmeier, F., Williams, J. D., Maher, J., Mullen, G. E. & Blower, P. J. (2014) Design and preclinical evaluation of a 99mTc-labelled diabody of mAb J591 for SPECT imaging of prostate-specific membrane antigen (PSMA), *EJNMMI research*. 4, 13.

Kiess, A. P., Banerjee, S. R., Mease, R. C., Rowe, S. P., Rao, A., Foss, C. A., Chen, Y, Yang, X., Cho, S. Y, Nimmagadda, S. & Pomper, M. G. (2015) Prostate-specific membrane antigen as a target for cancer imaging and therapy, *Q J Nucl Med Mol Imaging.* 59, 241-68.

Kiess, A. P., Minn, I., Chen, Y, Hobbs, R., Sgouros, G., Mease, R. C., Pullambhatla, M., Shen, C. J., Foss, C. A. & Pomper, M. G. (2015) Auger Radiopharmaceutical Therapy Targeting Prostate-Specific Membrane Antigen, *Journal of nuclear medicine: official publication, Society of Nuclear Medicine.* 56, 1401-7.

Kratochwil, C., Giesel, F. L., Stefanova, M., Benesova, M., Bronzel, M., Afshar-Oromieh, A., Mier, W., Eder, M., Kopka, K. & Haberkorn, U. (2016) PSMA-targeted radionuclide therapy of metastatic castration-resistant prostate cancer with Lu-177 labeled PSMA-617, *Journal of nuclear medicine: official publication, Society of Nuclear Medicine.*

Larson, S. M., Carrasquillo, J. A., Cheung, N. K. & Press, 0. W. (2015) Radioimmunotherapy of human tumours, *Nature reviews Cancer.* 15, 347-60.

Liu, H., Moy, P., Kim, S., Xia, Y, Rajasekaran, A., Navarro, V., Knudsen, B. & Bander, N. H. (1997) Monoclonal antibodies to the extracellular domain of prostate-specific membrane antigen also react with tumor vascular endothelium, *Cancer research.* 57, 3629-34.

Milowsky, M. I., Nanus, D. M., Kostakoglu, L., Sheehan, C. E., Vallabhajosula, S., Goldsmith, S. J., Ross, J. S. & Bander, N. H. (2007) Vascular targeted therapy with anti-prostate-specific membrane antigen monoclonal antibody J591 in advanced solid tumors, *Journal of clinical oncology: official journal of the American Society of Clinical Oncology* 25, 540-7.

Myszka, D. G. (1999) Improving biosensor analysis, *J Mol Recognit* 12, 279-84.

Nakajima, T., Mitsunaga, M., Bander, N. H., Heston, W. D., Choyke, P. L. & Kobayashi, H. (2011) Targeted, activatable, in vivo fluorescence imaging of prostate-specific membrane antigen (PSMA) positive tumors using the quenched humanized J591 antibody-indocyanine green (ICG) conjugate, *Bioconjugate chemistry* 22, 1700-5.

Ng, Q. S., Goh, V., Milner, J., Padhani, A. R., Saunders, M. I. & Hoskin, P. J. (2007) Acute tumor vascular effects following fractionated radiotherapy in human lung cancer: In vivo whole tumor assessment using volumetric perfusion computed tomography, *International journal of radiation oncology, biology, physics.* 67, 417-24.

O'Keefe, D. S., Bacich, D. J. & Heston, W. D. (2004) Comparative analysis of prostate-specific membrane antigen (PSMA) versus a prostate-specific membrane antigen-like gene, *The Prostate.* 58, 200-10.

Osborne, J. R., Akhtar, N. H., Vallabhajosula, S., Anand, A., Deh, K. & Tagawa, S. T. (2013) Prostate-specific membrane antigen-based imaging, *Urologic oncology.* 31, 144-54.

Peknicova, J., Capkova, J., Cechova, D. & Sulcova, B. (1986) Preparation and characterization of a monoclonal antibody against boar acrosin, *Folia biologica.* 32, 282-5.

Rovenska, M., Hlouchova, K., Sacha, P., Mlcochova, P., Horak, V., Zamecnik, J., Barinka, C. & Konvalinka, J. (2008) Tissue expression and enzymologic characterization of human prostate specific membrane antigen and its rat and pig orthologs, *The Prostate.* 68, 171-82.

Rowe, S. P., Macura, K. J., Mena, E., Blackford, A. L., Nadal, R., Antonarakis, E. S., Eisenberger, M., Carducci, M., Fan, H., Dannals, R. F., Chen, Y, Mease, R. C., Szabo, Z., Pomper, M. G. & Cho, S. Y. (2016) PSMA-Based [F]DCFPyL PET/CT Is Superior to Conventional Imaging for Lesion Detection in Patients with Metastatic Prostate Cancer, *Molecular imaging and biology: MIB: the official publication of the Academy of Molecular Imaging.*

Sacha, P., Knedlik, T., Schimer, J., Tykvart, J., Parolek, J., Navratil, V., Dvorakova, P., Sedlak, F., Ulbrich, K., Strohalm, J., Majer, P., Subr, V. & Konvalinka, J. (2016) iBodies: Modular Synthetic Antibody Mimetics Based on Hydrophilic Polymers Decorated with Functional Moieties, *Angewandte Chemie.* 55, 2356-60.

Siegel, R. L., Miller, K. D. & Jemal, A. (2015) Cancer statistics, 2015, *CA: a cancer journal for clinicians.* 65, 5-29.

Smith-Jones, P. M., Vallabahajosula, S., Goldsmith, S. J., Navarro, V., Hunter, C. J., Bastidas, D. & Bander, N. H. (2000) In vitro characterization of radiolabeled monoclonal antibodies specific for the extracellular domain of prostate-specific membrane antigen, *Cancer research.* 60, 5237-43.

Sofou, S. (2008) Radionuclide carriers for targeting of cancer, *International journal of nanomedicine.* 3, 181-99.

Tagawa, S. T., Akhtar, N. H., Nikolopoulou, A., Kaur, G., Robinson, B., Kahn, R., Vallabhajosula, S., Goldsmith, S. J., Nanus, D. M. & Bander, N. H. (2013) Bone marrow recovery and subsequent chemotherapy following radiolabeled anti-prostate-specific membrane antigen monoclonal antibody j591 in men with metastatic castration-resistant prostate cancer, *Frontiers in oncology.* 3, 214.

Tagawa, S. T., Milowsky, M. I., Morris, M., Vallabhajosula, S., Christos, P., Akhtar, N. H., Osborne, J., Goldsmith, S. J., Larson, S., Taskar, N. P., Scher, H. I., Bander, N. H. & Nanus, D. M. (2013) Phase II study of Lutetium-177-labeled anti-prostate-specific membrane antigen monoclonal antibody J591 for metastatic castration-resistant prostate cancer, *Clinical cancer research: an official journal of the American Association for Cancer Research.* 19, 5182-91.

Troyer, J. K., Beckett, M. L. & Wright, G. L., Jr. (1997) Location of prostate-specific membrane antigen in the LNCaP prostate carcinoma cell line, *The Prostate.* 30, 232-42.

Tykvart, J., Navratil, V., Sedlak, F., Corey, E., Colombatti, M., Fracasso, G., Koukolik, F., Barinka, C., Sacha, P. & Konvalinka, J. (2014) Comparative analysis of monoclonal antibodies against prostate-specific membrane antigen (PSMA), *The Prostate.* 74, 1674-90.

Tykvart, J., Sacha, P., Barinka, C., Knedlik, T., Starkova, J., Lubkowski, J. & Konvalinka, J. (2012) Efficient and versatile one-step affinity purification of in vivo biotinylated proteins: expression, characterization and structure analysis of recombinant human glutamate carboxypeptidase II, *Protein Expr Purif.* 82, 106-15.

Wernicke, A. G., Kim, S., Liu, H., Bander, N. H. & Pirog, E. C. (2016) Prostate-specific Membrane Antigen (PSMA) Expression in the Neovasculature of Gynecologic Malignancies: Implications for PSMA-targeted Therapy, *Applied immunohistochemistry & molecular morphology: AIMM/official publication of the Society for Applied Immunohistochemistry.*

Wiehr, S., Buhler, P., Gierschner, D., Wolf, P., Rolle, A. M., Kesenheimer, C., Pichler, B. J. & Elsasser-Beile, U. (2014) Pharmacokinetics and PET imaging properties of two recombinant anti-PSMA antibody fragments in comparison to their parental antibody, *The Prostate.* 74, 743-55.

Wittrup, K. D., Thurber, G. M., Schmidt, M. M. & Rhoden, J. J. (2012) Practical theoretic guidance for the design of tumor-targeting agents, *Methods in enzymology.* 503, 255-68.

Yang, X., Mease, R. C., Pullambhatla, M., Lisok, A., Chen, Y, Foss, C. A., Wang, Y, Shallal, H., Edelman, H., Hoye, A. T., Attardo, G., Nimmagadda, S. & Pomper, M. G. (2016) [(18)F]Fluorobenzoyllysinepentanedioic Acid Carbamates: New Scaffolds for Positron Emission Tomography (PET) Imaging of Prostate-Specific Membrane Antigen (PSMA), *Journal of medicinal chemistry* 59, 206-18.

Zhu, C., Bandekar, A., Sempkowski, M., Banerjee, S. R., Pomper, M. G., Bruchertseifer, F., Morgenstern, A. & Sofou, S. (2016) Nanoconjugation of PSMA-Targeting Ligands Enhances Perinuclear Localization and Improves Efficacy of Delivered Alpha-Particle Emitters against Tumor Endothelial Analogues, *Molecular cancer therapeutics.* 15, 106-13.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An isolated antibody or antigen-binding antibody fragment thereof that specifically binds to human prostate specific membrane antigen (PSMA) and that comprises a heavy chain comprising SEQ ID NO: 7 and a light chain comprising SEQ ID NO: 6.

2. The antibody or antigen-binding antibody fragment of claim 1, wherein the antibody or antigen-binding antibody fragment comprises a VL-CL domain comprising SEQ ID NO: 6 and a VH-CH1 domain comprising SEQ ID NO: 7.

3. The antibody or antigen-binding antibody fragment of claim 1, wherein the antibody or antigen-binding antibody fragment comprises a VL-CL domain having an amino acid sequence that is SEQ ID NO: 6 and a VH-CH1 domain having an amino acid sequence that is SEQ ID NO: 7.

4. The antibody or antigen-binding antibody fragment claim 1, wherein the antibody or antigen-binding antibody fragment is conjugated to an imaging agent.

5. The antibody or antigen-binding antibody fragment of claim 1, wherein the antibody is a chimeric antibody or the antigen-binding antibody fragment is a fragment of a chimeric antibody.

6. The antibody or antigen-binding antibody fragment of claim 1, wherein the antibody or antigen-binding antibody fragment is conjugated to at least one agent.

7. The antibody or antigen-binding antibody fragment of claim 6, wherein the at least one agent is a therapeutic agent or an imaging agent.

8. The antibody or antigen-binding antibody fragment of claim 6, wherein the at least one agent is a radionuclide, a toxin, or a fluorophore.

9. The antibody or antigen-binding antibody fragment of claim 8, wherein the radionuclide is selected from the group consisting of $^{11}$C, $^{13}$N, $^{15}$O, $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, $^{211}$At, $^{89}$Zr, $^{90}$Y, $^{86}$Y, $^{177}$Lu, $^{225}$Ac, $^{213}$Bi, $^{212}$Bi, $^{227}$Th, $^{212}$Pb, $^{111}$In, $^{115}$In, $^{203}$Pb, $^{60}$Cu, $^{62}$Cu, $^{64}$Cu, $^{223}$Ra, $^{67}$Ga, $^{68}$Ga, $^{115}$In, $^{203}$Pb, and $^{18}$F.

10. The antibody or antigen-binding antibody fragment of claim 6, wherein the antibody or antigen-binding antibody fragment is conjugated to the at least one agent via a linker.

11. A pharmaceutical or diagnostic composition comprising the antibody or antigen-binding antibody fragment of claim 1.

12. A method for imaging human prostate specific membrane antigen (PSMA)-expressing cells in a subject, said method comprising:
   (a) administering the antibody or antigen-binding antibody fragment of claim 8 to a subject; and
   (b) obtaining an image of cells or tissues of the subject to which the antibody or antigen-binding antibody fragment binds.

13. The antibody or antigen-binding antibody fragment of claim 1, wherein the antibody or antigen-binding antibody fragment specifically binds to a polypeptide encoded by the nucleotide sequence of SEQ ID NO: 23.

14. The antibody or antigen-binding antibody fragment of claim 1, wherein the antibody or antigen-binding antibody fragment is a Fab fragment, a F(ab2)'-fragment, a single-chain antibody, a bivalent antibody-construct, a synthetic antibody, a multispecific antibody, a diabody, or a Fv-fragment.

15. An isolated antibody or antigen-binding antibody fragment thereof that specifically binds human prostate specific membrane antigen (PSMA) and that comprises:
   a VH domain having the amino acid sequence of SEQ ID NO: 21; and
   a VL domain having the amino acid sequence of SEQ ID NO: 22.

16. The antibody or antigen-binding antibody fragment of claim 15, wherein the antibody or antigen-binding antibody fragment is conjugated to a therapeutic agent or an imaging agent.

17. The antibody or antigen-binding antibody fragment of claim 15, wherein the antibody or antigen-binding antibody fragment is a Fab fragment, a F(ab2)'-fragment, a single-chain antibody, a bivalent antibody-construct, a synthetic antibody, a multispecific antibody, a diabody, or a Fv-fragment.

18. The antibody or antigen-binding antibody fragment of claim 15, wherein the antibody is a chimeric antibody; or the antigen-binding antibody fragment is a fragment of a chimeric antibody.

* * * * *